(12) United States Patent
Liu et al.

(10) Patent No.: US 7,413,712 B2
(45) Date of Patent: Aug. 19, 2008

(54) MICROFLUIDIC ROTARY FLOW REACTOR MATRIX

(75) Inventors: Jian Liu, Pasadena, CA (US); Carl L. Hansen, Pasadena, CA (US); Stephen R. Quake, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 579 days.

(21) Appl. No.: 10/837,025

(22) Filed: Apr. 30, 2004

(65) Prior Publication Data
US 2005/0037471 A1 Feb. 17, 2005

Related U.S. Application Data

(60) Provisional application No. 60/494,432, filed on Aug. 11, 2003.

(51) Int. Cl.
*C12Q 1/68* (2006.01)
*F16K 11/10* (2006.01)
*F15C 1/04* (2006.01)

(52) U.S. Cl. .................. 422/100; 435/6; 435/287.2; 435/7.9

(58) Field of Classification Search ............ 436/6; 422/100; 435/6, 287.2, 7.9
See application file for complete search history.

(56) References Cited

U.S. PATENT DOCUMENTS

| | | | |
|---|---|---|---|
| 2,656,508 A | 10/1953 | Coulter | |
| 3,570,515 A | 3/1971 | Kinner | |
| 3,747,628 A | 7/1973 | Holster et al. | |
| 3,839,176 A | 10/1974 | McCoy et al. | |
| 3,915,652 A | 10/1975 | Natelson | |
| 3,984,307 A | 10/1976 | Kamentsky et al. | |
| 4,046,159 A | 9/1977 | Pegourie | |

(Continued)

FOREIGN PATENT DOCUMENTS

EP 0 592 094 A2 4/1994

(Continued)

OTHER PUBLICATIONS

"Biochips," Nature Biotechnology, vol. 18, Supplement 2000, pp. IT43-IT44, 2000.

(Continued)

*Primary Examiner*—Walter D. Griffin
*Assistant Examiner*—Christine T Mui
(74) *Attorney, Agent, or Firm*—Townsend and Townsend and Crew LLP

(57) ABSTRACT

A microfluidic device comprises a matrix of rotary flow reactors. The microfluidic matrix device offers a solution to the "world-to-chip" interface problem by accomplishing two important goals simultaneously: an economy of scale in reagent consumption is achieved, while simultaneously minimizing pipetting steps. $N^2$ independent assays can be performed with only $2N+1$ pipetting steps, using a single aliquot of enzyme amortized over all reactors. The chip reduces labor relative to conventional fluid handling techniques by using an order of magnitude less pipetting steps, and reduces cost by consuming two to three orders of magnitude less reagents per reaction. A PCR format has immediate applications in medical diagnosis and gene testing. Beyond PCR, the microfluidic matrix chip provides a universal and flexible platform for biological and chemical assays requiring parsimonious use of precious reagents and highly automated processing.

25 Claims, 39 Drawing Sheets

U.S. PATENT DOCUMENTS

| | | |
|---|---|---|
| 4,119,368 A | 10/1978 | Yamakazi |
| 4,153,855 A | 5/1979 | Feingold |
| 4,245,673 A | 1/1981 | Bouteille et al. |
| 4,373,527 A | 2/1983 | Fischell |
| 4,399,219 A | 8/1983 | Weaver |
| 4,434,704 A | 3/1984 | Surjaatmadja |
| 4,575,681 A | 3/1986 | Grosso et al. |
| 4,581,624 A | 4/1986 | O'Connor |
| 4,585,209 A | 4/1986 | Aine et al. |
| 4,662,710 A | 5/1987 | ten Berge |
| 4,675,300 A | 6/1987 | Zare et al. |
| 4,786,165 A | 11/1988 | Yamamoto et al. |
| 4,797,842 A | 1/1989 | Nackman et al. |
| 4,876,504 A | 10/1989 | Blake et al. |
| 4,898,582 A | 2/1990 | Faste |
| 4,908,112 A | 3/1990 | Pace |
| 4,936,465 A | 6/1990 | Zold |
| 4,963,498 A | 10/1990 | Hillman et al. |
| 4,965,743 A | 10/1990 | Malin et al. |
| 4,992,312 A | 2/1991 | Frisch |
| 5,032,381 A | 7/1991 | Bronstein et al. |
| 5,085,562 A | 2/1992 | Van Lintel |
| 5,088,515 A | 2/1992 | Kamen |
| 5,096,388 A | 3/1992 | Weinberg |
| 5,100,627 A | 3/1992 | Buican et al. |
| 5,126,022 A | 6/1992 | Soane et al. |
| 5,126,115 A | 6/1992 | Fujita et al. |
| 5,164,558 A | 11/1992 | Huff et al. |
| 5,171,132 A | 12/1992 | Miyazaki |
| 5,171,764 A | 12/1992 | Katayama et al. |
| 5,224,843 A | 7/1993 | Van Lintel |
| 5,259,737 A | 11/1993 | Kamisuki et al. |
| 5,265,327 A | 11/1993 | Faris et al. |
| 5,290,240 A | 3/1994 | Horres, Jr. |
| 5,307,186 A | 4/1994 | Izumi et al. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom |
| 5,400,741 A | 3/1995 | DeTitta et al. |
| 5,423,287 A | 6/1995 | Usami et al. |
| 5,434,047 A | 7/1995 | Arnold et al. |
| 5,452,878 A | 9/1995 | Gravesen et al. |
| 5,454,472 A | 10/1995 | Benecke et al. |
| 5,487,003 A | 1/1996 | Iwasawa et al. |
| 5,496,009 A | 3/1996 | Farrell et al. |
| 5,498,392 A | 3/1996 | Wilding et al. |
| 5,500,071 A | 3/1996 | Kaltenbach et al. |
| 5,512,131 A | 4/1996 | Kumar et al. |
| 5,525,464 A | 6/1996 | Drmanac et al. |
| 5,529,465 A | 6/1996 | Zengerle et al. |
| 5,558,998 A | 9/1996 | Hammond et al. |
| 5,571,410 A | 11/1996 | Swedberg et al. |
| 5,574,893 A | 11/1996 | Southgate et al. |
| 5,580,523 A | 12/1996 | Bard |
| 5,587,128 A | 12/1996 | Wilding et al. |
| 5,589,136 A | 12/1996 | Northrup et al. |
| 5,593,130 A | 1/1997 | Hansson et al. |
| 5,595,650 A | 1/1997 | Manz |
| 5,608,519 A | 3/1997 | Gourley |
| 5,632,876 A | 5/1997 | Zanzucchi et al. |
| 5,641,400 A | 6/1997 | Kaltenbach et al. |
| 5,642,015 A | 6/1997 | Whitehead et al. |
| 5,656,155 A | 8/1997 | Norcross et al. |
| 5,659,171 A | 8/1997 | Young et al. |
| 5,660,370 A | 8/1997 | Webster |
| 5,661,222 A | 8/1997 | Hare |
| 5,665,070 A | 9/1997 | McPhee |
| 5,681,024 A | 10/1997 | Lisec et al. |
| 5,702,618 A | 12/1997 | Saaski et al. |
| 5,705,018 A | 1/1998 | Hartley |
| 5,716,852 A | 2/1998 | Yager et al. |
| 5,726,751 A | 3/1998 | Altendorf et al. |
| 5,750,015 A | 5/1998 | Soane et al. |
| 5,757,482 A | 5/1998 | Fuchs et al. |
| 5,759,014 A | 6/1998 | Van Lintel |
| 5,775,371 A | 7/1998 | Pan et al. |
| 5,779,868 A | 7/1998 | Parce et al. |
| 5,788,468 A | 8/1998 | Dewa et al. |
| 5,800,690 A | 9/1998 | Chow et al. |
| 5,807,522 A | 9/1998 | Brown et al. |
| 5,812,394 A | 9/1998 | Lewis et al. |
| 5,833,926 A | 11/1998 | Wurzel et al. |
| 5,836,750 A | 11/1998 | Cabuz |
| 5,837,200 A | 11/1998 | Diessel et al. |
| 5,839,722 A | 11/1998 | Berlin et al. |
| 5,842,787 A | 12/1998 | Kopf-Sill et al. |
| 5,852,495 A | 12/1998 | Parce |
| 5,854,684 A | 12/1998 | Stabile et al. |
| 5,856,174 A | 1/1999 | Lipshutz et al. |
| 5,858,187 A | 1/1999 | Ramsey et al. |
| 5,858,649 A | 1/1999 | Asgari et al. |
| 5,863,502 A | 1/1999 | Southgate et al. |
| 5,863,801 A | 1/1999 | Southgate et al. |
| 5,867,399 A | 2/1999 | Rostoker et al. |
| 5,869,004 A | 2/1999 | Parce et al. |
| 5,872,010 A | 2/1999 | Karger et al. |
| 5,875,817 A | 3/1999 | Carter |
| 5,876,187 A | 3/1999 | Afromowitz |
| 5,880,071 A | 3/1999 | Parce et al. |
| 5,885,470 A | 3/1999 | Parce et al. |
| 5,904,824 A | 5/1999 | Oh |
| 5,932,799 A | 8/1999 | Moles |
| 5,942,443 A | 8/1999 | Parce et al. |
| RE36,350 E | 10/1999 | Swedberg et al. |
| 5,971,355 A | 10/1999 | Biegelsen et al. |
| 5,994,696 A | 11/1999 | Tai et al. |
| 5,997,961 A | 12/1999 | Feng et al. |
| 6,004,442 A | 12/1999 | Choulga et al. |
| 6,007,309 A | 12/1999 | Hartley |
| 6,042,709 A | 3/2000 | Parce et al. |
| 6,043,080 A | 3/2000 | Lipshutz et al. |
| 6,048,498 A | 4/2000 | Kennedy |
| 6,056,428 A | 5/2000 | Devoino et al. |
| 6,089,534 A | 7/2000 | Biegelsen et al. |
| 6,103,537 A | 8/2000 | Ullman et al. |
| 6,107,044 A | 8/2000 | Nikiforov |
| 6,123,769 A | 9/2000 | Sanjoh |
| 6,132,685 A | 10/2000 | Kercso et al. |
| 6,149,787 A | 11/2000 | Chow et al. |
| 6,149,870 A | 11/2000 | Parce et al. |
| 6,155,282 A | 12/2000 | Zachary et al. |
| 6,167,910 B1 | 1/2001 | Chow |
| 6,174,365 B1 | 1/2001 | Sanjoh |
| 6,182,020 B1 | 1/2001 | Fairbanks |
| 6,221,654 B1 | 4/2001 | Quake et al. |
| 6,235,175 B1 | 5/2001 | Dubrow et al. |
| 6,246,330 B1 | 6/2001 | Nielsen |
| 6,274,337 B1 | 8/2001 | Parce et al. |
| 6,296,673 B1 | 10/2001 | Santarsiero et al. |
| 6,321,791 B1 | 11/2001 | Chow |
| 6,329,209 B1 | 12/2001 | Wagner et al. |
| 6,345,502 B1 | 2/2002 | Tai et al. |
| 6,358,387 B1 | 3/2002 | Kopf-Sill et al. |
| 6,375,871 B1 | 4/2002 | Bentsen et al. |
| 6,376,971 B1 | 4/2002 | Pelrine et al. |
| 6,408,878 B2 | 6/2002 | Unger et al. |
| 6,409,832 B2 | 6/2002 | Weigl et al. |
| 6,488,832 B2 | 12/2002 | Heller |
| 6,488,872 B1 | 12/2002 | Beebe et al. |
| 6,500,323 B1 | 12/2002 | Chow et al. |
| 6,508,988 B1 | 1/2003 | Van Dam et al. |
| 6,520,936 B1 | 2/2003 | Mann |
| 6,533,914 B1 | 3/2003 | Liu |

| | | | | | | |
|---|---|---|---|---|---|---|
| 6,537,799 | B2 | 3/2003 | Chow et al. | EP | 0 845 603 A1 | 6/1998 |
| 6,540,895 | B1 | 4/2003 | Quake et al. | EP | 0 999 055 A2 | 5/2000 |
| 6,541,071 | B1 | 4/2003 | Bookbinder et al. | EP | 1 065 378 A2 | 1/2001 |
| 6,563,111 | B1 | 5/2003 | Moon et al. | GB | 2 097 692 A | 11/1982 |
| 6,569,382 | B1 | 5/2003 | Edman et al. | GB | 2 155 152 A | 9/1985 |
| 6,581,441 | B1 | 6/2003 | Paul | GB | 2 308 460 A | 6/1997 |
| 6,585,939 | B1 | 7/2003 | Dapprich | WO | WO 98/07069 A1 | 2/1998 |
| 6,596,545 | B1 | 7/2003 | Wagner et al. | WO | WO 98/39645 A1 | 9/1998 |
| 6,605,472 | B1 | 8/2003 | Skinner et al. | WO | WO 98/52691 A1 | 11/1998 |
| 6,627,076 | B2 | 9/2003 | Griffiths | WO | WO 99/00655 A2 | 1/1999 |
| 6,637,463 | B1 | 10/2003 | Lei et al. | WO | WO 99/04361 A1 | 1/1999 |
| 6,662,818 | B2 | 12/2003 | Paul et al. | WO | WO 99/17093 A1 | 4/1999 |
| 6,664,104 | B2 | 12/2003 | Pourahmadi et al. | WO | WO 99/52633 A1 | 10/1999 |
| 6,667,124 | B2 | 12/2003 | Suenaga et al. | WO | WO 99/61888 A2 | 12/1999 |
| 6,677,131 | B2 | 1/2004 | Yuen | WO | WO 00/00678 A1 | 1/2000 |
| 6,689,473 | B2 | 2/2004 | Guire et al. | WO | WO 00/21666 A1 | 4/2000 |
| 6,713,327 | B2 | 3/2004 | Leedy | WO | WO 00/22409 A2 | 4/2000 |
| 6,716,378 | B2 | 4/2004 | Yang et al. | WO | WO 00/30167 A1 | 5/2000 |
| 6,736,978 | B1 | 5/2004 | Porter et al. | WO | WO 00/43748 A1 | 7/2000 |
| 6,749,814 | B1 | 6/2004 | Bergh et al. | WO | WO 00/60345 A1 | 10/2000 |
| 6,752,922 | B2 | 6/2004 | Huang et al. | WO | WO 01/01025 A2 | 1/2001 |
| 6,765,279 | B2 | 7/2004 | Leedy | WO | WO 01/06529 A1 | 1/2001 |
| 6,767,706 | B2 | 7/2004 | Quake et al. | WO | WO 01/06575 A1 | 1/2001 |
| 6,829,753 | B2 | 12/2004 | Lee et al. | WO | WO 01/09595 A2 | 2/2001 |
| 6,847,153 | B1 | 1/2005 | Balizer | WO | WO 01/09595 A3 | 2/2001 |
| 6,866,785 | B2 | 3/2005 | Zare et al. | WO | WO 01/53794 A1 | 7/2001 |
| 6,884,346 | B2 | 4/2005 | Zare et al. | WO | WO 01/94635 A2 | 12/2001 |
| 6,885,982 | B2 | 4/2005 | Harris et al. | WO | WO 02/30486 A2 | 4/2002 |
| 6,960,437 | B2 * | 11/2005 | Enzelberger et al. ............ 435/6 | WO | WO 02/40874 A1 * | 5/2002 |
| 2001/0027745 | A1 | 10/2001 | Weigl et al. | WO | WO 02/43615 A2 | 6/2002 |
| 2001/0041357 | A1 | 11/2001 | Fouillet et al. | WO | WO 02/60582 A2 | 8/2002 |
| 2002/0005354 | A1 | 1/2002 | Spence et al. | WO | WO 02/82047 A2 | 10/2002 |
| 2002/0014673 | A1 | 2/2002 | Leedy | WO | WO 03/037781 A1 | 5/2003 |
| 2002/0037499 | A1 | 3/2002 | Quake et al. | | | |
| 2002/0045297 | A1 | 4/2002 | Leedy | | | |
| 2002/0058332 | A1 | 5/2002 | Quake et al. | | | |
| 2002/0064885 | A1 | 5/2002 | Bedingham et al. | | | |
| 2002/0108096 | A1 | 8/2002 | Lee et al. | | | |
| 2002/0108097 | A1 | 8/2002 | Harris et al. | | | |
| 2002/0109114 | A1 | 8/2002 | Driggs et al. | | | |
| 2002/0127736 | A1 | 9/2002 | Fu et al. | | | |
| 2002/0158022 | A1 | 10/2002 | Huang et al. | | | |
| 2002/0164816 | A1 | 11/2002 | Quake | | | |
| 2002/0183996 | A1 | 12/2002 | Lee et al. | | | |
| 2002/0197603 | A1 | 12/2002 | Chow et al. | | | |
| 2003/0008308 | A1 * | 1/2003 | Enzelberger et al. ............ 435/6 | | | |
| 2003/0019833 | A1 | 1/2003 | Unger et al. | | | |
| 2003/0049659 | A1 | 3/2003 | Lapidus et al. | | | |
| 2003/0080442 | A1 | 5/2003 | Unger | | | |
| 2003/0134129 | A1 | 7/2003 | Lammertink et al. | | | |
| 2003/0143120 | A1 | 7/2003 | Ruediger et al. | | | |
| 2003/0175947 | A1 | 9/2003 | Liu et al. | | | |
| 2004/0072278 | A1 | 4/2004 | Chou et al. | | | |
| 2004/0096960 | A1 | 5/2004 | Burd Mehta et al. | | | |
| 2004/0141887 | A1 | 7/2004 | Mainquist et al. | | | |
| 2004/0209354 | A1 | 10/2004 | Mathies et al. | | | |
| 2004/0248167 | A1 | 12/2004 | Quake et al. | | | |
| 2005/0000900 | A1 | 1/2005 | Huang et al. | | | |
| 2005/0019792 | A1 | 1/2005 | McBride et al. | | | |
| 2005/0053952 | A1 | 3/2005 | Hong et al. | | | |
| 2005/0065735 | A1 | 3/2005 | Lee et al. | | | |
| 2005/0084421 | A1 | 4/2005 | Unger et al. | | | |
| 2005/0129581 | A1 | 6/2005 | McBride et al. | | | |
| 2005/0164376 | A1 | 7/2005 | Balagadde et al. | | | |
| 2005/0180891 | A1 | 8/2005 | Webster | | | |
| 2005/0197652 | A1 | 9/2005 | Nat | | | |

FOREIGN PATENT DOCUMENTS

| | | |
|---|---|---|
| EP | 0 703 364 A1 | 3/1996 |
| EP | 0 706 004 A2 | 4/1996 |
| EP | 0 779 436 A2 | 6/1997 |
| EP | 0 829 360 A2 | 3/1998 |

OTHER PUBLICATIONS

"Chapter 9: Microfluidic Devices," Micromachined Transducers Sourcebook, pp. 779-882, 1998.

"Electro Microfluidic Dual In-Line Package (EMDIP)," Sandia National Laboratories, 2 pages, no date.

"Last Chance For Micromachines," The Economist Technology Quarterly, printed from website http://www.economist.com/science/displayStory.cfm?Story_ID=442930 on Jan. 25, 2001, 8 pages, Dec. 7, 2000.

"The Liver Chip," Technology Review, pp. 64-67, Mar. 2003.

Ahn, Chong H. et al., "Fluid Micropumps Based On Rotary Magnetic Actuators," Proceedings of 1995 IEEE Micro Electro Mechanical Systems Workshop (MEMS '95), Amsterdam, Netherlands, pp. 408-412, Jan. 29-Feb. 2, 1995.

Anderson, Janelle R. et al., "Fabrication Of Topologically Complex Three-Dimensional Microfluidic Systems In PDMS By Rapid Prototyping," Analytical Chemistry, vol. 72, No. 14, pp. 3158-3164, Jul. 15, 2000.

Anderson, Rolfe C. et al., "Microfluidic Biochemical Analysis System," Transducers '97, 1997 International Conference on Solid-State Sensors and Actuators, Chicago, Illinois, pp. 477-480, Jun. 16-19, 1997.

Angell, James B. et al., "Silicon Micromechanical Devices," Scientific American, pp. cover, 44-55, Apr. 1983.

Armani, Deniz et al., "Re-Configurable Fluid Circuits By PDMS Elastomer Micromachining," IEEE Int. Conf. Micro Electro Mech. Syst. Tech. Digest. vol. 12, pp. 222-227, 1999.

Ballantyne, J. P. et al., "Selective Area Metallization By Electron-Beam Controlled Direct Metallic Deposition," J. Vac. Sci. Technol., vol. 10, No. 6, pp. 1094-1097, Nov. 1973.

Belgrader, Phillip et al., "Rapid Pathogen Detection Using A Microchip PCR Array Instrument," Clinical Chemistry, vol. 44, No. 10, pp. 2191-2194, 1998.

Benard, W. L. et al., "A Titanium-Nickel Shape-Memory Alloy Actuated Micropump," Transducers '97, 1997 International Conference on Solid-State Sensors and Actuators, Chicago, Illinois, pp. 361-364, Jun. 16-19, 1997.

Black, Harvey, "Tiny Technology Promises Tremendous Profits," The Scientist, vol. 15, No. 21, 4 pages, Oct. 29, 2001.

Bloomstein, T. M. et al., "Laser-Chemical Three-Dimensional Writing For Microelectromechanics And Application To Standard-Cell Microfluidics," J. Vac. Sci. Technol. B, vol. 10, No. 6, pp. 2671-2674, Nov. 1992.

Bousse, Luc et al., "Electrokinetically Controlled Microfluidic Analysis Systems," Annu. Rev. Biophys. Biomol. Struct., vol. 29, pp. 155-181, 2000.

Brechtel, R. et al., "Control Of The Electroosmotic Flow By Metal-Salt-Containing Buffers," Journal of Chromatography A, vol. 716, pp. 97-105, 1995.

Brush, Michael, "Automated Laboratories," The Scientist, vol. 13, No. 4, 10 pages, Feb. 15, 1999.

Bryzek, Janusz et al., "Micromachines On The March", IEEE Spectrum, vol. 31, No. 5, pp. 20-31, May 1994.

Buchaillot, Lionel et al., "Silicon Nitride Thin Films Young's Modulus Determination By An Optical Non Destrcutive Method," Jpn. J. Appl. Phys., vol. 36, Part 2, No. 6B, pp. L794-L797, Jun. 15, 1997.

Burbaum, Jonathan J. et al., "New Technologies For High-Throughput Screening," Current Opinion in Chemical Biology, vol. 1, pp. 72-78, 1997.

Cai, Warren, et al., "High-Resolution Restriction Maps Of Bacterial Artificial Chromosomes Constructed By Optical Mapping," Proc. Natl. Acad. Sci. USA, vol. 95, pp. 3390-3395, Mar. 1998.

Calkins, Kathryn, " Mycometrix: Rubber Chips," BioCentury, 2 pages, Oct. 16, 2000.

Castro, Alonso et al., "Fluorescence Detection And Size Measurement Of Single DNA Molecules," Analytical Chemistry, vol. 85, No. 7, pp. 849-852, Apr. 1, 1993.

Chan, Jason H. et al., "Microfabricated Polymer Devices For Automated Sample Delivery Of Peptides For Analysis By Electrospray Ionization Tandem Mass Spectrometry," Analytical Chemistry, vol. 71, No. 20, pp. 4437-4444, Oct. 15, 1999.

Chang, Jun Keun et al., "Functional Integration Of Serial Dilution And Capillary Electrophoresis On A PDMS Microchip," Biotechnology and Bioprocess Engineering, vol. 8, No. 4, pp. 233-239, 2003.

Chen, Chihchen et al., "Gray-Scale Photolithography Using Microfluidic Photomasks," PNAS, vol. 100, No. 4, pp. 1499-1504, Feb. 18, 2003.

Chiang, Yuh-Min et al., "Characterizing The Process Of Cast Molding Microfluidic Systems," SPIE, vol. 3877, pp. 303-311, Sep. 1999.

Chiu, Chi-Sung et al., "Single Molecule Measurements Calibrate Green Fluorescent Protein Surface Densities On Transparent Beads For Use With 'Knock-In' Animals And Other Expression Systems," Journal of Neuroscience Methods, vol. 105, pp. 55-63, 2001.

Chiu, Daniel T. et al., "Patterned Deposition Of Cells And Proteins Onto Surfaces By Using Three-Dimensional Microfluidic Systems," PNAS, vol. 97, No. 6, pp. 2408-2413, Mar. 14, 2000.

Chou, Hou-Pu et al., "A Microfabricated Device For Sizing And Sorting DNA Molecules," Proc. Natl. Acad. Sci., vol. 96, pp. 11-13, Jan. 1999.

Chou, Hou-Pu et al., "A Microfabricated Rotary Pump," Biomedical Microdevices, vol. 3, No. 4, pp. 323-330, 2001.

Chou, Hou-Pu et al., "Integrated Elastomer Fluidic Lab-On-A-Chip-Surface Patterning And DNA Diagnostics," Proceedings of the Solid State Actuator and Sensor Workshop, Hilton Head, South Carolina, 4 pages, 2000.

Chou, Hou-Pu et al., "Multiple Disease Diagnostics On A Single Chip," Biophysics Lab, Caltech, pp. 1-4, Mar. 1, 2000.

Delamarche, Emmanuel et al., "Patterned Delivery Of Immunoglobulins To Surfaces Using Microfluidic Networks," Science, vol. 276, pp. 779-781, May 2, 1997.

Dharmatilleke, Saman et al., "Three-Dimensional Silicone Device Fabrication And Interconnection Scheme For Microfluidic Applications Using Sacrificial Wax Layers," Micro-Electro-Mechanical Systems (MEMS), vol. 2, pp. 413-418, 2000.

Duffy, David C. et al., "Patterning Electroluminescent Materials With Feature Sizes As Small As 5μm Using Elastomeric Membranes As Masks For Dry Lift-Off," Advanced Materials, vol. 11, No. 7, pp. 546-552, 1999.

Duffy, David C. et al., "Rapid Prototyping Of Microfluidic Switches In Poly(dimethyl siloxane) And Their Actuation By Electro-Osmotic Flow," J. Micromech. Microeng., vol. 9, pp. 211-217, 1999.

Duffy, David C. et al., "Rapid Prototyping Of Microfluidic Systems In Poly(dimethylsiloxane)," Analytical Chemistry, vol. 70, No. 23, pp. 4974-4984, Dec. 1, 1998.

Effenhauser, Carlo S. et al., "Integrated Capillary Electrophoresis On Flexible Silicone Microdevices: Analysis Of DNA Restriction Fragments And Detection Of Single DNA Molecules On Microchips," Analytical Chemistry, vol. 69, No. 17, pp. 3451-3457, Sep. 1, 1997.

Effenhauser, Carlo S. et al., "Integrated Chip-Based Capillary Electrophoresis," Electrophoresis, vol. 18, pp. 2203-2213, 1997.

Ericson, Christer et al., "Electroosmosis- And Pressure-Driven Chromatography In Chips Using Continuous Beds," Analytical Chemistry, vol. 72, No. 1, Jan. 1, 2000.

Eyal, Shulamit et al., "Velocity-Independent Microfluidic Flow Cytometry," Electrophoresis, vol. 23, pp. 2653-2657, 2002.

Fahrenberg, J. et al., "A Microvalve System Fabricated By Thermoplastic Molding," J. Micromech. Microeng., vol. 5, pp. 169-171, 1995.

Fettinger, J. C. et al., "Stacked Modules For Micro Flow Systems In Chemical Analysis: Concept And Studies Using An Enlarged Model," Sensors and Actuators B, vol. 17, pp. 19-25, 1993.

Figeys, Daniel et al., "An Integrated Microfluidics-Tandem Mass Spectrometry System For Automated Protein Analysis," Analytical Chemistry, vol. 70, No. 18, pp. 3728-3734, Sep. 15, 1998.

Figeys, Daniel et al., "Nanoflow Solvent Gradient Delivery From A Microfabricated Device For Protein Identifications By Electrospray Ionization Mass Spectrometry," Analytical Chemistry, vol. 70, No. 18, pp. 3721-3727, Sep. 15, 1998.

Fitzgerald, Deborah A., "Making Every Nanoliter Count," The Scientist, vol. 15, No. 21, 8 pages, Oct. 29, 2001.

Folch, A. et al., "Molding Of Deep Polydimethylsiloxane Microstructures For Microfluidics And Biological Applications," Journal of Biomechanical Engineering, vol. 121, pp. 28-34, Feb. 1999.

Fu, Anne Y. et al., "A Microfabricated Fluorescence-Activated Cell-Sorter," Nature Biotechnology, vol. 17, pp. 1109-1111, Nov. 1999.

Galambos, Paul et al., "Electrical And Fluidic Packaging Of Surface Micromachined Electro-Microfluidic Devices," 8 pages, no date.

Gao, Jun et al., "Integrated Microfluidic System Enabling Protein Digestion, Peptide Separation, And Protein Identification," Analytical Chemistry, vol. 73, No. 11, pp. 2648-2655, Jun. 1, 2001.

Garno, Jayne C. et al., "Production Of Periodic Arrays Of Protein Nanostructures Using Particle Lithography," Langmuir, vol. 18, No. 21, pp. 8166-8192, 2002.

Gass, V. et al., "Integrated Flow-Regulated Silicon Micropump," Sensors and Actuators A, vol. 43, pp. 335-338, 1994.

Gerlach, Torsten, "Pumping Gases By A Silicon Micro Pump With Dynamic Passive Valves," Transducers '97, 1997 International Conference on Solid-State Sensors and Actuators, Chicago, Illinois, pp. 357-360, Jun. 16-19, 1997.

Goll, C. et al., "Microvalves With Bistable Buckled Polymer Diaphragms," J. Micromech. Microeng., vol. 6, pp. 77-79, 1996.

Gravesen, Peter et al., "Microfluidics-A Review," J. Micromech. Microeng., vol. 3, pp. 168-192, 1993.

Greene, Chana, "Characterizing The Properties Of PDMS," pp. 1-11, Summer 2000.

Grover, William H. et al., "Monolithic Membrane Valves And Diaphragm Pumps For Practical Large-Scale Integration Into Glass Microfluidic Devices," Sensors and Actuators B, vol. 89, pp. 315-323, 2003.

Guérin, L. J. et al., "Simple And Low Cost Fabrication Of Embedded Micro-Channels By Using A New Thick-Film Photoplastic," Transducers '97, 1997 International Conference on Solid-State Sensors and Actuators, Chicago, Illinois, pp. 1419-1422, Jun. 18-19, 1997.

Hansen, Carl. L. et al., "A Robust And Scalable Microfluidic Metering Method That Allows Protein Crystal Growth By Free Interface Diffusion," PNAS, vol. 99, No. 26, pp. 16531-16536, Dec. 24, 2002.

Harrison, D. Jed et al., "Micromachining A Miniaturized Capillary Electrophoresis-Based Chemical Analysis System On A Chip," Science, vol. 261, pp. 895-897, Aug. 13, 1993.

Henion, Jack et al., "Capillary Electrophoresis/Mass Spectrometry: From One Meter Capillaries To Chip-Based Devices," 2 pages, 1999.

Hicks, Jennifer, "Genetics And Drug Discovery Dominate Microarray Research," R&D Magazine, pp. 28-33, Feb. 1999.

Hofmann, Oliver et al., "Modular Approach To Fabrication Of Three-Dimensional Microchannel Systems In PDMA—Application To Sheath Flow Microchips," Lab on a Chip, vol. 1, pp. 108-114, 2001.

Hong, Jong Wook et al., "A Nanoliter-Scale Nucleic Acid Processor With Parallel Architecture," Nature Biotechnology, vol. 22, No. 4, pp. 1-5, Apr. 2004.

Hopfgartner, Gerard et al., "Exact Mass Measurement Of Product Ions For The Structural Elucidation Of Drug Metabolites With A Tandem Quadrupole Orthogonal-Acceleration Time-Of-Flight Mass Spectrometer," Journal of The American Society for Mass Spectrometry, vol. 10, pp. cover, 1305-1314, Dec. 1999.

Horn, Howard, "Lab Chips Sector: Microtechnologies Are Changing Healthcare And More," Life Science, pp. 19-21, Mar. 30, 2001.

Hornbeck, Larry J. et al., "Bistable Deformable Mirror Device," Spatial Light Modulators and Applications 1988 Technical Digest Series, Summaries of papers presented at the Spatial Light Modulators and Applications Topical Meeting, Optical Society of America, vol. 8, Postconference Edition, A215, pp. 107-110, Jun. 15-19, 1988.

Hosokawa, Kazuo et al., "A Microfluidic Device For Mixing Of Capillary-Drive Liquids," IEEJ Trans. SM, vol. 123, No. 1, pp. 23-24, 2003.

Hosokawa, Kazuo et al., "Droplet-Based Nano/Picoliter Mixer Using Hydrophobic Microcapillary Vent," 1999 IEEE International Conference on Micro Electro Mechanical Systems, Technical Digest, pp. 388-393, 1999.

Hosokawa, Kazuo et al., "Handling Of Picoliter Liquid Samples In A Poly(dimethylsiloxane)-Based Microfluidic Device," Analytical Chemistry, vol. 71, No. 20, pp. 4781-4785, Oct. 15, 1999.

Ikuta, Koji et al., "Three Dimensional Micro Integrated Fluid Systems (MIFS) Fabricated By Stereo Lithography," IEEE, pp. 1-6, 1994.

Jacobson, Stephen C. et al., "High-Speed Separations On A Microchip," Analytical Chemistry, vol. 66, No. 7, pp. 1114-1118, Apr. 1, 1994.

Jacobson, Stephen C. et al., "Microfluidic Devices For Electrokinetically Driven Parallel And Serial Mixing," Analytical Chemistry, vol. 71, No. 20, pp. 4455-4459, Oct. 15, 1999.

Jerman, Hal, "Electrically-Activated, Normally-Closed Diaphragm Valves," Transducers '91, 1991 International Conference on Solid-State Sensors and Actuators, pp. cover, 1045-1048, 1991.

Jo, Byung-Ho et al., "Fabrication Of Three-Dimensional Microfluidic Systems By Stacking Molded Polydimethylsiloxane (PDMS) Layers" SPIE, vol. 3877, pp. 222-229, Sep. 1999.

Jo, Byung-Ho et al., "Three-Dimensional Micro-Channel Fabrication In Polydimethylsiloxane (PDMS) Elastomer," Journal of Microelectromechanical Systems, vol. 9, No. 1, pp. 76-81, Mar. 2000.

Jung, D. R. et al., "Chemical And Physical Interactions At Metal/Self-Assembled Organic Monolayer Interfaces," pp. 1-54, 1994.

Kagan, C. R., "Organic-Inorganic Hybrid Materials As Semiconducting Channels In Thin-Film Field-Effect Transistors," Science, vol. 286, pp. 945-947, Oct. 29, 1999.

Kapur, Ravi et al., "Fabrication And Selective Surface Modification Of 3-Dimensionally Textured Biomedical Polymers From Etched Silicon Substrates," Journal of Biomedical Materials Research, vol. 33, pp. 205-216, 1996.

Kawano, Yasushi et al., "Rapid Isolation And Identification Of Staphylococcal Exoproteins By Reverse Phase Capillary High Performance Liquid Chromatography-Electrospray Ionization Mass Spectrometry," FEMS Microbiology Letters, vol. 189, pp. 103-108, 2000.

Keller, Richard A. et al., "Single-Molecule Fluorescence Analysis In Solution," Applied Spectroscopy, vol. 50, No. 7, pp. 12A-30A, Jul. 1996.

Kenis, Paul J. A. et al., "Microfabrication Inside Capillaries Using Multiphase Laminar Flow Patterning," Science, vol. 285, pp. 83-85, Jul. 2, 1999.

Khoo, Melvin et al., "A Novel Micromachined Magnetic Membrane Microfluid Pump," pp. 1-4, no date.

Kim, Enoch et al., "Micromolding In Capillaries: Applications In Materials Science," J. Am. Chem. Soc., vol. 118, No. 24, pp. 5722-5731, 1996.

Kim, Enoch et al., "Polymer Microstructures Formed By Moulding In Capillaries," Nature, vol. 376, pp. 581-584, Aug. 17, 1995.

Kirk-Othmer, "Concise Encyclopedia of Chemical Technology," John Wiley & Sons, 5 pages, no date.

Kopp, Martin U. et al., "Chemical Amplification: Continuous-Flow PCR On A Chip," Science, vol. 280, pp. 1046-1048, May 15, 1998.

Kuhn, Lawrence et al., "Silicon Charge Electrode Array For Ink Jet Printing," IEEE Transactions on Electron Devices, vol. ED-25, No. 10, pp. 1257-1260, Oct. 1978.

Kumar, Amit et al., "Features Of Gold Having Micrometer To Centimeter Dimensions Can Be Formed Through A Combination Of Stamping With An Elastomeric Stamp And An Alkanethiol 'Ink' Followed By Chemical Etching," Appl. Phys. Lett., vol. 63, No. 14, pp. 2002-2004, Oct. 4, 1993.

Kumar, Amit et al., "Patterning Self-Assembled Monolayers: Applications In Materials Science," Langmuir, vol. 10, pp. 1498-1511, 1994.

Lagally, Eric T. et al., "Fully Integrated PCR-Capillary Electrophoresis Microsystem For DNA Analysis," Lab On A Chip, vol. 1, pp. 102-107, 2001.

Lagally, Eric T. et al., "Monolithic Integrated Microfluidic DNA Amplification And Capillary Electrophoresis Analysis System," Sensors and Actuators B, vol. 63, pp. 138-146, 2000.

Lagally, E. T. et al., "Single-Module DNA Amplification And Analysis In An Integrated Microfluidic Device," Analytical Chemistry, vol. 73, No. 3, pp. 565-570, Feb. 1, 2001.

Lammerink, T. S. J. et al., "Modular Concept For Fluid Handling Systems," IEEE, pp. 389-394, 1996.

Lazar, Iulia M. et al., "Novel Microfabricated Device For Electrokinetically Induced Pressure Flow And Electrospray Ionization Mass Spectrometry," Journal of Chromatography A, vol. 892, pp. 195-201, 2000.

Lessard, Guillaume A. et al., "A Scanning Apertureless Fluorescence Microscope," 8 pages, no date.

Li, Jianjun et al., "Integration Of Microfabricated Devices To Capillary Electrophoresis-Electrospray Mass Spectrometry Using A Low Dead Volume Connection: Application To Rapid Analyses Of Proteolytic Digests," Analytical Chemistry, vol. 71, No. 15, pp. 3036-3045, Aug. 1, 1999.

Li, Paul C. H. et al., "Transport, Manipulation, And Reaction Of Biological Cells On-Chip Using Electrokinetic Effects," Analytical Chemistry, vol. 69, No. 8, pp. 1564-1568, Apr. 15, 1997.

Licklider, Larry et al., "A Micromachined Chip-Based Electrospray Source For Mass Spectrometry," Analytical Chemistry, vol. 72, No. 2, pp. 367-375, Jan. 15, 2000.

Lin, L. Y. et al., "Free-Space Micromachined Optical Switches For Optical Networking," IEEE Journal of Selected Topics in Quantum Electronics, vol. 5, No. 1, pp. 4-9, Jan. 1999.

Lin, Yuehe et al., "Laser Micromachined Isoelectric Focusing Device On Polymer Substrate For Electrospray Mass Spectrometry," SPIE, vol. 3877, pp. 28-35, Sep. 1999.

Liu, Hanghui et al., "Development Of Multichannel Devices With An Array Of Electrospray Tips For High-Throughput Mass Spectrometry," Analytical Chemistry, vol. 72, No. 14, pp. 3303-3310, Jul. 15, 2000.

Liu, Jian et al., "A Nanoliter Rotary Device For Polymerase Chain Reaction," Electrophoresis, vol. 23, pp. 1531-1536, 2002.

Lötters, J C et al., "The Mechanical Properties Of The Rubber Elastic Polymer Polydimethylsiloxane For Sensor Applications," J. Micromech. Microeng., vol. 7, pp. 145-147, 1997.

Lucy, Charles A. et al., "Characterization Of The Cationic Surfactant Induced Reversal Of Electroosmotic Flow In Capillary Electrophoresis," Anal. Chem., vol. 68, pp. 300-305, 1996.

Maluf, N., "An Introduction To Microelectromechanical Systems Engineering," Artech House Publishers, Boston London, pp. 42-45, Dec. 1999.

Manz, A. et al., "Micromachining Of Monocrystalline Silicon And Glass For Chemical Analysis Systems," Trends in Analytical Chemistry, vol. 10, No. 5, pp. 144-149, 1991.

Marshall, Sid, "Fundamental Charges Ahead For Lab Instrumentation," R&D Magazine, 5 pages, Feb. 1999.

Marsili, Ray, "Lab-On-A-Chip Poised To Revolutionize Sample Prep," R&D Magazine, 5 pages, Feb. 1999.

McDonald, J. Cooper et al., "Fabrication Of Microfluidic Systems In Poly(dimethylsiloxane)," Electrophoresis, vol. 21, pp. 27-40, 2000.

McDonald, J. Cooper et al., "Poly(dimethylsiloxane) As A Material For Fabricating Microfluidic Devices," Accounts of Chemical Research, vol. 35, No. 7, pp. 491-499, 2002.

Muller, Richard S. et al., "Surface-Micromachined Microoptical Elements And Systems," Proceedings of the IEEE, vol. 86, No. 8, pp. 1705-1720, Aug. 1998.

New Objective website, "What Is Electrospray," www.newobjective.com/electrospray.html, 4 pages, Sep. 22, 2000.

Ng, Jessamine M. K. et al., "Components For Integrated Poly(Dimethylsiloxane) Microfluidic Systems," Electrophoresis, vol. 23, pp. 3461-3473, 2002.

Oleschuk, Richard D. et al., "Analytical Microdevices For Mass Spectrometry," Trends In Analytical Chemistry, vol. 19, No. 6., pp. 379-388, 2000.

Olsson, Anders et al., "Simulation Studies Of Diffuser And Nozzle Elements For Valve-Less Micropumps," Transducers '97, 1997 International Conference on Solid-State Sensors and Actuators, Chicago, Illinois, pp. 1039-1042, Jun. 16-19, 1997.

Pethig, Ronald et al., "Applications Of Dielectrophoresis In Biotechnology," Tibtech, vol. 15, pp. 426-432, Oct. 1997.

Protana website, "NanoES Products," www.protana.com/products/default.asp, 3 pages, Sep. 19, 2000.

Qin, Dong et al., "Elastomeric Light Valves," Adv. Mater., vol. 9, No. 5, pp. 407-410, 1997.

Qin, Dong et al., "Photolithography With Transparent Reflective Photomasks," J. Vac. Sci. Technol. B, vol. 16, No. 1, pp. 98-103, Jan. 1998.

Quake, Stephen T. et al., "From Micro- To Nanofabrication With Soft Materials," Science, vol. 290, pp. 1536-1540, Nov. 24, 2000.

Rapp, R. et al., "LIGA Micropump For Gases And Liquids," Sensors and Actuators A, vol. 40, pp. 57-61, Jan. 1994.

Roylance, Lynn Michelle et al., "A Batch-Fabricated Silicon Accelerometer," IEEE Transactions on Electron Devices, vol. ED-26, No. 12, pp. 1911-1917, Dec. 1979.

Samad, Akhtar et al., "Optical Mapping: A Novel, Single-Molecule Approach To Genomic Analysis," Genome Research, pp. 1-4, 1995.

Sanjoh, Akira et al., "Spatiotemporal Protein Crystal Growth Studies Using Microfluidic Silicon Devices," Journal of Crystal Growth, vol. 196, pp. 691-702, 1999.

Sasserath, J. et al., "Rapid Prototyping And Development Of Microfluidic And BioMEMS Devices," IVD Technology, 12 pages, Jun. 2002.

Schasfoort, Richard B. M. et al., "Field-Effect Flow Control For Microfabricated Fluidic Networks," Science, vol. 286, pp. 942-945, Oct. 29, 1999.

Schomburg, W. K. et al., "Fabrication Of Polymer Microcomponents With The Amanda-Process," New Materials and Directions, Eurosensors XII, pp. 711-714, Sep. 13-16, 1998.

Schueller, Olivier J. A. et al., "Fabrication Of Glassy Carbon Microstructures By Soft Lithography," Sensors and Actuators A, vol. 72, pp. 126-139, 1999.

Schwartz, David C. et al., "Optical Mapping Approaches To Molecular Genomics," Current Opinion in Biotechnology, vol. 8, pp. 70-74, 1997.

Shevchenko, Andrej et al., "Rapid 'de Novo 'Peptide Sequencing By A Combination Of Nanoelectrospray, Isotopic Labeling And A Quadrupole/Time-Of-Flight Mass Spectometer," Rapid Communications in Mass Spectrometry, vol. 11, pp. 1015-1024, 1997.

Shinohara, Jun et al., "A High Pressure-Resistance Micropump Using Active And Normally-Closed Valves," IEEE, pp. 86-91, 2000.

Shoji, Shuichi, "Fluids For Sensor Systems," Topics in Current Chemistry, vol. 194, pp. 167-188, 1998.

Shoji, Shuichi et al., "Smallest Dead Volume Microvalves For Integrated Chemical Analyzing Systems," Transducers '91, 1991 International Conference on Solid-State Sensors and Actuators, San Francisco, California, pp. cover, 1052-1055, 1991.

Smits, J.G., "Piezoelectric Micropump With Three Valves Working Peristaltically," Sensors and Actuators, vol. A21-A23, pp. 203-206, 1990.

Sohn, L. L. et al. "Capacitance Cytometry: Measuring Biological Cells One By One," PNAS, vol. 97, No. 20, pp. 10687-10690, Sep. 26, 2000.

Thompson, L. F. et al., "Introduction To Microlithography," 185th Meeting of the American Chemical Society, Seattle, WA, pp. 2 cover pages, 1-13, Mar. 20-25, 1983.

Thorsen, Todd et al., "Dynamic Pattern Formation In A Vesicle-Generating Microfluidic Device," Physical Review Letters, vol. 86, No. 18, pp. 4163-4166, Apr. 30, 2001.

Thorsen, Todd et al., "Microfluidic Large-Scale Integration," Science, vol. 298, No. 5593, pp. 580-584, Oct. 18, 2002.

Tufte, O. N. et al., "Silicon Diffused-Element Piezoresistive Diaphragms," Journal of Applied Physics, vol. 33, No. 11, pp. 3322-3327, Nov. 1962.

Ullmann's Encyclopedia of Industrial Chemistry, Sections 6 to 6.3, Topic: Carbon Black, Sixth Edition, 7 pages, 1999.

Unger, Marc A. et al., "Monolithic Microfabricated Valves And Pumps By Multilayer Soft Lithography," Science, vol. 288, pp. 113-116, Apr. 7, 2000.

Unger, Marc A. et al., "Single-Molecule Fluorescence Observed With Mercury Lamp Illumination," Biotechniques, vol. 27, No. 5, pp. 1008-1014, Nov. 1999.

Van De Pol, F.C.M. et al., "A Thermo-Pneumatic Actuation Principle For A Microminiature Pump And Other Micromechanical Devices," Sensors and Actuators, vol. 17, Nos. 1-2, pp. 139-143, May 3, 1989.

Van De Pol, F.C.M. et al., "Micro Liquid Handling Devices—A Review," Micro Systems Technologies, vol. 90, pp. 799-805, 1990.

Van Den Berg, A. et al., "Micro Total Analysis Systems," Proceedings of the μTAS '94 Workshop, University of Twente, The Netherlands, 17 pages, Nov. 21-22, 1994.

Van Der Woerd, Mark et al., "Lab-On-A-Chip Based Protein Crystallization," National Aeronautics and Space Administration and Caliper, pp. 1-27, Oct. 25, 2001.

Van Der Woerd, Mark et al., "The Promise Of Macromolecular Crystallization In Microfluidic Chips," Journal of Structural Biology, vol. 142, pp. 180-187, 2003.

Velev, Orlin D., "On-Chip Manipulation Of Free Droplets," Nature, vol. 426, pp. 515-516, Dec. 4, 2003.

Verpoorte, Elisabeth M. J. et al., "Three-Dimensional Micro Flow Manifolds For Miniaturized Chemical Analysis Systems," J. Micromech. Microeng., vol. 7, pp. 246-256, 1994.

Vieider, Christian et al., "A Pneumatically Actuated Micro Valve With A Silicon Rubber Membrane For Integration With Fluid Handling Systems," Transducers '95, 8th International Conference on Solid-State Sensors and Actuators and Eurosensors IX, Stockholm, Sweden, pp. 284-286, Jun. 25-29, 1995.

Vogelstein, Bert et al., "Digital PCR," Proc. Natl. Acad. Sci. USA, vol. 96, pp. 9236-9241, Aug. 1999.

Washizu, Masao et al., "Molecular Dielectrophoresis Of Biopolymers," IEEE Transactions on Industry Applications, vol. 30, No. 4, pp. 835-843, Jul. 1994.

Whelen, A. Christian et al., "The Role Of Nucleic Acid Amplification And Detection In The Clinical Microbiology Laboratory," Annu. Rev. Microbiol., vol. 50, pp. 349-373, 1996.

Whitesides, George M. et al., "Flexible Methods For Microfluidics," Physics Today, pp. 42-48, Jun. 2001.

Whitesides, George M. et al., "Soft Lithography In Biology And Biochemistry," Annu. Rev. Biomed. Eng., vol. 3, pp. 335-373, 2001.

Wilbur, James L. et al., "Lithographic Molding: A Convenient Route To Structures With Sub-Micrometer Dimensions," Adv. Mater., vol. 7, No. 7, pp. 649-652, 1995.

Wilm, Matthias et al., "Femtomole Sequencing Of Proteins From Polyacrylamide Gels By Nano-Electrospray Mass Spectrometry," Nature, vol. 379, pp. 466-469, Feb. 1, 1996.

Wu, Hongkai et al., "Fabrication Of Complex Three-Dimensional Microchannel Systems In PDMS," J. Am. Chem. Soc., vol. 125, No. 2, pp. 554-559, 2003.

Xia, Younan et al., "Complex Optical Surfaces Formed By Replica Molding Against Elastomeric Masters," Science, vol. 273, pp. 347-349, Jul. 19, 1996.

Xia, Younan et al., "Micromolding Of Polymers In Capillaries: Applications In Microfabrication," Chem. Mater., vol. 8, No. 7, pp. 1559-1566, 1996.

Xia, Younan et al., "Reduction In The Size Of Features Of Patterned SAMs Generated By Microcontact Printing With Mechanical Compression Of The Stamp," Adv. Mater., vol. 7, No. 5, pp. 471-473, 1995.

Xia, Younan et al., "Soft Lithography," Angew. Chem. Int. Ed., vol. 37, pp. 551-575, 1998.

Xu, Bing et al., "Making Negative Poisson's Ratio Microstructures By Soft Lithography," Adv. Mater., vol. 11, No. 14, pp. 1186-1189, 1999.

Xu, Jingdong et al., "Room-Temperature Imprinting Method For Plastic Microchannel Fabrication," Analytical Chemistry, vol. 72, No. 8, pp. 1930-1933, Apr. 15, 2000.

Xue, Qifeng et al., "Integrated Multichannel Microchip Electrospray Ionization Mass Spectrometry: Analysis Of Peptides From On-Chip Tryptic Digestion of Melittin," Rapid Communications In Mass Spectrometry, vol. 11, 1253-1256, 1997.

Xue, Qifeng et al., "Multichannel Microchip Electrospray Mass Spectrometry," Analytical Chemistry, vol. 69, No. 3, pp. 426-430, Feb. 1, 1997.

Yang, T. J. et al., "An Apertureless Near-Field Microscope For Fluorescence Imaging," Applied Physics Letters, vol. 76, No. 3, pp. 378-380, Jan. 17, 2000.

Yang, Xing et al., "A Low Power MEMS Silicone/Parylene Valve," Solid-State Sensor and Actuator Workshop, Hilton Head Island, South Carolina, 4 pages, Jun. 7-11, 1998.

Yang, Xing et al., "A MEMS Thermopneumatic Silicone Membrane Valve," IEEE 10th Annual International Workshop of Micro Electro Mechanical Systems, Nagoya, Japan, pp. cover, 114-118, Jan. 26-30, 1997.

Yazdi, Navid et al., "Micromachined Inertial Sensors," Proceedings of IEEE, vol. 86, No. 8, pp. 1640-1659, Aug. 1998.

Young, A. M. et al., "Contoured Elastic-Membrane Microvalves For Microfluidic Network Integration," Journal of Biomechanical Engineering, vol. 121, pp. 2-6, Feb. 1999.

Zengerle, R. et al., "A Micro Membrane Pump With Electrostatic Actuation," Micro Electro Mechanical Systems '92, Travemünde, Germany, pp. 19-24, Feb. 4-7, 1992.

Zengerle, R. et al., "Performance Simulation Of Microminiaturized Membrane Pumps," 7th International Conference on Solid-State Sensors and Actuators, Yokohama, Japan, pp. 2 cover pages, 106-109, Jun. 7-10, 1993.

Zhang, B. et al., "Microfabricated Devices For Capillary Electrophoresis-Electrospray Mass Spectrometry," Analytical Chemistry, vol. 71, No. 15, pp. 3258-3264, Aug. 1, 1999.

Zhao, Zhan, et al., "An Integrated Biochip Design And Fabrication," Proceedings of SPIE, vol. 4936, pp. 321-326, 2002.

Zheng, Bo et al., "A Droplet-Based, Composite PDMS/Glass Capillary Microfluidic System For Evaluating Protein Crystallization Conditions By Microbatch And Vapor-Diffusion Methods With On-Chip X-Ray Diffraction," Angew. Chem., pp. 1-4, 2004.

Affholter, Joseph et al., "Engineered A Revolution," Chemistry in Britain, pp. 48-51, Apr. 1999.

Arnold, Frances H., "Design By Directed Evolution," Accounts of Chemical Research, vol. 31, No. 3, pp. 125-131, 1998.

Ashkin, A. et al., "Optical Trapping And Manipulation Of Single Cells Using Infrared Laser Beams," Nature, vol. 330, No. 24, pp. 769-771, Dec. 31, 1987.

Askin, A. et al., "Optical Trapping And Manipulation Of Viruses And Bacteria," Science, vol. 235, pp. 1517-1520, Mar. 20, 1987.

Barron, Annelise E. et al., "Capillary Electrophoresis Of DNA In Uncross-Linked Polymer Solutions," Journal of Chromatography A, vol. 652, pp. 3-16, 1993.

Barron, Annelise E. et al., "DNA Separations By Slab Gel And Capillary Electrophoresis—Theory And Practice," Separation and Purification Methods, vol. 24, No. 1, pp. 1-118, 1995.

Barron, Annelise E. et al., "The Use Of Coated And Uncoated Capillaries For The Electrophoretic Separation Of DNA In Dilute Polymer-Solutions," Electrophoresis, vol. 16, pp. 64-74, 1995.

Blanch, Harvey W. et al., Biochemical Engineering, pp. 2 cover pages and 305, 1996.

Blankenstein, Gert et al., "Modular Concept Of A Laboratory On A Chip For Chemical And Biochemical Analysis," Biosensors & Bioelectronics, vol. 13, Nos. 3-4, pp. 427-438, 1998.

Budowle, Bruce et al., "Analysis Of The VNTR Locus DIS80 By The PCR Followed By High-Resolution PAGE," Am. J. Hum. Genet., vol. 48, pp. 137-144, 1991.

Buican, Tudor N. et al., "Automated Single-Cell Manipulation And Sorting By Light Trapping," Applied Optics, vol. 26, No. 24, pp. 5311-5316, Dec. 15, 1987.

Busch, J. et al., Methods For The Differentiation Of Microorganisms, Journal of Chromatography B, vol. 722, pp. 263-278, 1999.

Chou, Hou-Pu et al., "Disposable Microdevices For DNA Analysis And Cell Sorting," Proc. Solid-State Sensor and Actuator Workshop, Hilton Head, South Carolina, pp. 11-14, Jun. 8-11, 1998.

Chou, Hou-Pu et al., "Microfabricated Devices For Sizing DNA And Sorting Cells," Micro- and Nanofabricated Structures and Devices for Biomedical Environmental Applications, Proceedings of SPIE, vol. 3258, pp. 181-187, 1998.

Costerton, J. William et al., "Microbial Biofilms," Annu. Rev. Microbiol., vol. 49, pp. 711-745, 1995.

Cowen, S. et al., "An On-Chip Miniature Liquid Chromatography System: Design, Construction And Characterization," Micro Total Analysis Systems, Proceedings of the μTAS '94 Workshop, University of Twente, The Netherlands, pp. 2 cover pages and 295-298, 1995.

Crosland-Taylor, P. J., "A Device For Counting Small Particles Suspended In A Fluid Through A Tube," Nature, vol. 171, pp. 37-38, Jan. 3, 1953.

Delisa, Matthew P. et al., "Mapping Stress-Induced Changes In Autoinducer Al-2 Production In Chemostat-Cultivated *Escherichi coli* K-12," Journal of Bacteriology, vol. 183, No. 9, pp. 2918-2928, May 2001.

Effenhauser, Carlo S. et al., "Miniaturizing A Whole Analytical Laboratory Down To Chip Size," American Laboratory, vol. 26, No. 14, pp. cover, 15, 16, 18, 1994.

Effenhauser, Carlo S., "Integrated Chip-Based Microcolumn Separation Systems," Topics in Current Chemistry, vol. 194, pp. cover, 52-82, 1998.

Felix, Arthur M. et al., "Pegylated Peptides IV—Enhanced Biological Activity Of Site-Directed Pegylated GRF Analogs," International Journal of Peptide & Protein Research, vol. 46, pp. 253-264, 1995.

Felix, Arthur M., "Site-Specific Poly(ethylene glycol)ylation Of Peptides," Poly(Ethylene Glycol) Chemistry and Biological Applications, ACS Symposium Series 680, pp. 2 cover pages, 218-238, 1997.

Fiedler, Stefan et al., "Dielectrophoretic Sorting Of Particles And Cells In A Microsystem," Analytical Chemistry, vol. 70, No. 9, pp. 1909-1915, May 1, 1998.

Fu, Anne Y. et al., "An Integrated Microfabricated Cell Sorter," Analytical Chemistry, vol. 74, No. 11, pp. 2451-2457, Jun. 1, 2002.

Fulwyler, M. J., "Electronic Separation Of Biological Cells By Volume," Science, pp. 910-911, Nov. 1965.

Geng, Xindu et al., "Retention Model For Proteins In Reversed-Phase Liquid Chromatography," Journal of Chromatography, vol. 296, pp. 15-30, 1984.

Ginsberg, Michael A., "New Laser System Measure DNA Fragments," Biophotonics International, p. 20, Nov./Dec. 1996.

Giusti, Alan et al., "Application Of Deoxyribonucleic Acid (DNA) Polymorphisms To The Analysis Of DNA Recovered From Sperm," Journal of Forensic Sciences, vol. 31, No. 2, pp. 409-417, Apr. 1986.

Gombotz, W. R. et al., "Pegylation: A Tool To Enhance Protein Delivery," Abstracts of Papers, American Chemical Society, vol. 217, Part 2, 2 pages, Mar. 21-25, 1999.

Gonzalez, Jesus E. et al., "Improved Indicators Of Cell Membrane Potential That Use Fluorescence Resonance Energy Transfer," Chemistry & Biology. vol. 4, No. 4, pp. 269-277, Apr. 1997.

Goodwin, Peter M. et al., "Rapid Sizing Of Individual Fluorescently Stained DNA Fragments By Flow Cytometry," Nucleic Acids Research, vol. 21, No. 4, pp. 803-806, 1993.

Guerra, Patricia I. et al., "PEGylation Prevents The N-Terminal Degradation Of Megakaryocyte Growth And Development Factor," Pharmaceutical Research, vol. 15, No. 12, pp. 1822-1827, 1998.

Hancock, Robert E. W., "A Brief On Bacterial Biofilms," Nature Genetics, vol. 29, p. 360, Dec. 2001.

Hanes, Jozef, et al., "In Vitro Selection And Evolution Of Functional Proteins By Using Ribosome Display," Proc. Natl. Acad. Sci. USA, vol. 94, pp. 4937-4942, May 1997.

Harrison, D. Jed et al., "Integration Of Analytical Systems Incorporating Chemical Reactions And Electrophoretic Separation," Micro Total Analysis Systems, Proceedings of the μTAS '94 Workshop, University of Twente, The Netherlands, pp. 2 cover pages and 105-111, 1995.

Heo, Jinseok et al., "A Microfluidic Bioreactor Based On Hydrogel-Entrapped E. coli: Cell Viability, Lysis, And Intracellular Enzyme Reactions," Analytical Chemistry, vol. 75, No. 1, pp. 22-26, Jan. 1, 2003.

Herbert, D. et al., "The Continuous Culture Of Bacteria; A Theoretical And Experimental Study," J. Gen. Microbiol., vol. 14, pp. 601-622, 1956.

Herbert, D., "Continous Culture Of Bacteria," The Journal of General Microbiology, vol. 15, pp. 2 cover pages and iv, 1956.

Herbert, D., "Continuous Culture Of Bacteria: Principles And Applications," Chemistry and Industry, pp. 381, Mar. 29, 1958.

Hermanson, Greg T. et al., "Chapter 2—Activation Methods," Immobilized Affinity Ligand Techniques, Academic Press, pp. 2 cover pages, 51-136, 1992.

Hoffmuller, Ulrich et al., "In Vitro Evolution And Selection Of Proteins: Ribosome Display For Larger Libraries," Angew. Chem. Int. Ed., vol. 37, No. 23, pp. 3241-3243, 1998.

Ingraham, John L. et al., Growth Of The Bacterial Cell, pp. 3 cover pages and 230, 1983.

Jacobsen, Ken et al., "International Workshop On The Application Of Fluorescence Photobleaching Techniques To Problems In Cell Biology," Federation Proceedings, vol. 42, No. 1, pp. 72-79, Jan. 1983.

Jacobson, Stephen C. et al., "Open Channel Electrochromatography On A Microchip," Analytical Chemistry, vol. 66, No. 14, pp. 2369-2373, Jul. 15, 1994.

Jannasch, H. W. et al., "Experimental Bacterial Ecology Studied In Continuous Culture," Advances in Microbial Physiology, vol. 11, pp. cover and 165-212, 1974.

Jeffreys, Alec J. et al., "Hypervariable 'Minisatellite' Regions In Human DNA," Nature, vol. 314, pp. 67-73, Mar. 7, 1985.

Jermutus, Lutz, et al., "Recent Advances In Producing And Selecting Functional Proteins By Using Cell-Free Translation," Current Opinion in Biotechnology, vol. 9, pp. 534-548, 1998.

Ju, Li-Ya et al., "Application Of Silver Staining To The Rapid Typing Of The Polymorphism of HLA-DQ Alleles By Enzymatic Amplification and Allele-Specific Restriction Fragment Length Polymorphism," Electrophoresis, vol. 12, pp. 270-273, 1991.

Juárez-Martinez, G. et al., "High-Throughput Screens For Postgenomics: Studies Of Protein Crystallization Using Microsystems Technology," Analytical Chemistry, vol. 74, No. 14, pp. 3505-3510, Jul. 15, 2002.

Kamentsky, Louis A. et al., "Spectrophotometer: New Instrument For Ultrarapid Cell Analysis," Science, vol. 150, pp. 630-631, Oct. 29, 1965.

Kanter, Evan et al., "Analysis Of Restriction Fragment Length Polymorphisms In Deoxyribonucleic Acid (DNA) Recovered From Dried Bloodstains," Journal of Forensic Sciences, vol. 31, No. 2, pp. 403-408, Apr. 1986.

Kodera, Yoh et al., "Pegylation Of Proteins And Bioactive Substances For Medical And Technical Applications," Prog. Polym. Sci., vol. 23, pp. 1233-1271, 1998.

Lane, P. G., "Analysis Of A Continuous-Culture Technique For The Selection Of Mutants Tolerant To Extreme Environmental Stress," Biotechnology and Bioengineering, vol. 65, No. 4, pp. 397-406, Nov. 20, 1999.

Lawrence, J. R. et al., "Optical Sectioning Of Microbial Biofilms," Journal of Bacteriology, vol. 173, No. 20, pp. 6558-6567, Oct. 1991.

Lee, L. Stanford et al., "Prolonged Circulating Lives Of Single-Chain Fv Proteins Conjugated With Polyethylene Glycol: A Comparison Of Conjugation Chemistries And Compounds," Bioconjugate Chem., vol. 10, pp. 973-981, 1999.

Levine, Leanna M. et al., "Measurement Of Specific Protease Activity Utilizing Fluorescence Polarization," Analytical Biochemistry, vol. 247, pp. 83-88, 1997.

Llopis, Juan et al., "Ligand-Dependent Interactions Of Coactivations Steroid Receptor Coactivator-1 And Peroxisome Proliferator-Activated Receptor Binding Protein With Nuclear Hormone Receptors Can Be Imaged In Live Cells And Are Required For Transcription," PNAS, vol. 97, No. 8, pp. 4363-4368, Apr. 11, 2000.

Marešová, H. et al., "A Chemistat Culture As A Tool For The Improvement Of A Recombinant E. coli Strain Over-Producing Penicillin G Acylase," Biotechnology And Bioengineering, vol. 75, No. 1, pp. 46-52, Oct. 5, 2001.

Mason, T. G. et al., "Shear Rupturing Of Droplets In Complex Fluids," Langmuir, vol. 13, pp. 4600-4613, 1997.

Mastrangelo, C. H. et al., "Vacuum-Sealed Silicon Micromachined Incandescent Light Source," IEDM, pp. 503-506, 1989.

Maule, John, "Pulsed-Field Gel Electrophoresis," Molecular Biotechnology, vol. 9, pp. 107-126, 1998.

Menchen, Steve et al., "Flowable Networks As DNA Sequencing Media In Capillary Columns," Electrophoresis, vol. 17, pp. 1451-1459, 1996.

Moldavan, Andrew, "Photo-Electric Technique For The Counting Of Microscopical Cells," Science, vol. 80, No. 2069, pp. 188-189, Aug. 24, 1934.

Monod, Jacques, "The Growth Of Bacterial Cultures," Annual Review of Microbiology, vol. III, pp. cover and 371-394, 1949.

Murray, Vincent et al., "Detection Of Polymorphisms Using Thermal Cycling With A Single Oligonucleotide On A DNA Sequencing Gel," Human Mutation, vol. 2, pp. 118-122, 1993.

Nagai, Yasuo et al., "A Fluorescent Indicator For Visualizing cAMP-Induced Phosphorylation In Vivo," Nature Biotechnology, vol. 18, pp. 313-316, Mar. 2000.

Nakamura, Yusuke et al., "Variable Number Of Tanden Repeat (VNTR) Markers For Human Gene Mapping," Science, vol. 235, pp. 1616-1622, Mar. 27, 1987.

Nielsen, Jens et al., Bioreaction Engineering Principles, Second Edition, pp. 2 cover pages and 42-45, 2003.

Novick, Aaron et al., "Description Of The Chemostat," Science, vol. 112, pp. 715-716, Dec. 15, 1950.

Novick, Aaron et al., "Experiments With The Chemostat On Spontaneous Mutations Of Bacteria," Proc. N. A. S., vol. 36, pp. 708-719, 1950.

O'Reilly, Marie-Anne J. et al., "The Technique Of Pulsed Field Gel Electrophoresis And Its Impact On Mulecular Immunology," Journal of Immunological Methods, vol. 131, pp. 1-13, 1990.

Parker, Gregory J. et al., "Development Of High Throughput Screening Assays Using Fluorescence Polarization: Nuclear Receptor-Ligand-Binding And Kinase/Phophatase Assays," Journal of Biomolecular Screening, vol. 5, No. 2, pp. 77-88, 2000.

Petty, Jeffrey T. et al., "Characterization Of DNA Size Determination Of Small Fragments By Flow Cytometry," Anal. Chem., vol. 67, pp. 1755-1761, 1995.

Poplawski, M. E. et al., "A Simple Packaging Process For Chemical Sensors," Solid-State Sensor and Actuator Workshop, Hilton Head, South Carolina, pp. 25-28, Jun. 13-16, 1994.

Qu, Mingbo et al., "Toxicity And Biodegradation Of Formaldehyde In Anaerobic Methanogenic Culture," Biotechnology and Bioengineering, vol. 55, No. 5, pp. 727-736, Sep. 5, 1997.

Roberts, Richard W. et al., "RNA-Peptide Fusions For The In Vitro Selection Of Peptides And Proteins," Proc. Natl. Acad. Sci. USA, vol. 94, pp. 12297-12302, Nov. 1997.

Rotman, Boris, "A Simplified Device For Continuouos Growth Of Microorganisms," Journal of Bacteriology, vol. 70, pp. 485-486, 1955.

Rouhi, Maureen, "Sizing, Sorting DNA One Piece At A Time," C&EN, pp. 5-6, Jan. 11, 1999.

Seethala, Ramakrishna et al., "A Fluorescence Polarization Competition Immunoassay For Tyrosine Kinases," Analytical Biochemistry, vol. 255, pp. 257-262, 1998.

Shuler, Michael L. et al., "Chapter 6—How Cell Grow," Bioprocess Basic Concepts, Second Edition, pp. 2 cover pages and 155-200, 2002.

Sklar, Larry A. et al., Sample Handling For Kinetics And Molecular Assembly In Flow Cytometry, SPIE, vol. 3256, pp. 144-153, 1998.

Spicer, C. C., "The Theory Of Bacterial Constant Growth Apparatus," Biometrics, pp. 225-230, Jun. 1955.

Stemmer, Willem P. C. et al., "Rapid Evolution Of A Protein in vitro By DNA Shuffling," Nature, vol. 370, pp. 389-390, Aug. 4, 1994.

Swart, Remco et al., "Recent Progress In Open Tubular Liquid Chromatography," Trends in Analytical Chemistry, vol. 16, No. 6, pp. 332-342, 1997.

Sweet, Richard G., "Chapter 9—Flow Sorters For Biologic Cells," Flow Cytometry and Sorting, John Wiley & Sons, pp. 5 cover pages and 177-189, 1979.

Takahashi, Akiyuki et al., "Measurement Of Intracellular Calcium," Physiological Reviews, vol. 79, No. 4, pp. 1089-1125, Oct. 1999.

Tatari, Zohreh et al., "HLA-Cw Allele Analysis By PCR-Restriction Fragment Length Polymorphism: Study Of Known And Additional Alleies," Proc. Natl. Acad. Sci. USA, vol. 92, pp. 8803-8807, Sep. 1995.

Tawfik, Dan S. et al., "Man-Made Cell-Like Compartments For Molecular Evolution," Nature Biotechnology, vol. 16, pp. 652-656, Jul. 1998.

Taylor, Anne M. et al., "Microfluidic Multicompartment Device For Neuroscience Research," Langmuir, vol. 19, pp. 1551-1556, 2003.

Terry, Stephen C. et al., "A Gas Chromatographic Air Analyzer Fabricated On A Silicon Wafer," IEEE Transactions on Electron Devices, vol. ED-26, No. 12, pp. 1880-1886, Dec. 1979.

Todd, Paul et al., "Chapter 12—Cell Electrophoresis," Flow Cytometry and Sorting, John Wiley & Sons, pp. 5 cover pages and 217-229, 1979.

Umdanhowar, P. B. et al., "Monodisperse Emulsion Generation Via Drop Break Off In A Coflowing Stream," Langmuir, vol. 16, pp. 347-351, 2000.

Vahey, Paul G. et al., "Development Of A Positive Pressure Driven Micro-Fabricated Liquid Chromatographic Analyzer Through Rapid-Prototyping With Poly(dimethylsiloxane) Optimizing Chromatographic Effiency With Sub-Nanoliter Injections," Talanta, vol. 51, pp. 1205-1212, 2000.

Van Dilla, M. A. et al., "Cell Microfluorometry: A Method For Rapid Fluorescence Measurement," Science, vol. 163, pp. 1213-1214, Mar. 14, 1969.

Van Dilla, Marvin A. et al., "Chapter 2—Introduction And Resume Of Flow Cytometry And Sorting," Flow Cytometry and Sorting, John Wiley & Sonos, pp. 5 cover pages and 11-37, 1979.

Veronese, F. M. et al., "Influence Of PEGylation On The Release Of Low And High Molecular-Weight Proteins From PVA Matrices," Journal of Bioactive and Compatible Polymers, vol. 14, pp. 315-330, Jul. 1999.

Veronese, Francesco M., "Peptide And Protein PEGylation: A Review Of Problems And Solutions," Biomaterials, vol. 22, pp. 405-417, 2001.

Volkmuth, W. D. et al., "DNA Electrodiffusion In A 2D Array Of Posts," Physical Review Letters, vol. 72, No. 13, pp. 2117-2120, Mar. 28, 1994.

Volkmuth, W. D. et al., "DNA Electrophoresis In Microlithographic Arrays," Nature, vol. 358, pp. 600-602, Aug. 13, 1992.

Ward, Keith B. et al., "Automatic Preparation Of Protein Crystals Using Laboratory Robotics And Automated Visual Inspection," Journal of Crystal Growth, vol. 90, pp. 325-339, 1988.

Weigl, Bernhard H., "Microfluidics-Based Lab-On-A-Chip Systems," IVD Technology Magazine, 8 pages, Nov./Dec. 2000.

Wiebe, Marilyn G. et al., "Evolution Of A Recombinant (Gucoamylase-Producing) Strain Of Fusarium venenatum A3/5 In Chemostat Culture," Biotechnology and Bioengineering, vol. 73, No. 2, pp. 146-156, Apr. 20, 2001.

Wu, Chunhung et al., "Viscosity-Adjustable Block Copolymer For DNA Separation By Capillary Electrophoresis," Electrophoresis, vol. 19, pp. 231-241, 1998.

Xu, Xiang et al., "Detection Of Programmed Cell Death Using Fluorescence Energy Transfer," Nucleic Acids Research, vol. 26, No. 8, pp. 2034-2035, 1998.

Yokobayashi, Yohei et al., "Evolutionary Design Of Genetic Circuits And Cell-Cell Communications," Advances in Complex Systems, vol. 6, No. 1, pp. 37-45, 2003.

Zaccolo, Manuela et al., "A Genetically Encoded, Fluorescent Indicator For Cyclic AMP In Living Cells," Nature Cell Biology, vol. 2, pp. 25-29, Jan. 2000.

Zalipsky, Samuel, "Chemistry Of Polyethylene Glycol Conjugates With Biologically Active Molecules," Advanced Drug Delivery Reviews, vol. 16, pp. 157-182, 1995.

Zdeblick, Mark J. et al., "A Microminiature Electric-To-Fluidic Valve," Transducers '87, Proceedings of the 4th International Conference on Solid-State Sensors and Actuators, reprinted in Micromachinics and MEMS Classic and Seminal Papers to 1990, pp. 2 cover pages, 437-439, Jun. 1987.

* cited by examiner

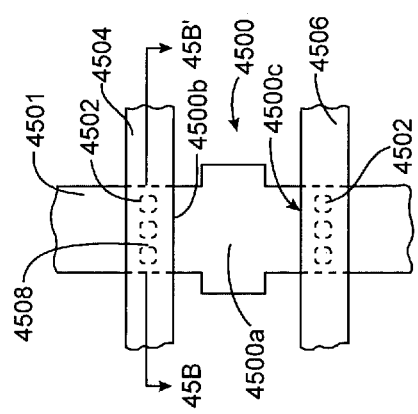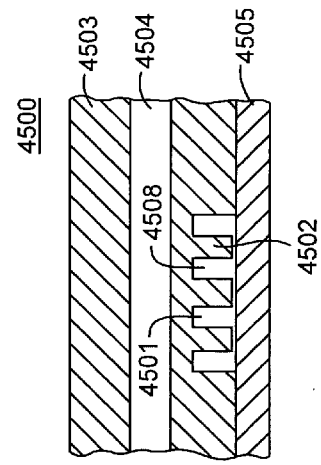
FIG. 19A
FIG. 19B

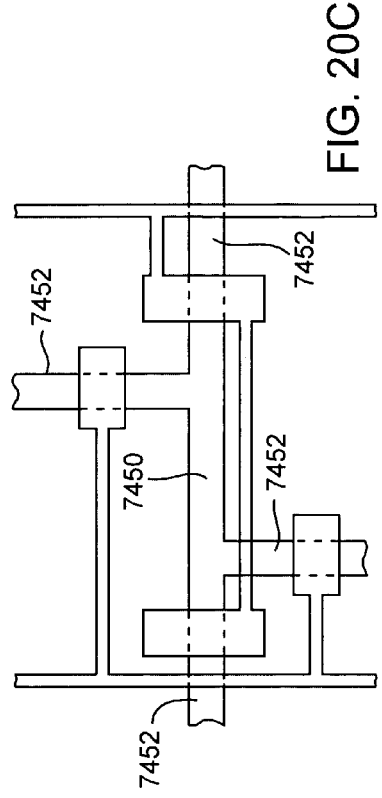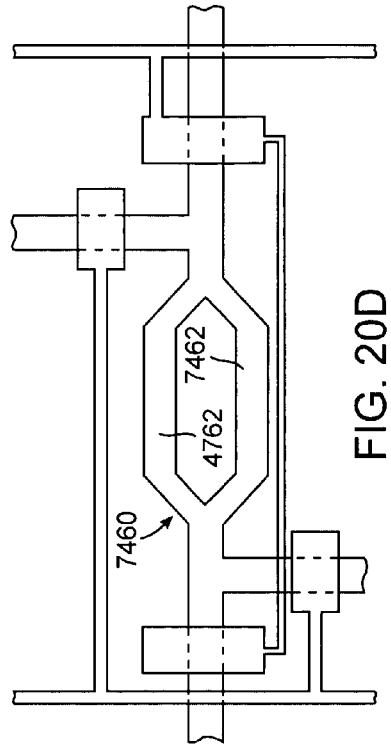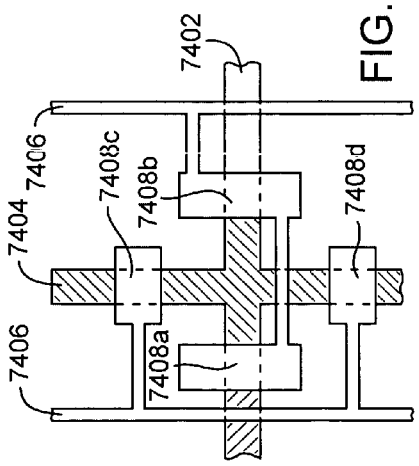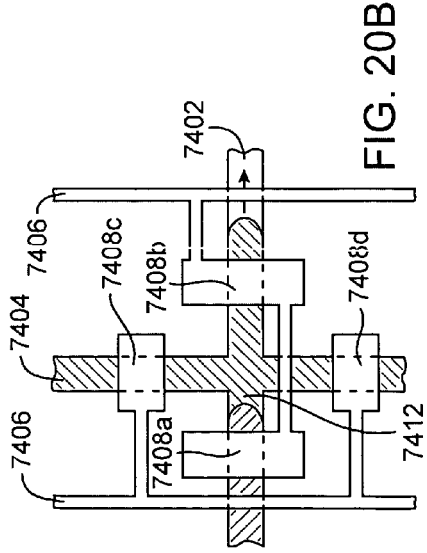

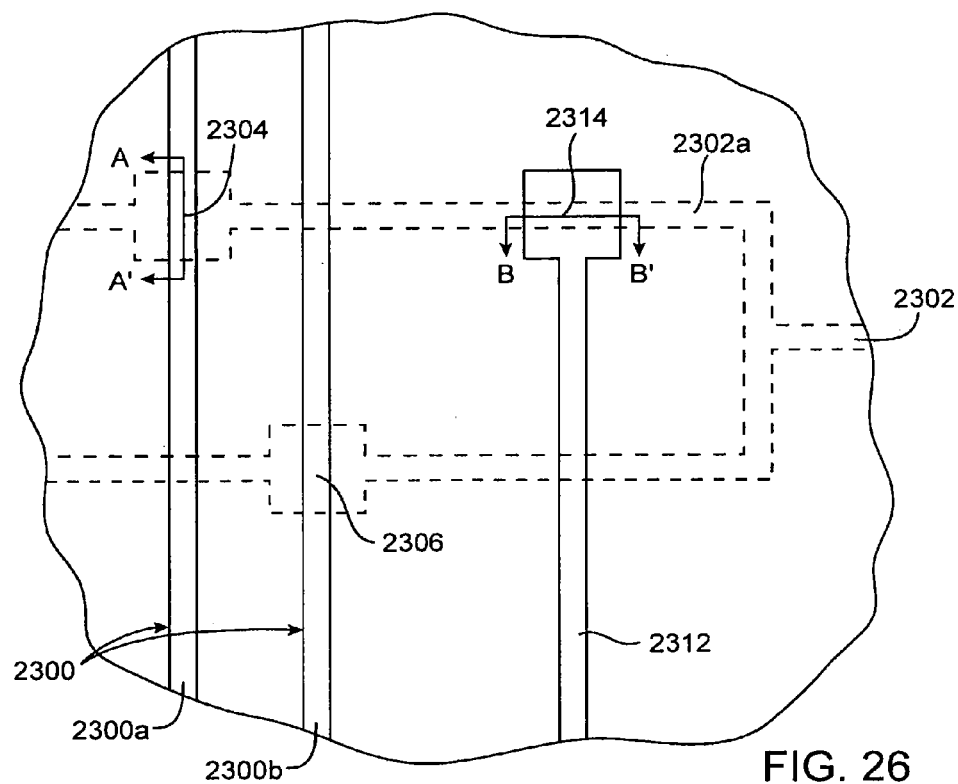
FIG. 26A
FIG. 26B

MICROFLUIDIC ROTARY FLOW REACTOR MATRIX

CROSS-REFERENCE TO RELATED APPLICATIONS

The instant nonprovisional patent application claims priority from U.S. provisional patent application No. 60/494,432, filed Aug. 11, 2003. This previously filed provisional patent application is hereby incorporated by reference for all purposes.

STATEMENT AS TO RIGHTS TO INVENTIONS MADE UNDER FEDERALLY SPONSORED RESEARCH AND DEVELOPMENT

Work described herein has been supported, in part, by DARPA Grant No. DAAD19-00-1-0392 and National Science Foundation Grant No. CTS-0088649. The United States Government may have certain rights in the invention.

BACKGROUND OF THE INVENTION

As described by at least Mitchell in *Nat. Biotechnol.* 19, 717-721 (2001), incorporated by reference herein for all purposes, microfluidic technology offers many possible benefits in chemistry, biology and medicine. One important possible benefit is to automate rote work while reducing the consumption of expensive reagents to the nanoliter or sub-nanoliter scale.

As described in *Anal. Chem.* 69, 3407-3412 (1997), incorporated by reference herein for all purposes, Hadd et al. developed a microchip for performing automated enzyme assay, in which precise concentrations of substrate, enzyme, and inhibitor were mixed in nanoliter volumes using electrokinetic flow. In *Anal. Chem.* 74, 2451-2457 (2002), incorporated by reference herein for all purposes, Fu et al reported an integrated cell sorter with a 1 picoliter minimum active volume by the actuated valve.

However, as pointed out by Meldrum et al. in *Science* 297, 1197-1198 (2002), incorporated by reference herein for all purposes, since microfluidic devices must at some point be interfaced to the macroscopic world, there is a minimum practical volume (of order—1 µl) that can be introduced into a device. The so-called "world-to-chip" interface problem described by Ramsey in *Nat. Biotechnol.* 17, 1061-1062 (1999), incorporated by reference herein for all purposes, has plagued the microfluidic field since its inception. As noted by Ross et al. in *Anal. Chem.* 74, 2556-2564 (2002), it is always questionable how the desired economies of scale in microfluidics can practically be achieved, unless an effective approach is developed to solve the mismatch between those two scales.

Although integrated glass capillaries have been used to reduce sample consumption for simple titration between two reagents, these devices are fundamentally serial and have the possibility of sample cross-contamination during the loading process. See Farinas et al., *Analytical Biochemistry* 295, 138-142 (2001), incorporated by reference herein for all purposes.

On the other hand, there has been an effort to develop techniques to concentrate analytes from a large input volume. In *Anal. Chem.* 73, 1627-1633 (2001), incorporated by reference herein for all purposes, Macounova et al. describe microfluidic isoelectric focusing (IEF) techniques. Ross et al. describe temperature gradient focusing (TGF) techniques. However, only a limited species of samples have successfully been demonstrated so far.

The challenge associated with realizing the desired economies of scale in microfluidic devices is to simultaneously reduce the number of pipetting steps needed to load the devices, while amortizing the sample volume from each pipetting step over a large number of independent assays. As pointed out in U.S. Pat. No. 6,508,988, incorporated by reference herein for all purposes, microfluidic matrix geometries offer the advantage of performing $N^2$ independent reactions with only 2N pipetting steps.

In *Lab on a Chip* 2, 188-192 (2002), Kikutani et al. used N=2 matrices for chemical synthesis. In *Anal. Chem.*, 73, 5207-5213 (2001), Ismagilov et al. used N=5 passive matrices to demonstrate two-component biochemical assays such as optical detection of enzymatic activity. However, in those devices the reagent consumption scaled only with N, which was so small that there were little practical savings.

Passive devices also have technical limitations in sample metering and device operation. For example, precise pressure balancing was required during operation of the devices of Kikutani et al., and the kinetics of mixing were limited due to the static nature in the devices of Ismagilov et al.

Accordingly, there is a need in the art for microfluidic techniques and apparatuses for addressing the "world-to-chip" interface problem.

SUMMARY OF THE INVENTION

An embodiment of a microfluidic matrix device in accordance with the present invention offers an effective solution to the "world-to-chip" interface problem by accomplishing two important goals simultaneously: an economy of scale in reagent consumption is achieved, while simultaneously minimizing pipetting steps. $N^2$ independent assays can be performed with only 2N+1 pipetting steps, using a single aliquot of the enzyme that can be amortized over all the reactors. Thus, the chip reduces labor relative to conventional fluid handling techniques by using an order of magnitude less pipetting steps and reduces cost by consuming two to three orders of magnitude less reagents per reaction. The demonstrated PCR format has immediate applications in medical diagnosis and gene testing. Beyond PCR, the microfluidic matrix chip provides a universal and flexible platform for biological and chemical assays that require parsimonious use of precious reagents and highly automated processing.

An embodiment of a microfluidic device in accordance with the present invention, comprises, a plurality of flow channels defined within an elastomer layer to form a matrix of rotary flow reactors. A first set of control lines are proximate to and separated from the flow channels by first elastomer membranes, the first elastomer membranes actuable to introduce fluids into the rotary flow reactors and to isolate the rotary flow reactors. A second set of control lines are proximate to and separated from the flow channels by second elastomer membranes, the second elastomer membranes actuable to cause peristaltic pumping of the fluids within the isolated rotary flow reactors.

A method of conducting a chemical reaction, the method comprising, providing a microfluidic device comprising a plurality of flow channels defined within an elastomer layer to form a matrix of rotary flow reactors, a first set of control lines proximate to and separated from the flow channels by first elastomer membranes, and a second set of control lines proximate to and separated from the flow channels by second elastomer membranes. First and second chemicals are introduced to the rotary flow reactors. Pressure is applied to the first set of control lines to actuate the first elastomer membranes to isolate the rotary flow reactors, and pressure is applied to the second set of control lines to actuate the second elastomer membranes to cause peristaltic pumping of the fluids within the isolated rotary flow reactors.

These and other embodiments of the present invention, as well as its advantages and features, are described in more detail in conjunction with the text below and attached figures.

BRIEF DESCRIPTION OF THE DRAWINGS

FIGS. 19A-19B show plan and cross-sectional views illustrating operation of one embodiment of a cell cage structure in accordance with the present invention.

FIGS. 20A-20D show plan views of operation of a structure utilizing cross-channel injection in accordance with the embodiment of the present invention.

FIG. 26 shows a simplified plan view of an alternative embodiment of a microfluidic structure utilizing control channels to control other control channels.

FIG. 26A shows a simplified cross-sectional view of the structure of FIG. 26 taken along the line A-A'.

FIG. 26B shows a simplified cross-sectional view of the structure of FIG. 26 taken along the line B-B'.

FIG. 30 shows a two-color image of fluorescent emission from a 20×20 matrix chip.

FIG. 31 shows a scanned fluorescent image illustrating use of the matrix chip to explore combinations of forward and reverse primers.

FIGS. 36A-D are simplified plan views showing operation of an alternative embodiment of a microfluidic matrix architecture in accordance with the present invention.

DETAILED DESCRIPTION OF THE PRESENT INVENTION

Figure 1:
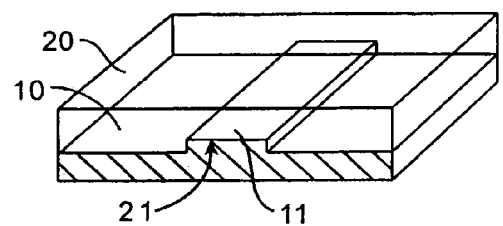
FIG. 1 is an illustration of a first elastomeric layer formed on top of a micromachined mold.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

A "flow channel" refers generally to a flow path through which a solution can flow.

The term "valve" unless otherwise indicted refers to a configuration in which a flow channel and a control channel intersect and are separated by an elastomeric membrane that can be deflected into or retracted from the flow channel in response to an actuation force.

The term "elastomer" and "elastomeric" has its general meaning as used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials can be characterized by a Young's modulus. The elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Some of the microfluidic devices described herein are fabricated from an elastomeric polymer such as GE RTV 615 (formulation), a vinyl-silane crosslinked (type) silicone elastomer (family). However, the present microfluidic systems are not limited to this one formulation, type or even this family of polymer; rather, nearly any elastomeric polymer is suitable. Given the tremendous diversity of polymer chemistries, precursors, synthetic methods, reaction conditions, and potential additives, there are a large number of possible elastomer systems that can be used to make monolithic elastomeric microvalves and pumps. The choice of materials typically depends upon the particular material properties (e.g., solvent resistance, stiffness, gas permeability, and/or temperature stability) required for the application being conducted. Additional details regarding the type of elastomeric materials that can be used in the manufacture of the components of the microfluidic devices disclosed herein are set forth in U.S. application Ser. No. 09/605,520, and PCT Application No. 00/17740, both of which are incorporated herein by reference in their entirety.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. The label attached to the probe can include any of a variety of different labels known in the art that can be detected by chemical or physical means, for example. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Probes can vary significantly in size. Some probes are relatively short. Generally, probes are at least 7 to 15 nucleotides in length. Other probes are at least 20, 30 or 40 nucleotides long. Still other probes are somewhat longer, being at least 50, 60, 70, 80, 90 nucleotides long. Yet other probes are longer still, and are at least 100, 150, 200 or more nucleotides long. Probes can be of any specific length that falls within the foregoing ranges as well.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes. The term "primer pair" means a set of primers including a 5' "upstream primer" that hybridizes with the complement of the 5' end of the DNA sequence to be amplified and a 3' "downstream primer" that hybridizes with the 3' end of the sequence to be amplified.

A primer that is "perfectly complementary" has a sequence fully complementary across the entire length of the primer and has no mismatches. The primer is typically perfectly complementary to a portion (subsequence) of a target sequence. A "mismatch" refers to a site at which the nucleotide in the primer and the nucleotide in the target nucleic acid with which it is aligned are not complementary. The term "substantially complementary" when used in reference to a primer means that a primer is not perfectly complementary to its target sequence; instead, the primer is only sufficiently complementary to hybridize selectively to its respective strand at the desired primer-binding site.

The term "complementary" means that one nucleic acid is identical to, or hybridizes selectively to, another nucleic acid molecule. Selectivity of hybridization exists when hybridization occurs that is more selective than total lack of specificity. Typically, selective hybridization will occur when there is at least about 55% identity over a stretch of at least 14-25 nucleotides, preferably at least 65%, more preferably at least 75%, and most preferably at least 90%. Preferably, one nucleic acid hybridizes specifically to the other nucleic acid. See M. Kanehisa, *Nucleic Acids Res.* 12:203 (1984).

The term "label" refers to a molecule or an aspect of a molecule that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, enzymes linked to nucleic acid probes and enzyme substrates. The term "detectably labeled" means that an agent has been conjugated with a label or that an agent has some inherent characteristic (e.g., size, shape or color) that allows it to be detected without having to be conjugated to a separate label.

I. Microfabrication Overview

The following discussion relates to formation of microfabricated fluidic devices utilizing elastomer materials, as described generally in U.S. patent application Ser. Nos. 10/118,466, filed Apr. 5, 2002, Ser. No. 10/265,473 filed Oct. 4, 2002, Ser. No. 10/118,466 filed Apr. 5, 2002, Ser. No. 09/826,585 filed Apr. 6, 2001, Ser. No. 09/724,784 filed Nov. 28, 2000, and Ser. No. 09/605,520, filed Jun. 27, 2000. These previously-filed patent applications are hereby incorporated by reference for all purposes.

1. Methods of Fabricating

Exemplary methods of fabricating the present invention are provided herein. It is to be understood that the present invention is not limited to fabrication by one or the other of these methods. Rather, other suitable methods of fabricating the present microstructures, including modifying the present methods, are also contemplated.

FIGS. 1 to 7B illustrate sequential steps of a first preferred method of fabricating the present microstructure, (which may be used as a pump or valve). FIGS. 8 to 18 illustrate sequential steps of a second preferred method of fabricating the present microstructure, (which also may be used as a pump or valve).

As will be explained, the preferred method of FIGS. 1 to 7B involves using pre-cured elastomer layers which are assembled and bonded. In an alternative method, each layer of elastomer may be cured "in place". In the following description "channel" refers to a recess in the elastomeric structure which can contain a flow of fluid or gas.

Referring to FIG. 1, a first micro-machined mold 10 is provided. Micro-machined mold 10 may be fabricated by a number of conventional silicon processing methods, including but not limited to photolithography, ion-milling, and electron beam lithography.

As can be seen, micro-machined mold 10 has a raised line or protrusion 11 extending therealong. A first elastomeric layer 20 is cast on top of mold 10 such that a first recess 21 will be formed in the bottom surface of elastomeric layer 20, (recess 21 corresponding in dimension to protrusion 11), as shown.

Figure 2:
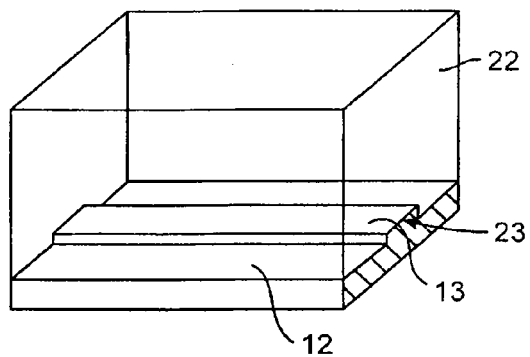
FIG. 2 is an illustration of a second elastomeric layer formed on top of a micromachined mold.

As can be seen in FIG. 2, a second micro-machined mold 12 having a raised protrusion 13 extending therealong is also provided. A second elastomeric layer 22 is cast on top of mold 12, as shown, such that a recess 23 will be formed in its bottom surface corresponding to the dimensions of protrusion 13.

Figure 3:
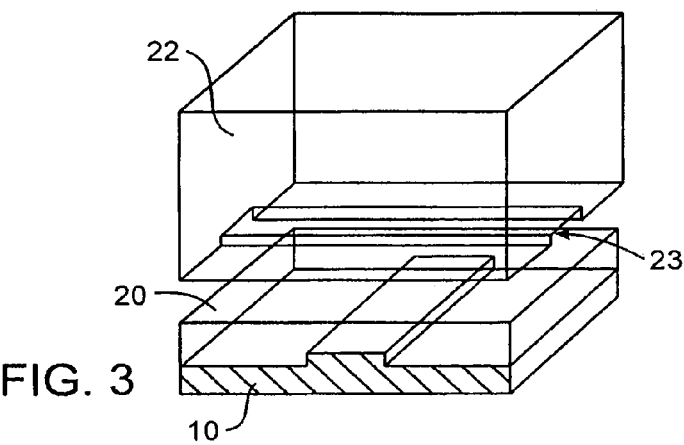
FIG. 3 is an illustration of the elastomeric layer of FIG. 2 removed from the micromachined mold and positioned over the top of the elastomeric layer of FIG. 1
Figure 4:
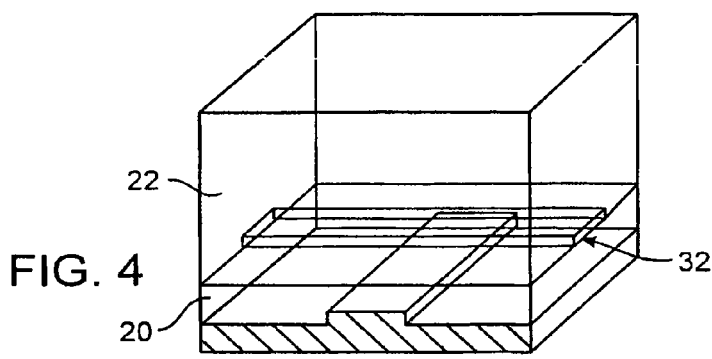
FIG. 4 is an illustration corresponding to FIG. 3, but showing the second elastomeric layer positioned on top of the first elastomeric layer.

As can be seen in the sequential steps illustrated in FIGS. 3 and 4, second elastomeric layer 22 is then removed from mold 12 and placed on top of first elastomeric layer 20. As can be seen, recess 23 extending along the bottom surface of second elastomeric layer 22 will form a flow channel 32.

Figure 5:
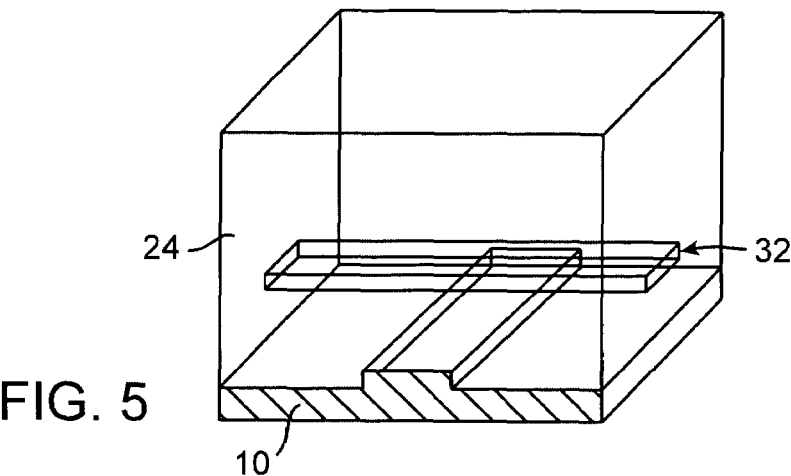
FIG. 5 is an illustration corresponding to FIG. 4, but showing the first and second elastomeric layers bonded together.

Referring to FIG. 5, the separate first and second elastomeric layers 20 and 22 (FIG. 4) are then bonded together to form an integrated (i.e.: monolithic) elastomeric structure 24.

Figure 6:
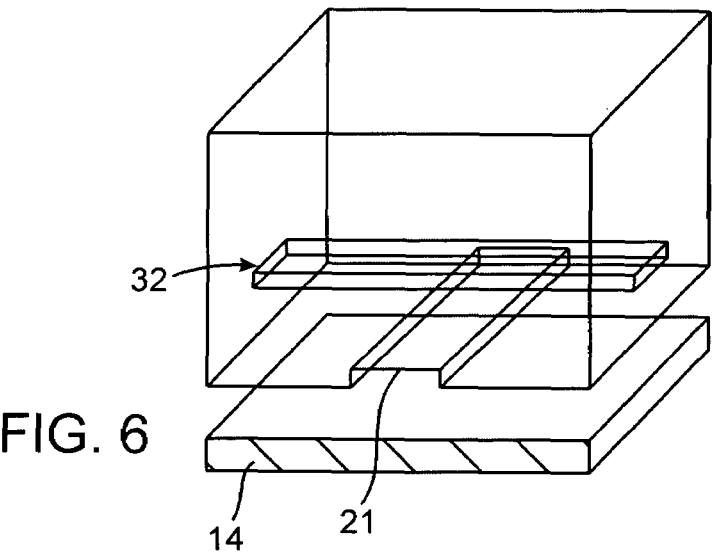
FIG. 6 is an illustration corresponding to FIG. 5, but showing the first micromachined mold removed and a planar substrate positioned in its place.
Figure 7A:
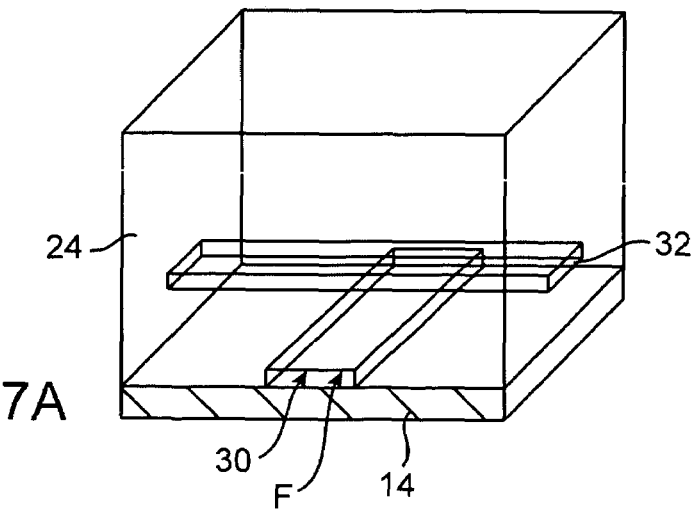
FIG. 7A is an illustration corresponding to FIG. 6, but showing the elastomeric structure sealed onto the planar substrate.
Figure 7B:
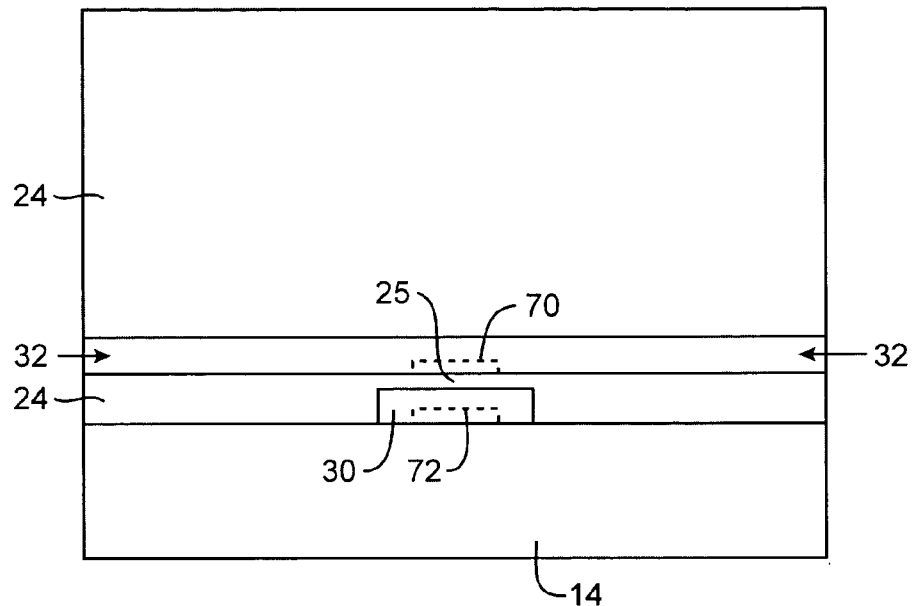
FIG. 7B is a front sectional view corresponding to FIG. 7A, showing an open flow channel.

As can been seen in the sequential step of FIGS. 6 and 7A, elastomeric structure 24 is then removed from mold 10 and positioned on top of a planar substrate 14. As can be seen in FIGS. 7A and 7B, when elastomeric structure 24 has been sealed at its bottom surface to planar substrate 14, recess 21 will form a flow channel 30.

The present elastomeric structures form a reversible hermetic seal with nearly any smooth planar substrate. An advantage to forming a seal this way is that the elastomeric structures may be peeled up, washed, and re-used. In preferred aspects, planar substrate 14 is glass. A further advantage of using glass is that glass is transparent, allowing optical interrogation of elastomer channels and reservoirs. Alternatively, the elastomeric structure may be bonded onto a flat elastomer layer by the same method as described above, forming a permanent and high-strength bond. This may prove advantageous when higher back pressures are used.

As can be seen in FIGS. 7A and 7B, flow channels 30 and 32 are preferably disposed at an angle to one another with a small membrane 25 of substrate 24 separating the top of flow channel 30 from the bottom of flow channel 32.

In preferred aspects, planar substrate 14 is glass. An advantage of using glass is that the present elastomeric structures may be peeled up, washed and reused. A further advantage of using glass is that optical sensing may be employed. Alternatively, planar substrate 14 may be an elastomer itself, which may prove advantageous when higher back pressures are used.

The method of fabrication just described may be varied to form a structure having a membrane composed of an elastomeric material different than that forming the walls of the channels of the device. This variant fabrication method is illustrated in FIGS. 7C-7G.

Figure 7H:
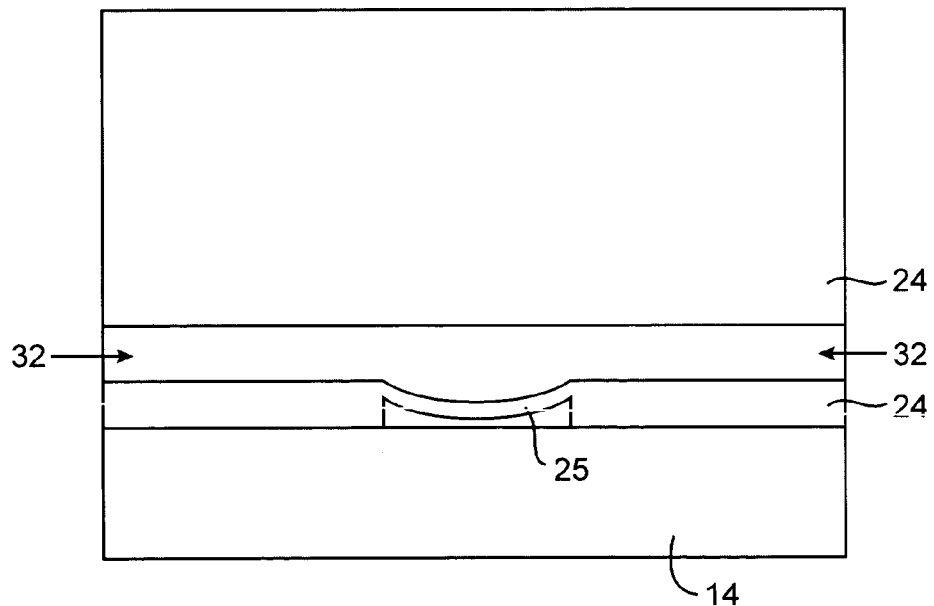
FIG. 7H is a front sectional view showing the valve of FIG. 7B in an actuated state.
Figure 7C:
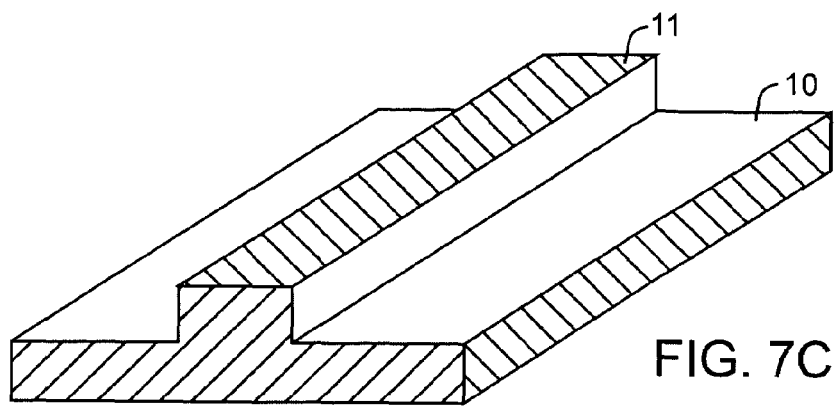
FIGS. 7C-7G are illustrations showing steps of a method for forming an elastomeric structure having a membrane formed from a separate elastomeric layer.
Figure 7D:
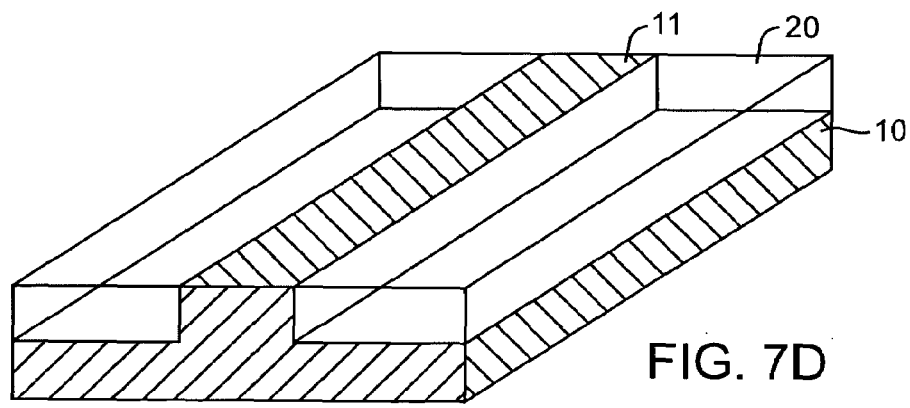

Referring to FIG. 7C, a first micro-machined mold 10 is provided. Micro-machined mold 10 has a raised line or protrusion 11 extending therealong. In FIG. 7D, first elastomeric layer 20 is cast on top of first micro-machined mold 10 such that the top of the first elastomeric layer 20 is flush with the top of raised line or protrusion 11. This may be accomplished by carefully controlling the volume of elastomeric material spun onto mold 10 relative to the known height of raised line 11. Alternatively, the desired shape could be formed by injection molding.

Figure 7E:
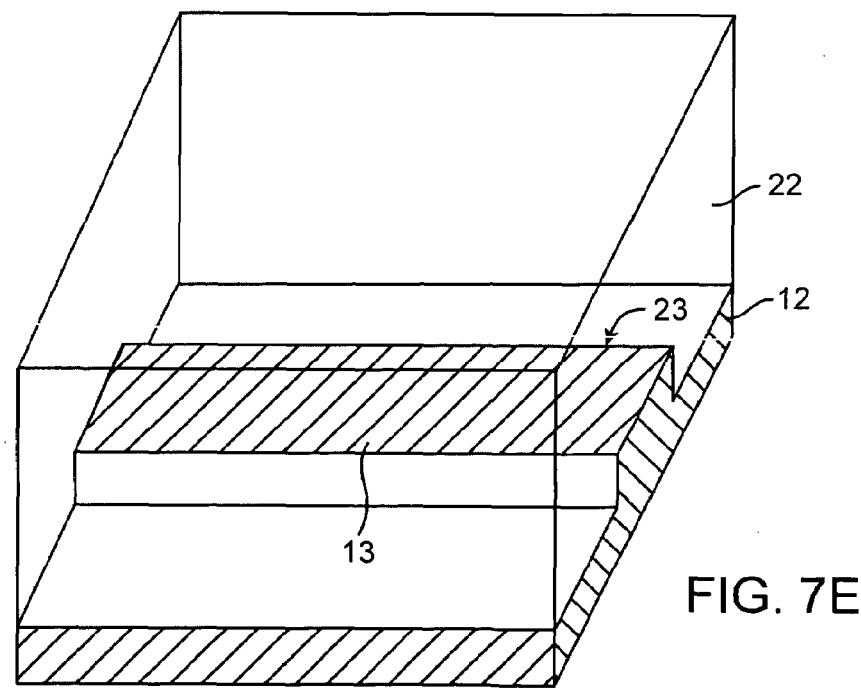

In FIG. 7E, second micro-machined mold 12 having a raised protrusion 13 extending therealong is also provided. Second elastomeric layer 22 is cast on top of second mold 12 as shown, such that recess 23 is formed in its bottom surface corresponding to the dimensions of protrusion 13.

Figure 7F:
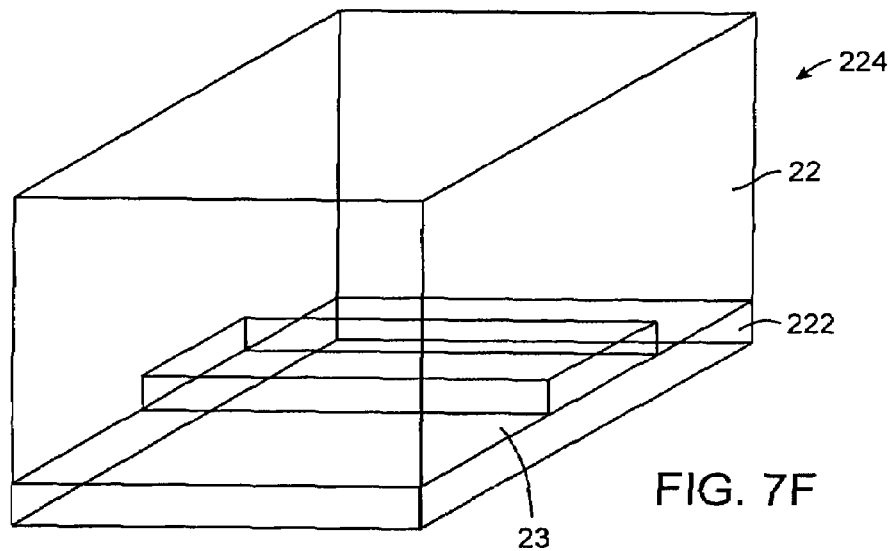

In FIG. 7F, second elastomeric layer 22 is removed from mold 12 and placed on top of third elastomeric layer 222. Second elastomeric layer 22 is bonded to third elastomeric layer 20 to form integral elastomeric block 224 using techniques described in detail below. At this point in the process, recess 23 formerly occupied by raised line 13 will form flow channel 23.

Figure 7G:
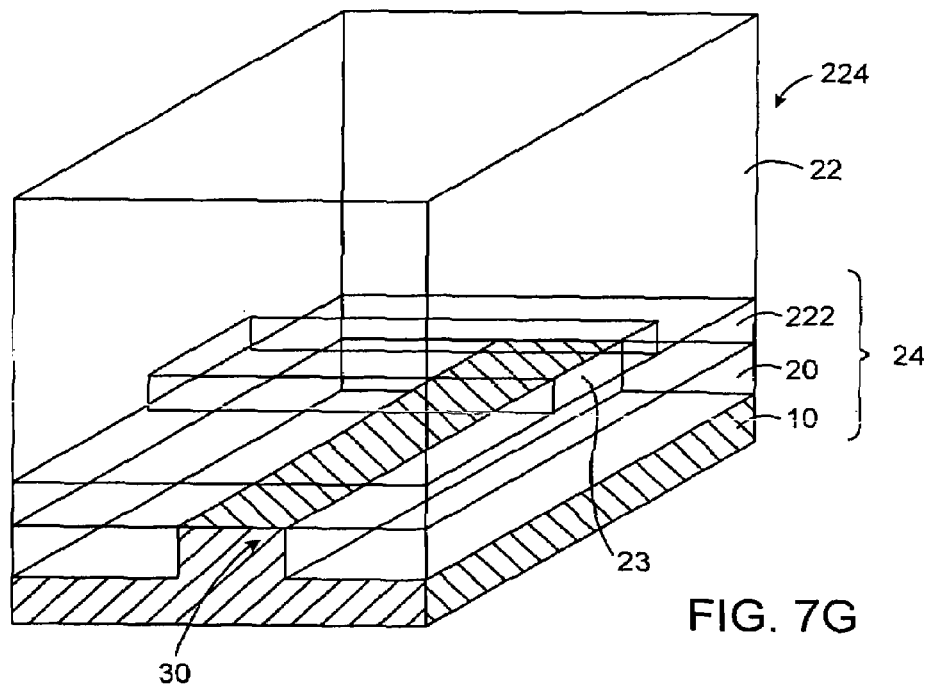

In FIG. 7G, elastomeric block 224 is placed on top of first micro-machined mold 10 and first elastomeric layer 20. Elastomeric block and first elastomeric layer 20 are then bonded together to form an integrated (i.e.: monolithic) elastomeric structure 24 having a membrane composed of a separate elastomeric layer 222.

When elastomeric structure 24 has been sealed at its bottom surface to a planar substrate in the manner described above in connection with FIG. 7A, the recess formerly occupied by raised line 11 will form flow channel 30.

The variant fabrication method illustrated above in conjunction with FIGS. 7C-7G offers the advantage of permitting the membrane portion to be composed of a separate material than the elastomeric material of the remainder of the structure. This is important because the thickness and elastic properties of the membrane play a key role in operation of the device. Moreover, this method allows the separate elastomer layer to readily be subjected to conditioning prior to incorporation into the elastomer structure. As discussed in detail below, examples of potentially desirable condition include the introduction of magnetic or electrically conducting species to permit actuation of the membrane, and/or the introduction of dopant into the membrane in order to alter its elasticity.

While the above method is illustrated in connection with forming various shaped elastomeric layers formed by replication molding on top of a micromachined mold, the present invention is not limited to this technique. Other techniques could be employed to form the individual layers of shaped elastomeric material that are to be bonded together. For example, a shaped layer of elastomeric material could be formed by laser cutting or injection molding, or by methods utilizing chemical etching and/or sacrificial materials as discussed below in conjunction with the second exemplary method.

An alternative method fabricates a patterned elastomer structure utilizing development of photoresist encapsulated within elastomer material. However, the methods in accordance with the present invention are not limited to utilizing photoresist. Other materials such as metals could also serve as sacrificial materials to be removed selective to the surrounding elastomer material, and the method would remain within the scope of the present invention. For example, gold metal may be etched selective to RTV 615 elastomer utilizing the appropriate chemical mixture.

2. Layer and Channel Dimensions

Microfabricated refers to the size of features of an elastomeric structure fabricated in accordance with an embodiment of the present invention. In general, variation in at least one dimension of microfabricated structures is controlled to the micron level, with at least one dimension being microscopic (i.e. below 1000 μm). Microfabrication typically involves semiconductor or MEMS fabrication techniques such as photolithography and spincoating that are designed for to produce feature dimensions on the microscopic level, with at least some of the dimension of the microfabricated structure requiring a microscope to reasonably resolve/image the structure.

In preferred aspects, flow channels 30 and 32 preferably have width-to-depth ratios of about 10:1. A non-exclusive list of other ranges of width-to-depth ratios in accordance with embodiments of the present invention is 0.1:1 to 100:1, more preferably 1:1 to 50:1, more preferably 2:1 to 20:1, and most preferably 3:1 to 15:1. In an exemplary aspect, flow channels 30 and 32 have widths of about 1 to 1000 microns. A non-exclusive list of other ranges of widths of flow channels in accordance with embodiments of the present invention is 0.01 to 1000 microns, more preferably 0.05 to 1000 microns, more preferably 0.2 to 500 microns, more preferably 1 to 250 microns, and most preferably 10 to 200 microns. Exemplary channel widths include 0.1 μm, 1 μm, 2 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, and 250 μm.

Flow channels 30 and 32 have depths of about 1 to 100 microns. A non-exclusive list of other ranges of depths of flow channels in accordance with embodiments of the present invention is 0.01 to 1000 microns, more preferably 0.05 to 500 microns, more preferably 0.2 to 250 microns, and more preferably 1 to 100 microns, more preferably 2 to 20 microns, and most preferably 5 to 10 microns. Exemplary channel depths include including 0.01 μm, 0.02 μm, 0.05 μm, 0.1 μm, 0.2 μm, 0.5 μm, 1 μm, 2 μm, 3 μm, 4 μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, and 250 μm.

The flow channels are not limited to these specific dimension ranges and examples given above, and may vary in width in order to affect the magnitude of force required to deflect the membrane as discussed at length below in conjunction with FIG. 27. For example, extremely narrow flow channels having a width on the order of 0.01 μm may be useful in optical and other applications, as discussed in detail below. Elastomeric structures which include portions having channels of even greater width than described above are also contemplated by the present invention, and examples of applications of utilizing such wider flow channels include fluid reservoir and mixing channel structures.

The Elastomeric layers may be cast thick for mechanical stability. In an exemplary embodiment, elastomeric layer 22 of FIG. 1 is 50 microns to several centimeters thick, and more preferably approximately 4 mm thick. A non-exclusive list of ranges of thickness of the elastomer layer in accordance with other embodiments of the present invention is between about 0.1 micron to 10 cm, 1 micron to 5 cm, 10 microns to 2 cm, 100 microns to 10 mm.

Accordingly, membrane 25 of FIG. 7B separating flow channels 30 and 32 has a typical thickness of between about 0.01 and 1000 microns, more preferably 0.05 to 500 microns, more preferably 0.2 to 250, more preferably 1 to 100 microns, more preferably 2 to 50 microns, and most preferably 5 to 40 microns. As such, the thickness of elastomeric layer 22 is about 100 times the thickness of elastomeric layer 20. Exemplary membrane thicknesses include 0.01 μm, 0.02 μm, 0.03 μm, 0.05 μm, 0.1 μm, 0.2 μm, 0.3 μm, 0.5 μm, 1 μm, 2 μm, 3

μm, 5 μm, 7.5 μm, 10 μm, 12.5 μm, 15 μm, 17.5 μm, 20 μm, 22.5 μm, 25 μm, 30 μm, 40 μm, 50 μm, 75 μm, 100 μm, 150 μm, 200 μm, 250 μm, 300 μm, 400 μm, 500 μm, 750 μm, and 1000 μm.

3. Soft Lithographic Bonding

Preferably, elastomeric layers are bonded together chemically, using chemistry that is intrinsic to the polymers comprising the patterned elastomer layers. Most preferably, the bonding comprises two component "addition cure" bonding.

In a preferred aspect, the various layers of elastomer are bound together in a heterogeneous bonding in which the layers have a different chemistry. Alternatively, a homogenous bonding may be used in which all layers would be of the same chemistry. Thirdly, the respective elastomer layers may optionally be glued together by an adhesive instead. In a fourth aspect, the elastomeric layers may be thermoset elastomers bonded together by heating.

In one aspect of homogeneous bonding, the elastomeric layers are composed of the same elastomer material, with the same chemical entity in one layer reacting with the same chemical entity in the other layer to bond the layers together. In one embodiment, bonding between polymer chains of like elastomer layers may result from activation of a crosslinking agent due to light, heat, or chemical reaction with a separate chemical species.

Alternatively in a heterogeneous aspect, the elastomeric layers are composed of different elastomeric materials, with a first chemical entity in one layer reacting with a second chemical entity in another layer. In one exemplary heterogeneous aspect, the bonding process used to bind respective elastomeric layers together may comprise bonding together two layers of RTV 615 silicone. RTV 615 silicone is a two-part addition-cure silicone rubber. Part A contains vinyl groups and catalyst; part B contains silicon hydride (Si—H) groups. The conventional ratio for RTV 615 is 10A:1B. For bonding, one layer may be made with 30A:1B (i.e. excess vinyl groups) and the other with 3A:1B (i.e. excess Si—H groups). Each layer is cured separately. When the two layers are brought into contact and heated at elevated temperature, they bond irreversibly forming a monolithic elastomeric substrate.

In an exemplary aspect of the present invention, elastomeric structures are formed utilizing Sylgard 182, 184 or 186, or aliphatic urethane diacrylates such as (but not limited to) Ebecryl 270 or Irr 245 from UCB Chemical.

In one embodiment in accordance with the present invention, two-layer elastomeric structures were fabricated from pure acrylated Urethane Ebe 270. A thin bottom layer was spin coated at 8000 rpm for 15 seconds at 170° C. The top and bottom layers were initially cured under ultraviolet light for 10 minutes under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhesion to glass.

In another embodiment in accordance with the present invention, two-layer elastomeric structures were fabricated from a combination of 25% Ebe 270/50% Irr 245/25% isopropyl alcohol for a thin bottom layer, and pure acrylated Urethane Ebe 270 as a top layer. The thin bottom layer was initially cured for 5 min, and the top layer initially cured for 10 minutes, under ultraviolet light under nitrogen utilizing a Model ELC 500 device manufactured by Electrolite corporation. The assembled layers were then cured for an additional 30 minutes. Reaction was catalyzed by a 0.5% vol/vol mixture of Irgacure 500 manufactured by Ciba-Geigy Chemicals. The resulting elastomeric material exhibited moderate elasticity and adhered to glass.

Alternatively, other bonding methods may be used, including activating the elastomer surface, for example by plasma exposure, so that the elastomer layers/substrate will bond when placed in contact. For example, one possible approach to bonding together elastomer layers composed of the same material is set forth by Duffy et al, "Rapid Prototyping of Microfluidic Systems in Poly (dimethylsiloxane)", *Analytical Chemistry* (1998), 70, 4974-4984, incorporated herein by reference. This paper discusses that exposing polydimethylsiloxane (PDMS) layers to oxygen plasma causes oxidation of the surface, with irreversible bonding occurring when the two oxidized layers are placed into contact.

Yet another approach to bonding together successive layers of elastomer is to utilize the adhesive properties of uncured elastomer. Specifically, a thin layer of uncured elastomer such as RTV 615 is applied on top of a first cured elastomeric layer. Next, a second cured elastomeric layer is placed on top of the uncured elastomeric layer. The thin middle layer of uncured elastomer is then cured to produce a monolithic elastomeric structure. Alternatively, uncured elastomer can be applied to the bottom of a first cured elastomer layer, with the first cured elastomer layer placed on top of a second cured elastomer layer. Curing the middle thin elastomer layer again results in formation of a monolithic elastomeric structure.

Where encapsulation of sacrificial layers is employed to fabricate the elastomer structure, bonding of successive elastomeric layers may be accomplished by pouring uncured elastomer over a previously cured elastomeric layer and any sacrificial material patterned thereupon. Bonding between elastomer layers occurs due to interpenetration and reaction of the polymer chains of an uncured elastomer layer with the polymer chains of a cured elastomer layer. Subsequent curing of the elastomeric layer will create a bond between the elastomeric layers and create a monolithic elastomeric structure.

Referring to the first method of FIGS. 1 to 7B, first elastomeric layer 20 may be created by spin-coating an RTV mixture on microfabricated mold 10 at 2000 rpm's for 30 seconds yielding a thickness of approximately 40 microns. Second elastomeric layer 22 may be created by spin-coating an RTV mixture on microfabricated mold 12. Both layers 20 and 22 may be separately baked or cured at about 80° C. for 1.5 hours. The second elastomeric layer 22 may be bonded onto first elastomeric layer 20 at about 80° C. for about 1.5 hours.

Micromachined molds 10 and 12 may be patterned photoresist on silicon wafers. In an exemplary aspect, a Shipley SJR 5740 photoresist was spun at 2000 rpm patterned with a high resolution transparency film as a mask and then developed yielding an inverse channel of approximately 10 microns in height. When baked at approximately 200° C. for about 30 minutes, the photoresist reflows and the inverse channels become rounded. In preferred aspects, the molds may be treated with trimethylchlorosilane (TMCS) vapor for about a minute before each use in order to prevent adhesion of silicone rubber.

4. Suitable Elastomeric Materials

Allcock et al, Contemporary *Polymer Chemistry*, $2^{nd}$ Ed. describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed. The elasticity exhibited by elastomeric materials may be characterized by a Young's modulus. Elastomeric materials having a Young's modulus of between about 1 Pa-1 TPa, more preferably between about 10 Pa-100 GPa, more preferably between about 20 Pa-1 GPa, more preferably between about 50 Pa-10 MPa, and more preferably between about 100 Pa-1 MPa are useful in accordance with the present invention, although elastomeric materials having a Young's modulus outside of these ranges could also be utilized depending upon the needs of a particular application.

The systems of the present invention may be fabricated from a wide variety of elastomers. In an exemplary aspect, the elastomeric layers may preferably be fabricated from silicone rubber. However, other suitable elastomers may also be used.

In an exemplary aspect of the present invention, the present systems are fabricated from an elastomeric polymer such as GE RTV 615 (formulation), a vinyl-silane crosslinked (type) silicone elastomer (family). However, the present systems are not limited to this one formulation, type or even this family of polymer; rather, nearly any elastomeric polymer is suitable. An important requirement for the preferred method of fabrication of the present microvalves is the ability to bond multiple layers of elastomers together. In the case of multilayer soft lithography, layers of elastomer are cured separately and then bonded together. This scheme requires that cured layers possess sufficient reactivity to bond together. Either the layers may be of the same type, and are capable of bonding to themselves, or they may be of two different types, and are capable of bonding to each other. Other possibilities include the use an adhesive between layers and the use of thermoset elastomers.

Given the tremendous diversity of polymer chemistries, precursors, synthetic methods, reaction conditions, and potential additives, there are a huge number of possible elastomer systems that could be used to make monolithic elastomeric microvalves and pumps. Variations in the materials used will most likely be driven by the need for particular material properties, i.e. solvent resistance, stiffness, gas permeability, or temperature stability.

There are many, many types of elastomeric polymers. A brief description of the most common classes of elastomers is presented here, with the intent of showing that even with relatively "standard" polymers, many possibilities for bonding exist. Common elastomeric polymers include polyisoprene, polybutadiene, polychloroprene, polyisobutylene, poly(styrene-butadiene-styrene), the polyurethanes, and silicones.

Polyisoprene, Polybutadiene, Polychloroprene:

Polyisoprene, polybutadiene, and polychloroprene are all polymerized from diene monomers, and therefore have one double bond per monomer when polymerized. This double bond allows the polymers to be converted to elastomers by vulcanization (essentially, sulfur is used to form crosslinks between the double bonds by heating). This would easily allow homogeneous multilayer soft lithography by incomplete vulcanization of the layers to be bonded; photoresist encapsulation would be possible by a similar mechanism.

Polyisobutylene:

Pure Polyisobutylene has no double bonds, but is crosslinked to use as an elastomer by including a small amount (~1%) of isoprene in the polymerization. The isoprene monomers give pendant double bonds on the Polyisobutylene backbone, which may then be vulcanized as above.

Poly(styrene-butadiene-styrene):

Poly(styrene-butadiene-styrene) is produced by living anionic polymerization (that is, there is no natural chain-terminating step in the reaction), so "live" polymer ends can exist in the cured polymer. This makes it a natural candidate for the present photoresist encapsulation system (where there will be plenty of unreacted monomer in the liquid layer poured on top of the cured layer). Incomplete curing would allow homogeneous multilayer soft lithography (A to A bonding). The chemistry also facilitates making one layer with extra butadiene ("A") and coupling agent and the other layer ("B") with a butadiene deficit (for heterogeneous multilayer soft lithography). SBS is a "thermoset elastomer", meaning that above a certain temperature it melts and becomes plastic (as opposed to elastic); reducing the temperature yields the elastomer again. Thus, layers can be bonded together by heating.

Polyurethanes:

Polyurethanes are produced from di-isocyanates (A-A) and di-alcohols or di-amines (B-B); since there are a large variety of di-isocyanates and di-alcohols/amines, the number of different types of polyurethanes is huge. The A vs. B nature of the polymers, however, would make them useful for heterogeneous multilayer soft lithography just as RTV 615 is: by using excess A-A in one layer and excess B-B in the other layer.

Silicones:

Silicone polymers probably have the greatest structural variety, and almost certainly have the greatest number of commercially available formulations. The vinyl-to-(Si—H) crosslinking of RTV 615 (which allows both heterogeneous multilayer soft lithography and photoresist encapsulation) has already been discussed, but this is only one of several crosslinking methods used in silicone polymer chemistry.

5. Operation of Device

FIGS. 7B and 7H together show the closing of a first flow channel by pressurizing a second flow channel, with FIG. 7B (a front sectional view cutting through flow channel 32 in corresponding FIG. 7A), showing an open first flow channel 30; with FIG. 7H showing first flow channel 30 closed by pressurization of the second flow channel 32.

Referring to FIG. 7B, first flow channel 30 and second flow channel 32 are shown. Membrane 25 separates the flow channels, forming the top of first flow channel 30 and the bottom of second flow channel 32. As can be seen, flow channel 30 is "open".

As can be seen in FIG. 7H, pressurization of flow channel 32 (either by gas or liquid introduced therein) causes membrane 25 to deflect downward, thereby pinching off flow F passing through flow channel 30. Accordingly, by varying the pressure in channel 32, a linearly actuable valving system is provided such that flow channel 30 can be opened or closed by moving membrane 25 as desired. (For illustration purposes only, channel 30 in FIG. 7G is shown in a "mostly closed" position, rather than a "fully closed" position).

Since such valves are actuated by moving the roof of the channels themselves (i.e.: moving membrane 25) valves and pumps produced by this technique have a truly zero dead volume, and switching valves made by this technique have a dead volume approximately equal to the active volume of the valve, for example about 100×100×10 μm=100 pL. Such dead volumes and areas consumed by the moving membrane are approximately two orders of magnitude smaller than known conventional microvalves. Smaller and larger valves and switching valves are contemplated in the present invention, and a non-exclusive list of ranges of dead volume includes 1 aL to 1 uL, 100 aL to 100 nL, 1 fL to 10 nL, 100 fL to 1 nL, and 1 pL to 100 pL.

The extremely small volumes capable of being delivered by pumps and valves in accordance with the present invention represent a substantial advantage. Specifically, the smallest known volumes of fluid capable of being manually metered is around 0.1 µl. The smallest known volumes capable of being metered by automated systems is about ten-times larger (1 µl). Utilizing pumps and valves in accordance with the present invention, volumes of liquid of 10 nl or smaller can routinely be metered and dispensed. The accurate metering of extremely small volumes of fluid enabled by the present invention would be extremely valuable in a large number of biological applications, including diagnostic tests and assays.

Equation 1 represents a highly simplified mathematical model of deflection of a rectangular, linear, elastic, isotropic plate of uniform thickness by an applied pressure:

$$w=(BPb^4)/(Eh^3), \text{ where:} \quad (1)$$

w=deflection of plate;
B=shape coefficient (dependent upon length vs. width and support of edges of plate);
P=applied pressure;
b=plate width
E=Young's modulus; and
h=plate thickness.

Thus even in this extremely simplified expression, deflection of an elastomeric membrane in response to a pressure will be a function of: the length, width, and thickness of the membrane, the flexibility of the membrane (Young's modulus), and the applied actuation force. Because each of these parameters will vary widely depending upon the actual dimensions and physical composition of a particular elastomeric device in accordance with the present invention, a wide range of membrane thicknesses and elasticity's, channel widths, and actuation forces are contemplated by the present invention.

It should be understood that the formula just presented is only an approximation, since in general the membrane does not have uniform thickness, the membrane thickness is not necessarily small compared to the length and width, and the deflection is not necessarily small compared to length, width, or thickness of the membrane. Nevertheless, the equation serves as a useful guide for adjusting variable parameters to achieve a desired response of deflection versus applied force.

Figure 8A:
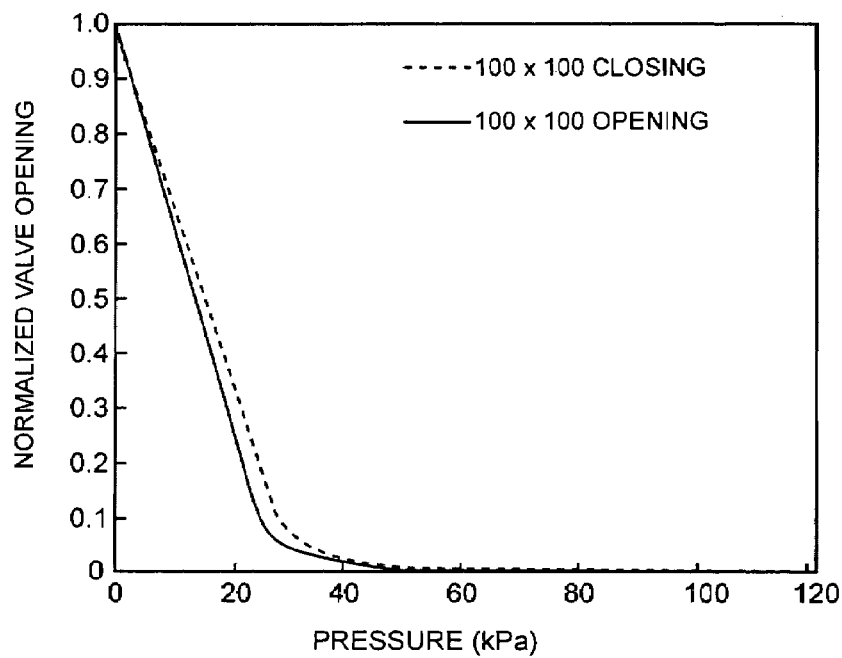
FIGS. 8A and 8B illustrates valve opening vs. applied pressure for various flow channels.
Figure 8B:
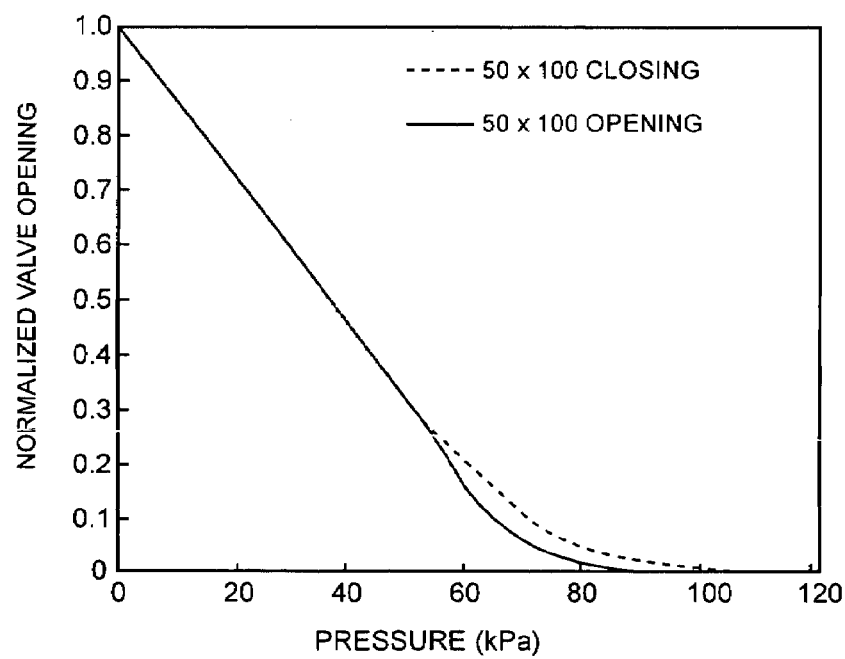

FIGS. 8A and 8B illustrate valve opening vs. applied pressure for a 100 µm wide first flow channel 30 and a 50 µm wide second flow channel 32. The membrane of this device was formed by a layer of General Electric Silicones RTV 615 having a thickness of approximately 30 µm and a Young's modulus of approximately 750 kPa. FIGS. 21a and 21b show the extent of opening of the valve to be substantially linear over most of the range of applied pressures.

Air pressure was applied to actuate the membrane of the device through a 10 cm long piece of plastic tubing having an outer diameter of 0.025" connected to a 25 mm piece of stainless steel hypodermic tubing with an outer diameter of 0.025" and an inner diameter of 0.013". This tubing was placed into contact with the control channel by insertion into the elastomeric block in a direction normal to the control channel. Air pressure was applied to the hypodermic tubing from an external LHDA miniature solenoid valve manufactured by Lee Co.

While control of the flow of material through the device has so far been described utilizing applied gas pressure, other fluids could be used.

For example, air is compressible, and thus experiences some finite delay between the time of application of pressure by the external solenoid valve and the time that this pressure is experienced by the membrane. In an alternative embodiment of the present invention, pressure could be applied from an external source to a noncompressible fluid such as water or hydraulic oils, resulting in a near-instantaneous transfer of applied pressure to the membrane. However, if the displaced volume of the valve is large or the control channel is narrow, higher viscosity of a control fluid may contribute to delay in actuation. The optimal medium for transferring pressure will therefore depend upon the particular application and device configuration, and both gaseous and liquid media are contemplated by the invention.

While external applied pressure as described above has been applied by a pump/tank system through a pressure regulator and external miniature valve, other methods of applying external pressure are also contemplated in the present invention, including gas tanks, compressors, piston systems, and columns of liquid. Also contemplated is the use of naturally occurring pressure sources such as may be found inside living organisms, such as blood pressure, gastric pressure, the pressure present in the cerebrospinal fluid, pressure present in the intra-ocular space, and the pressure exerted by muscles during normal flexure. Other methods of regulating external pressure are also contemplated, such as miniature valves, pumps, macroscopic peristaltic pumps, pinch valves, and other types of fluid regulating equipment such as is known in the art.

As can be seen, the response of valves in accordance with embodiments of the present invention have been experimentally shown to be almost perfectly linear over a large portion of its range of travel, with minimal hysteresis. Accordingly, the present valves are ideally suited for microfluidic metering and fluid control. The linearity of the valve response demonstrates that the individual valves are well modeled as Hooke's Law springs. Furthermore, high pressures in the flow channel (i.e.: back pressure) can be countered simply by increasing the actuation pressure. Experimentally, the present inventors have achieved valve closure at back pressures of 70 kPa, but higher pressures are also contemplated. The following is a nonexclusive list of pressure ranges encompassed by the present invention: 10 Pa-25 MPa; 100 Pa-10 Mpa, 1 kPa-1 MPa, 1 kPa-300 kPa, 5 kPa-200 kPa, and 15 kPa-100 kPa.

While valves and pumps do not require linear actuation to open and close, linear response does allow valves to more easily be used as metering devices. In one embodiment of the invention, the opening of the valve is used to control flow rate by being partially actuated to a known degree of closure. Linear valve actuation makes it easier to determine the amount of actuation force required to close the valve to a desired degree of closure. Another benefit of linear actuation is that the force required for valve actuation may be easily determined from the pressure in the flow channel. If actuation is linear, increased pressure in the flow channel may be countered by adding the same pressure (force per unit area) to the actuated portion of the valve.

Linearity of a valve depends on the structure, composition, and method of actuation of the valve structure. Furthermore, whether linearity is a desirable characteristic in a valve depends on the application. Therefore, both linearly and non-linearly actuable valves are contemplated in the present invention, and the pressure ranges over which a valve is linearly actuable will vary with the specific embodiment.

Figure 9:
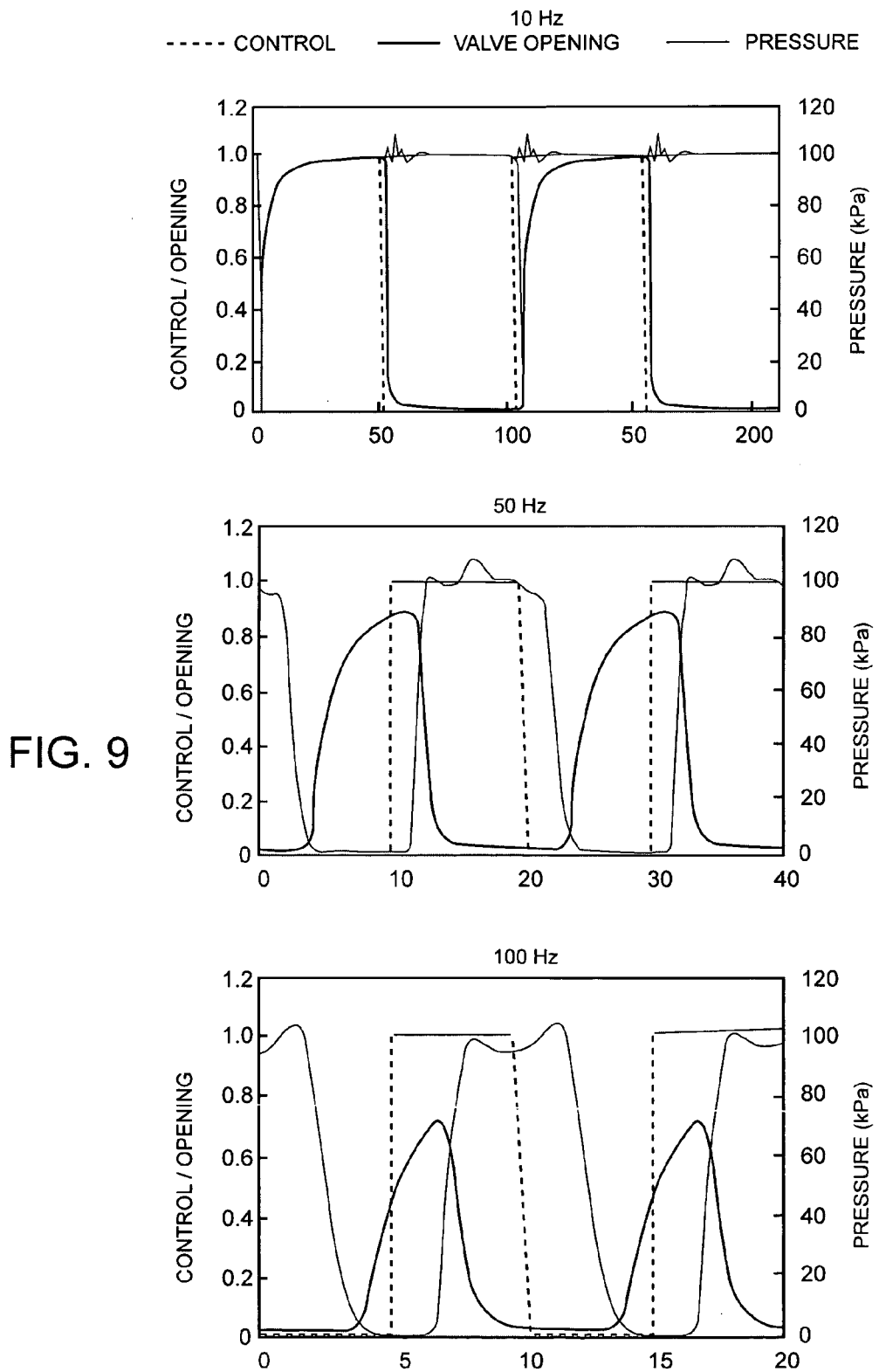
FIG. 9 illustrates time response of a 100 μm×100 μm×10 μm RTV microvalve.

FIG. 9 illustrates time response (i.e.: closure of valve as a function of time in response to a change in applied pressure)

of a 100 µm×100 µm×10 µm RTV microvalve with 10-cm-long air tubing connected from the chip to a pneumatic valve as described above.

Two periods of digital control signal, actual air pressure at the end of the tubing and valve opening are shown in FIG. 9. The pressure applied on the control line is 100 kPa, which is substantially higher than the ~40 kPa required to close the valve. Thus, when closing, the valve is pushed closed with a pressure 60 kPa greater than required. When opening, however, the valve is driven back to its rest position only by its own spring force (≦40 kPa). Thus, τclose is expected to be smaller than τopen. There is also a lag between the control signal and control pressure response, due to the limitations of the miniature valve used to control the pressure. Calling such lags t and the 1/e time constants τ, the values are: topen=3.63 ms, τopen=1.88 ms, tclose=2.15 ms, τclose=0.51 ms. If 3τ each are allowed for opening and closing, the valve runs comfortably at 75 Hz when filled with aqueous solution.

If one used another actuation method which did not suffer from opening and closing lag, this valve would run at ~375 Hz. Note also that the spring constant can be adjusted by changing the membrane thickness; this allows optimization for either fast opening or fast closing. The spring constant could also be adjusted by changing the elasticity (Young's modulus) of the membrane, as is possible by introducing dopant into the membrane or by utilizing a different elastomeric material to serve as the membrane (described above in conjunction with FIGS. 7C-7H.)

When experimentally measuring the valve properties as illustrated in FIG. 9 the valve opening was measured by fluorescence. In these experiments, the flow channel was filled with a solution of fluorescein isothiocyanate (FITC) in buffer (pH≧8) and the fluorescence of a square area occupying the center ~⅓rd of the channel is monitored on an epifluorescence microscope with a photomultiplier tube with a 10 kHz bandwidth. The pressure was monitored with a Wheatstone-bridge pressure sensor (SenSym SCC15GD2) pressurized simultaneously with the control line through nearly identical pneumatic connections.

6. Flow Channel Cross Sections

The flow channels of the present invention may optionally be designed with different cross sectional sizes and shapes, offering different advantages, depending upon their desired application. For example, the cross sectional shape of the lower flow channel may have a curved upper surface, either along its entire length or in the region disposed under an upper cross channel). Such a curved upper surface facilitates valve sealing, as follows.

Figure 10:
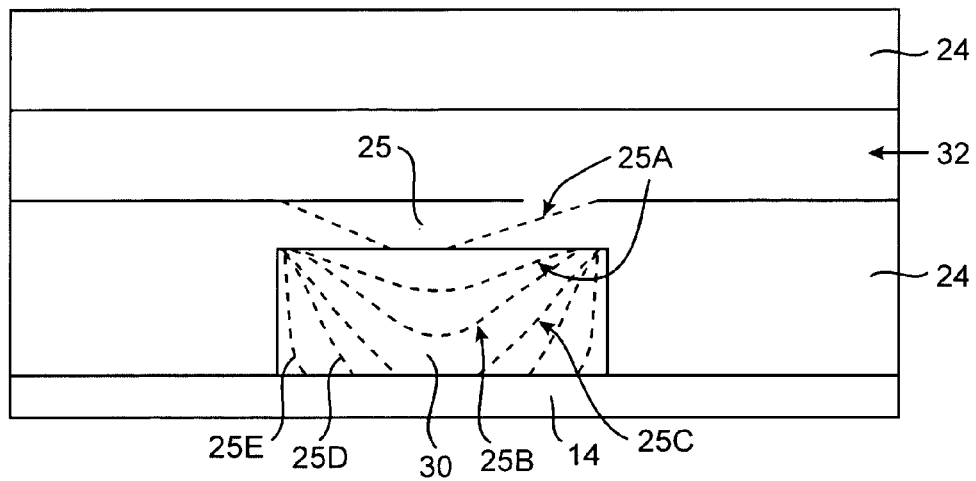
FIG. 10 is a front sectional view of the valve of FIG. 7B showing actuation of the membrane.

Referring to FIG. 10, a cross sectional view (similar to that of FIG. 7B) through flow channels 30 and 32 is shown. As can be seen, flow channel 30 is rectangular in cross sectional shape. In an alternate preferred aspect of the invention, as shown in FIG. 10, the cross-section of a flow channel 30 instead has an upper curved surface.

Referring first to FIG. 10, when flow channel 32 is pressurized, the membrane portion 25 of elastomeric block 24 separating flow channels 30 and 32 will move downwardly to the successive positions shown by the dotted lines 25A, 25B, 25C, 25D, and 25E. As can be seen, incomplete sealing may possibly result at the edges of flow channel 30 adjacent planar substrate 14.

Figure 11:
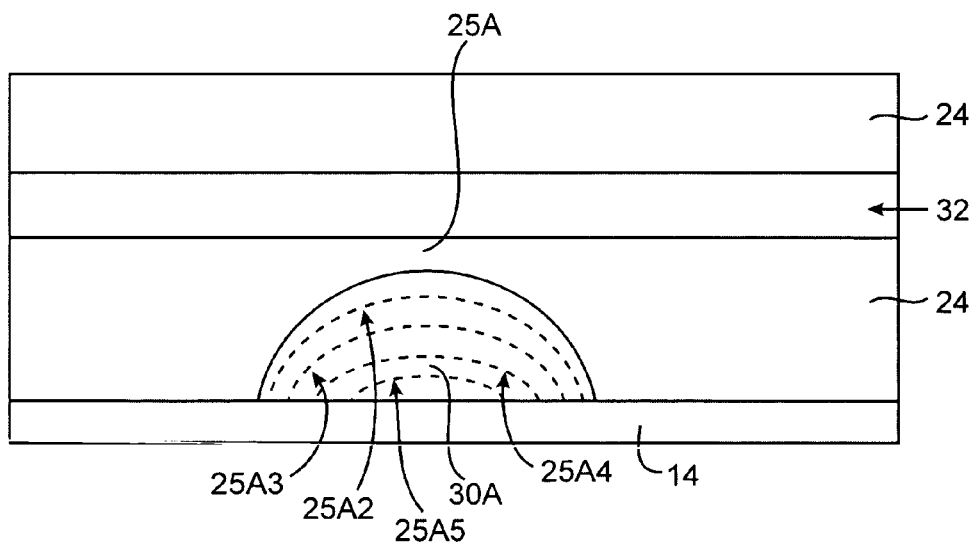
FIG. 11 is a front sectional view of an alternative embodiment of a valve having a flow channel with a curved upper surface.

In the alternate preferred embodiment of FIG. 11, flow channel 30a has a curved upper wall 25A. When flow channel 32 is pressurized, membrane portion 25 will move downwardly to the successive positions shown by dotted lines 25A2, 25A3, 25A4 and 25A5, with edge portions of the membrane moving first into the flow channel, followed by top membrane portions. An advantage of having such a curved upper surface at membrane 25A is that a more complete seal will be provided when flow channel 32 is pressurized. Specifically, the upper wall of the flow channel 30 will provide a continuous contacting edge against planar substrate 14, thereby avoiding the "island" of contact seen between wall 25 and the bottom of flow channel 30 in FIG. 10.

Another advantage of having a curved upper flow channel surface at membrane 25A is that the membrane can more readily conform to the shape and volume of the flow channel in response to actuation. Specifically, where a rectangular flow channel is employed, the entire perimeter (2× flow channel height, plus the flow channel width) must be forced into the flow channel. However where an arched flow channel is used, a smaller perimeter of material (only the semi-circular arched portion) must be forced into the channel. In this manner, the membrane requires less change in perimeter for actuation and is therefore more responsive to an applied actuation force to block the flow channel In an alternate aspect, (not illustrated), the bottom of flow channel 30 is rounded such that its curved surface mates with the curved upper wall 25A as seen in FIG. 20 described above.

In summary, the actual conformational change experienced by the membrane upon actuation will depend upon the configuration of the particular elastomeric structure. Specifically, the conformational change will depend upon the length, width, and thickness profile of the membrane, its attachment to the remainder of the structure, and the height, width, and shape of the flow and control channels and the material properties of the elastomer used. The conformational change may also depend upon the method of actuation, as actuation of the membrane in response to an applied pressure will vary somewhat from actuation in response to a magnetic or electrostatic force.

Moreover, the desired conformational change in the membrane will also vary depending upon the particular application for the elastomeric structure. In the simplest embodiments described above, the valve may either be open or closed, with metering to control the degree of closure of the valve. In other embodiments however, it may be desirable to alter the shape of the membrane and/or the flow channel in order to achieve more complex flow regulation. For instance, the flow channel could be provided with raised protrusions beneath the membrane portion, such that upon actuation the membrane shuts off only a percentage of the flow through the flow channel, with the percentage of flow blocked insensitive to the applied actuation force.

Many membrane thickness profiles and flow channel cross-sections are contemplated by the present invention, including rectangular, trapezoidal, circular, ellipsoidal, parabolic, hyperbolic, and polygonal, as well as sections of the above shapes. More complex cross-sectional shapes, such as the embodiment with protrusions discussed immediately above or an embodiment having concavities in the flow channel, are also contemplated by the present invention.

In addition, while the invention is described primarily above in conjunction with an embodiment wherein the walls and ceiling of the flow channel are formed from elastomer, and the floor of the channel is formed from an underlying substrate, the present invention is not limited to this particular orientation. Walls and floors of channels could also be formed in the underlying substrate, with only the ceiling of the flow channel constructed from elastomer. This elastomer flow channel ceiling would project downward into the channel in response to an applied actuation force, thereby controlling the flow of material through the flow channel. In general, monolithic elastomer structures as described elsewhere in the instant application are preferred for microfluidic applications. However, it may be useful to employ channels formed in the substrate where such an arrangement provides advantages. For instance, a substrate including optical waveguides could be constructed so that the optical waveguides direct light specifically to the side of a microfluidic channel.

7. Networked Systems

Figure 12A:
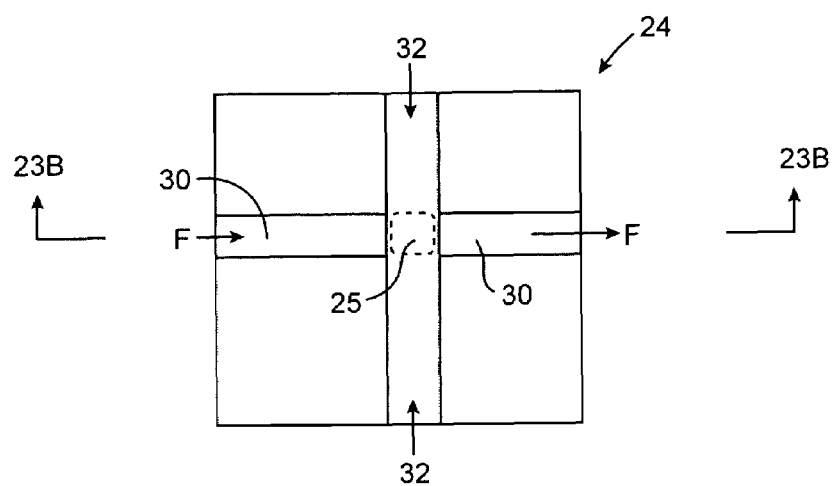
FIG. 12A is a top schematic view of an on/off valve.
Figure 13A:
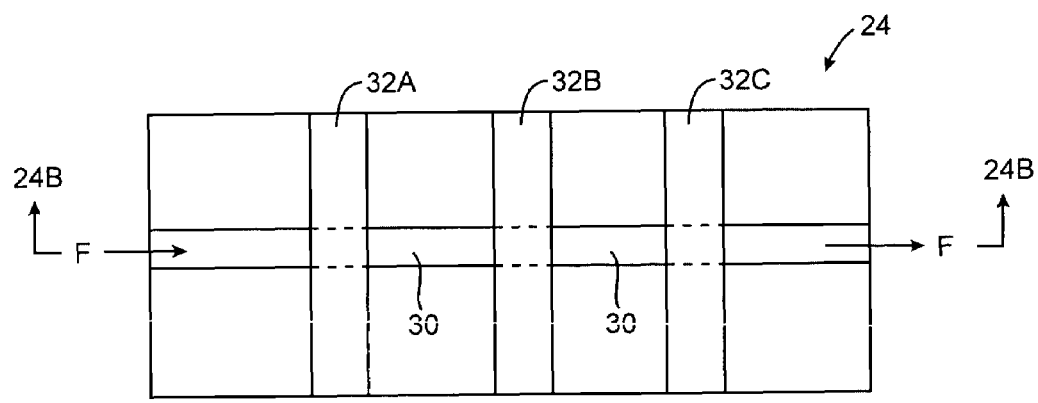
FIG. 13A is a top schematic view of a peristaltic pumping system.
Figure 12B:
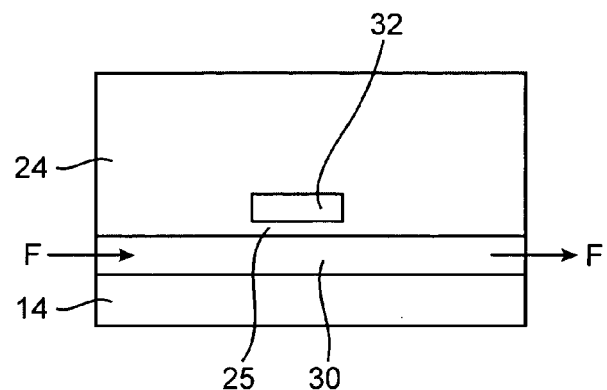
FIG. 12B is a sectional elevation view along line 23B-23B in FIG. 12A
Figure 13B:
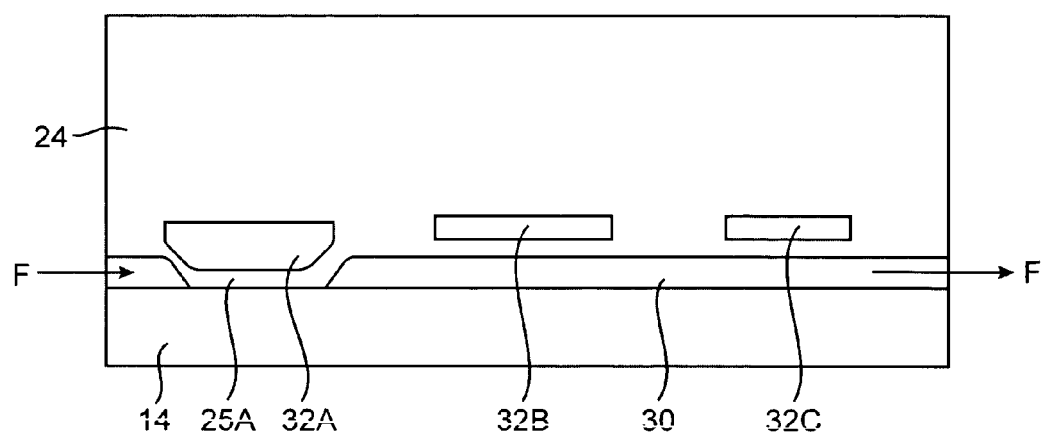
FIG. 13B is a sectional elevation view along line 24B-24B in FIG. 13A
Figure 14:
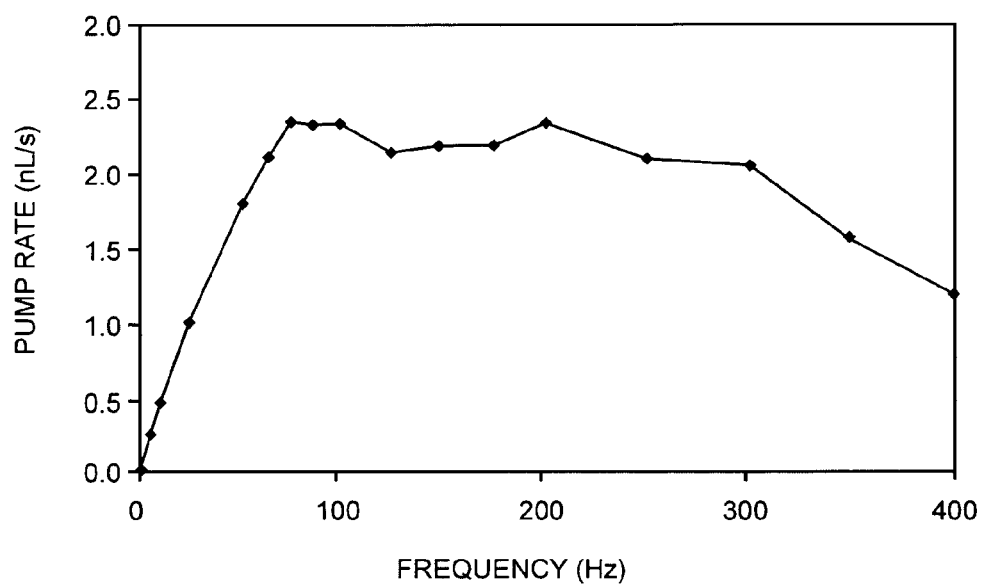
FIG. 14 is a graph showing experimentally achieved pumping rates vs. frequency for an embodiment of the peristaltic pumping system of FIG. 13.
Figure 15A:
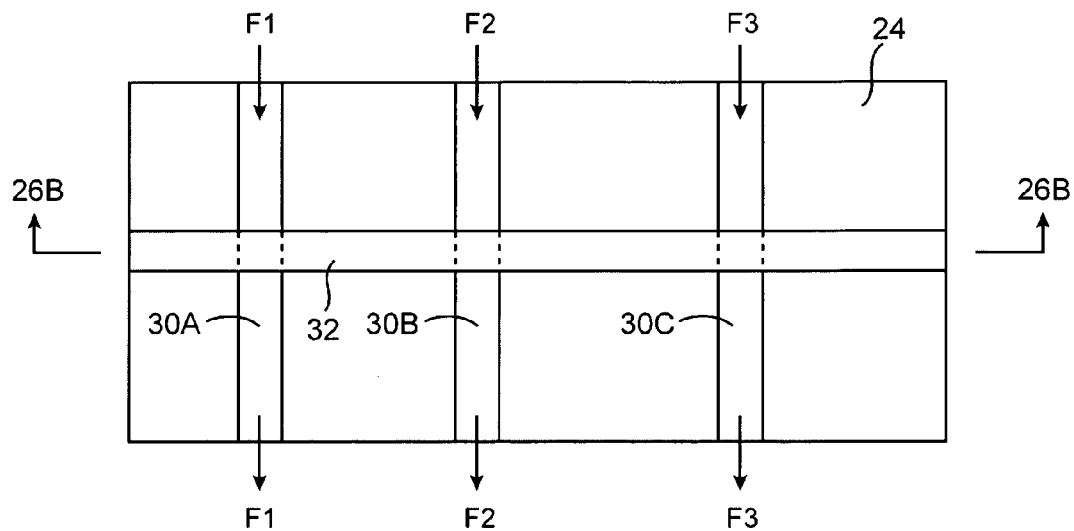
FIG. 15A is a top schematic view of one control line actuating multiple flow lines simultaneously.
Figure 15B:
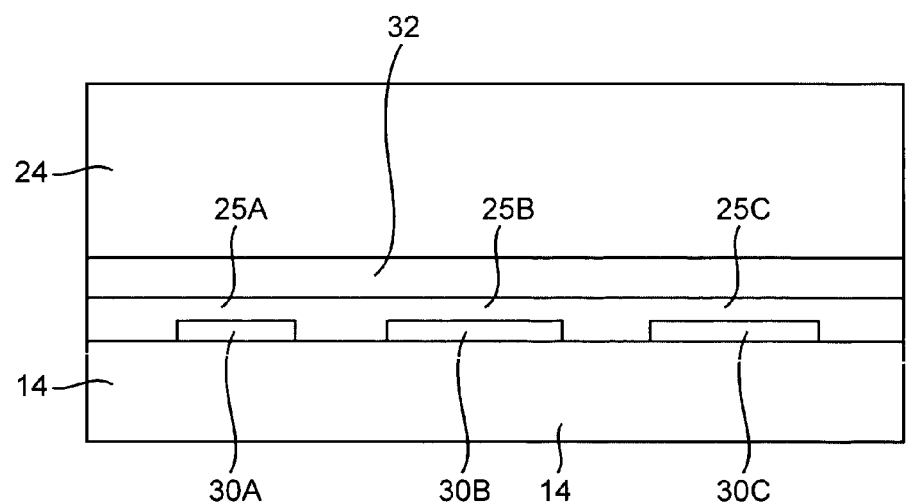
FIG. 15B is a sectional elevation view along line 26B-26B in FIG. 15A
Figure 16:
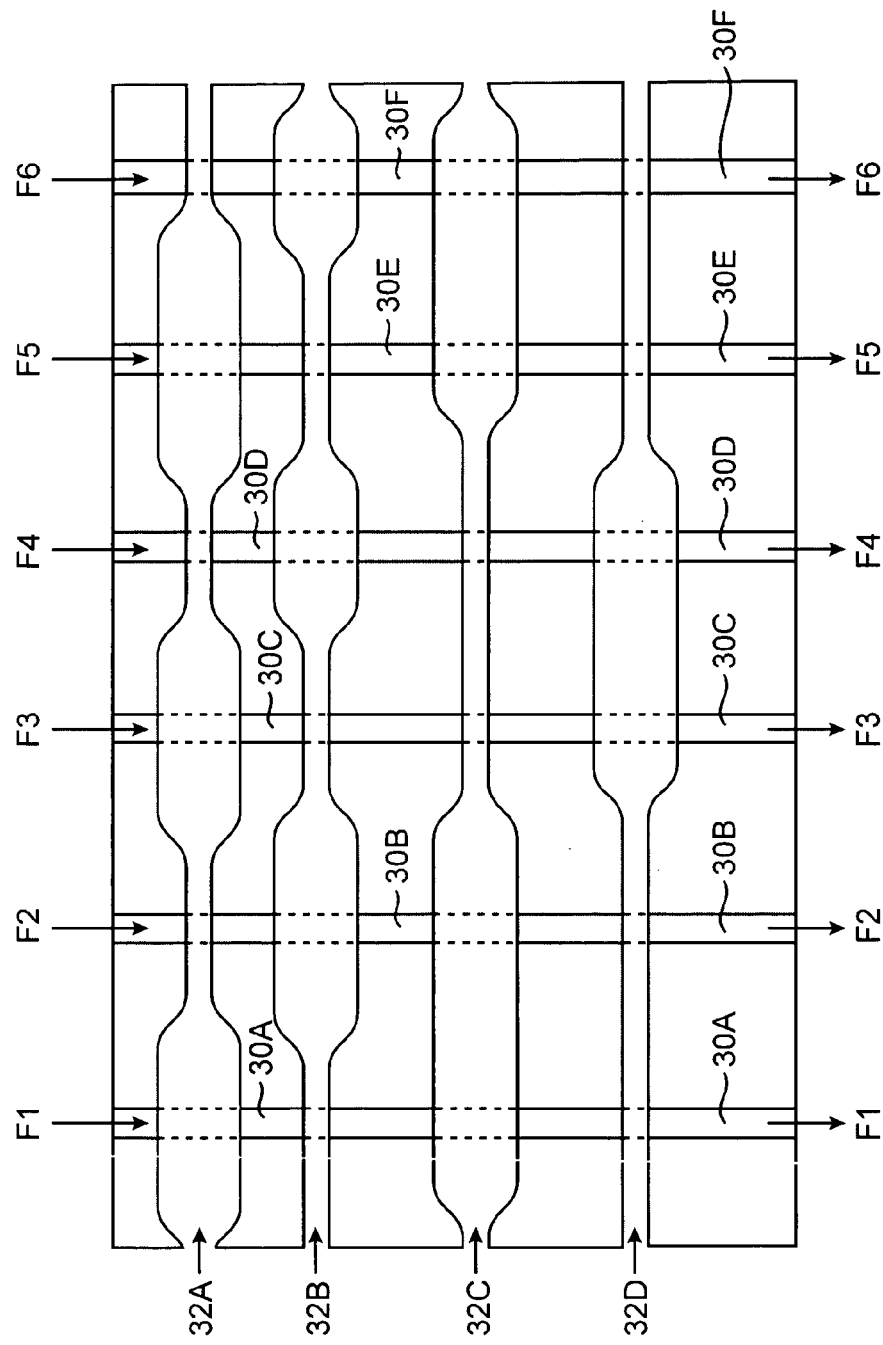
FIG. 16 is a schematic illustration of a multiplexed system adapted to permit flow through various channels.

FIGS. 12A and 12B show a views of a single on/off valve, identical to the systems set forth above, (for example in FIG. 7A). FIGS. 13A and 13B shows a peristaltic pumping system comprised of a plurality of the single addressable on/off valves as seen in FIG. 12, but networked together. FIG. 14 is a graph showing experimentally achieved pumping rates vs. frequency for the peristaltic pumping system of FIG. 13. FIGS. 15A and 15B show a schematic view of a plurality of flow channels which are controllable by a single control line. This system is also comprised of a plurality of the single addressable on/off valves of FIG. 12, multiplexed together, but in a different arrangement than that of FIG. 12. FIG. 16 is a schematic illustration of a multiplexing system adapted to permit fluid flow through selected channels, comprised of a plurality of the single on/off valves of FIG. 12, joined or networked together.

Referring first to FIGS. 12A and 12B, a schematic of flow channels 30 and 32 is shown. Flow channel 30 preferably has a fluid (or gas) flow F passing therethrough. Flow channel 32, (which crosses over flow channel 30, as was already explained herein), is pressurized such that membrane 25 separating the flow channels may be depressed into the path of flow channel 30, shutting off the passage of flow F therethrough, as has been explained. As such, "flow channel" 32 can also be referred to as a "control line" which actuates a single valve in flow channel 30. In FIGS. 12 to 15, a plurality of such addressable valves are joined or networked together in various arrangements to produce pumps, capable of peristaltic pumping, and other fluidic logic applications.

Referring to FIGS. 13A and 13B, a system for peristaltic pumping is provided, as follows. A flow channel 30 has a plurality of generally parallel flow channels (i.e.: control lines) 32A, 32B and 32C passing thereover. By pressurizing control line 32A, flow F through flow channel 30 is shut off under membrane 25A at the intersection of control line 32A and flow channel 30. Similarly, (but not shown), by pressurizing control line 32B, flow F through flow channel 30 is shut off under membrane 25B at the intersection of control line 32B and flow channel 30, etc.

Each of control lines 32A, 32B, and 32C is separately addressable. Therefore, peristalsis may be actuated by the pattern of actuating 32A and 32C together, followed by 32A, followed by 32A and 32B together, followed by 32B, followed by 32B and C together, etc. This corresponds to a successive "101, 100, 110, 010, 011, 001" pattern, where "0" indicates "valve open" and "1" indicates "valve closed." This peristaltic pattern is also known as a 120° pattern (referring to the phase angle of actuation between three valves). Other peristaltic patterns are equally possible, including 60° and 90° patterns.

In experiments performed by the inventors, a pumping rate of 2.35 nL/s was measured by measuring the distance traveled by a column of water in thin (0.5 mm i.d.) tubing; with 100×100×10 µm valves under an actuation pressure of 40 kPa. The pumping rate increased with actuation frequency until approximately 75 Hz, and then was nearly constant until above 200 Hz. The valves and pumps are also quite durable and the elastomer membrane, control channels, or bond have never been observed to fail. In experiments performed by the inventors, none of the valves in the peristaltic pump described herein show any sign of wear or fatigue after more than 4 million actuations. In addition to their durability, they are also gentle. A solution of E. Coli pumped through a channel and tested for viability showed a 94% survival rate.

FIG. 14 is a graph showing experimentally achieved pumping rates vs. frequency for the peristaltic pumping system of FIG. 13.

FIGS. 15A and 15B illustrates another way of assembling a plurality of the addressable valves of FIG. 12. Specifically, a plurality of parallel flow channels 30A, 30B, and 30C are provided. Flow channel (i.e.: control line) 32 passes thereover across flow channels 30A, 30B, and 30C. Pressurization of control line 32 simultaneously shuts off flows F1, F2 and F3 by depressing membranes 25A, 25B, and 25C located at the intersections of control line 32 and flow channels 30A, 30B, and 30C.

FIG. 16 is a schematic illustration of a multiplexing system adapted to selectively permit fluid to flow through selected channels, as follows. The downward deflection of membranes separating the respective flow channels from a control line passing thereabove (for example, membranes 25A, 25B, and 25C in FIGS. 15A and 15B) depends strongly upon the membrane dimensions. Accordingly, by varying the widths of flow channel control line 32 in FIGS. 15A and 15B, it is possible to have a control line pass over multiple flow channels, yet only actuate (i.e.: seal) desired flow channels. FIG. 16 illustrates a schematic of such a system, as follows.

A plurality of parallel flow channels 30A, 30B, 30C, 30D, 30E and 30F are positioned under a plurality of parallel control lines 32A, 32B, 32C, and 32D. Control channels 32A, 32B, 32C, and 32D are adapted to shut off fluid flows F1, F2, F3, F4, F5 and F6 passing through parallel flow channels 30A, 30B, 30C, 30D, 30E and 30F using any of the valving systems described above, with the following modification.

Each of control lines 32A, 32B, 32C, and 32D have both wide and narrow portions. For example, control line 32A is wide in locations disposed over flow channels 30A, 30C and 30E. Similarly, control line 32B is wide in locations disposed over flow channels 30B, 30D and 30F, and control line 32C is wide in locations disposed over flow channels 30A, 30B, 30E and 30F.

At the locations where the respective control line is wide, its pressurization will cause the membrane (25) separating the flow channel and the control line to depress significantly into the flow channel, thereby blocking the flow passage therethrough. Conversely, in the locations where the respective control line is narrow, membrane (25) will also be narrow. Accordingly, the same degree of pressurization will not result in membrane (25) becoming depressed into the flow channel (30). Therefore, fluid passage thereunder will not be blocked.

For example, when control line 32A is pressurized, it will block flows F1, F3 and F5 in flow channels 30A, 30C and 30E. Similarly, when control line 32C is pressurized, it will block flows F1, F2, F5 and F6 in flow channels 30A, 30B, 30E and 30F. As can be appreciated, more than one control line can be actuated at the same time. For example, control lines 32A and 32C can be pressurized simultaneously to block all fluid flow except F4 (with 32A blocking F1, F3 and F5; and 32C blocking F1, F2, F5 and F6).

By selectively pressurizing different control lines (32) both together and in various sequences, a great degree of fluid flow control can be achieved. Moreover, by extending the present system to more than six parallel flow channels (30) and more than four parallel control lines (32), and by varying the positioning of the wide and narrow regions of the control lines, very complex fluid flow control systems may be fabricated. A property of such systems is that it is possible to turn on any one flow channel out of n flow channels with only 2(log 2n) control lines.

8. Switchable Flow Arrays

Figure 17A:
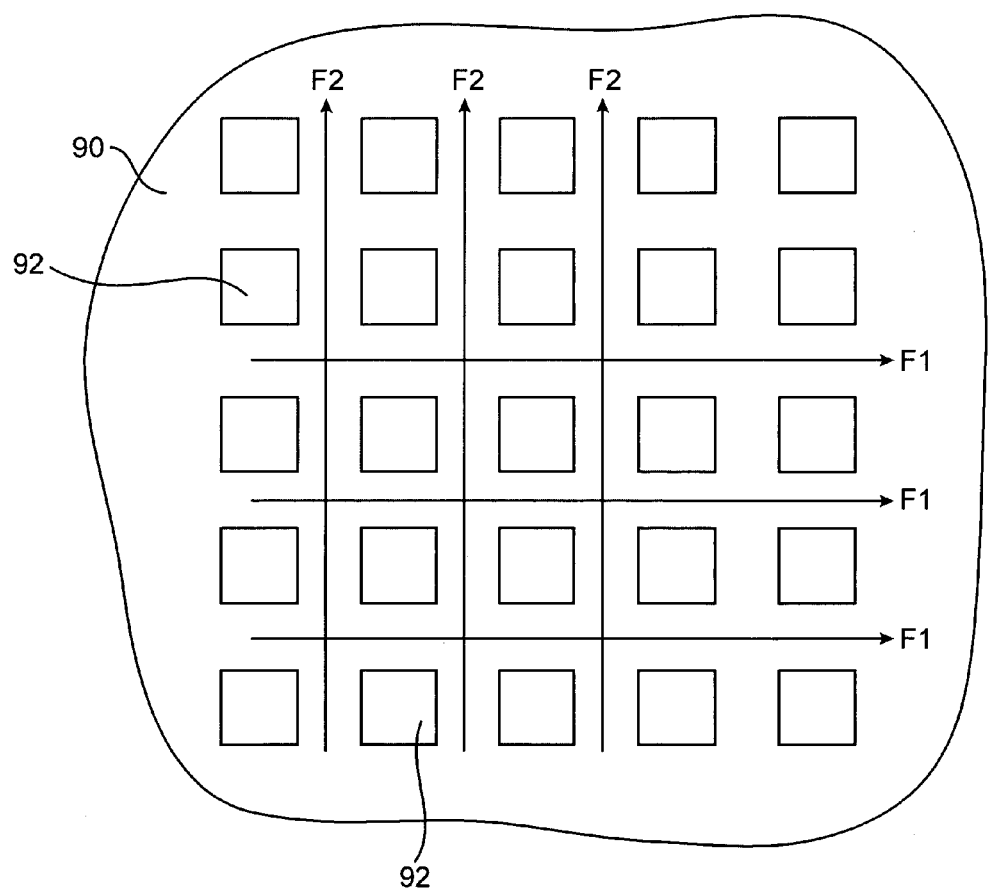
FIGS. 17A-D show plan views of one embodiment of a switchable flow array.

In yet another novel embodiment, fluid passage can be selectively directed to flow in either of two perpendicular directions. An example of such a "switchable flow array" system is provided in FIGS. 17A to 17D. FIG. 17A shows a bottom view of a first layer of elastomer 90, (or any other suitable substrate), having a bottom surface with a pattern of recesses forming a flow channel grid defined by an array of solid posts 92, each having flow channels passing therearound.

Figure 17B:
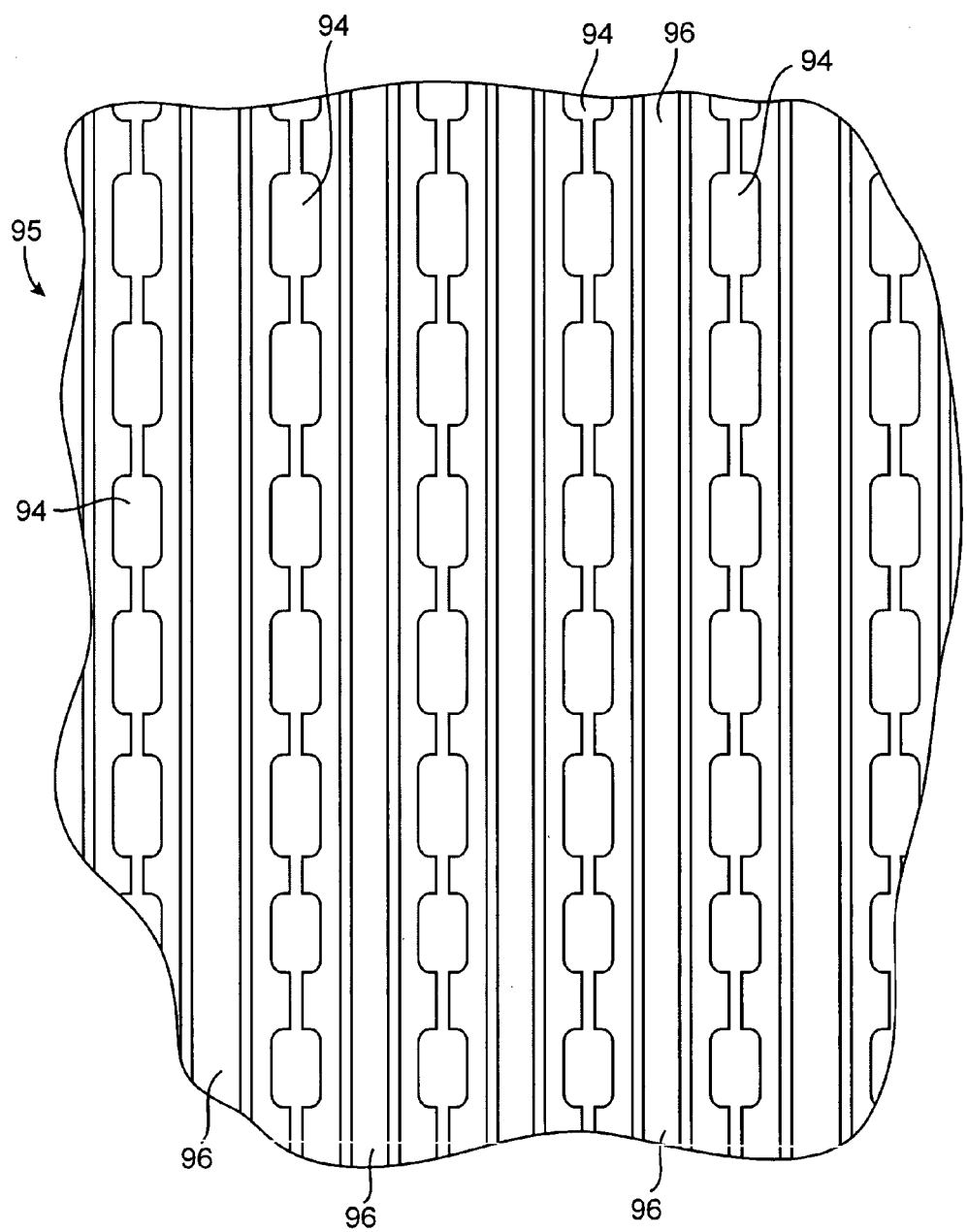

In preferred aspects, an additional layer of elastomer is bound to the top surface of layer 90 such that fluid flow can be selectively directed to move either in direction F1, or perpendicular direction F2. FIG. 17B is a bottom view of the bottom surface of the second layer of elastomer 95 showing recesses formed in the shape of alternating "vertical" control lines 96 and "horizontal" control lines 94. "Vertical" control lines 96 have the same width therealong, whereas "horizontal" control lines 94 have alternating wide and narrow portions, as shown.

Figure 17C:
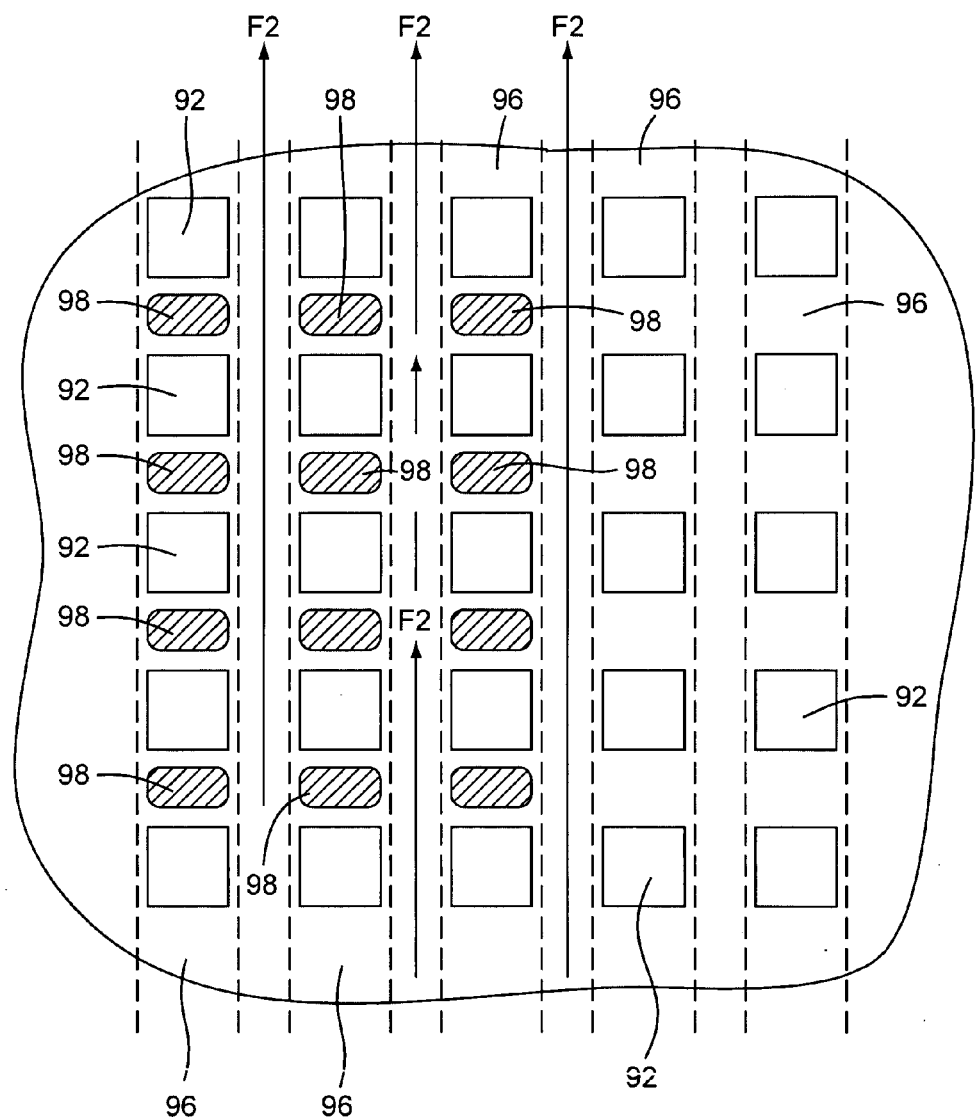
Figure 17D:
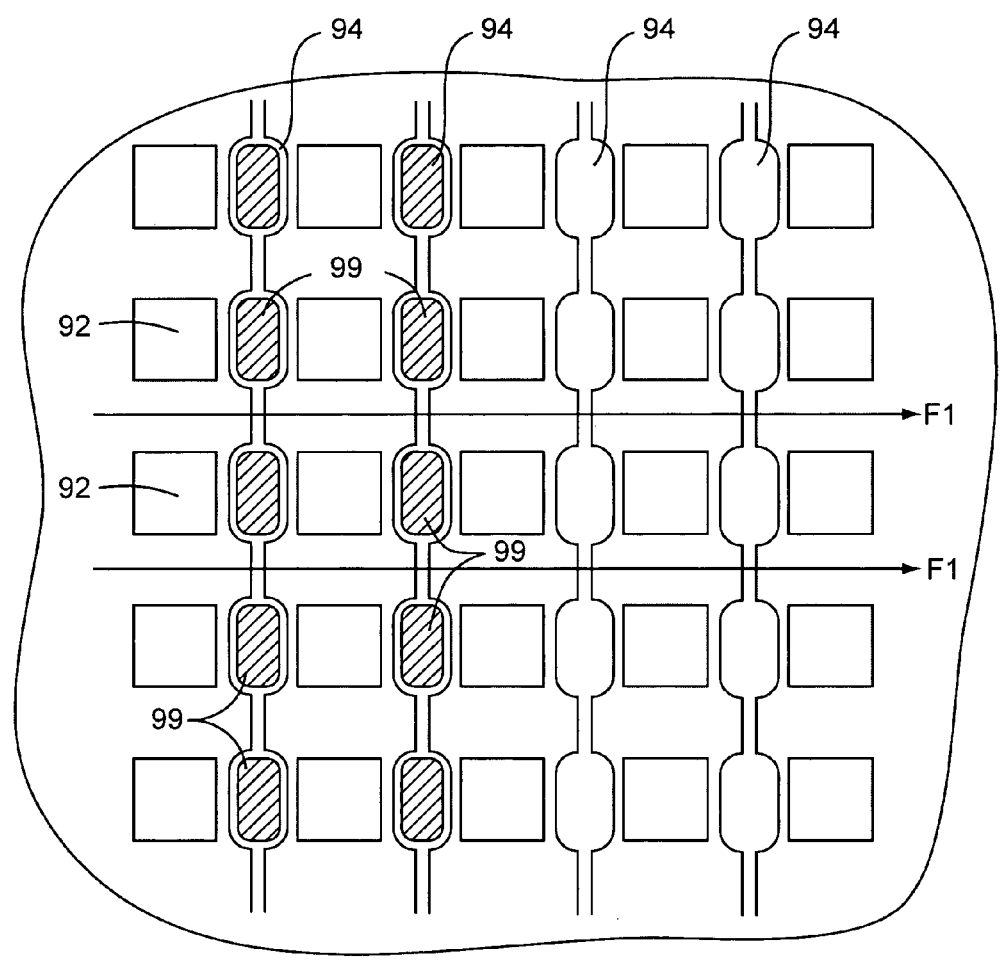

Elastomeric layer 95 is positioned overtop of elastomeric layer 90 such that "vertical" control lines 96 are positioned over posts 92 as shown in FIG. 17C and "horizontal" control lines 94 are positioned with their wide portions between posts 92, as shown in FIG. 17D.

As can be seen in FIG. 17C, when "vertical" control lines 96 are pressurized, the membrane of the integrated structure formed by the elastomeric layer initially positioned between layers 90 and 95 in regions 98 will be deflected downwardly over the array of flow channels such that flow in only able to pass in flow direction F2 (i.e.: vertically), as shown.

As can be seen in FIG. 17D, when "horizontal" control lines 94 are pressurized, the membrane of the integrated structure formed by the elastomeric layer initially positioned between layers 90 and 95 in regions 99 will be deflected downwardly over the array of flow channels, (but only in the regions where they are widest), such that flow in only able to pass in flow direction F1 (i.e.: horizontally), as shown.

The design illustrated in FIGS. 17A-D allows a switchable flow array to be constructed from only two elastomeric layers, with no vertical vias passing between control lines in different elastomeric layers required. If all vertical flow control lines 94 are connected, they may be pressurized from one input. The same is true for all horizontal flow control lines 96.

9. Cell Pen

In yet a further application of the present invention, an elastomeric structure can be utilized to manipulate organisms or other biological material. FIGS. 18A-18D show plan views of one embodiment of a cell pen structure in accordance with the present invention.

Cell pen array 4400 features an array of orthogonally-oriented flow channels 4402, with an enlarged "pen" structure 4404 at the intersection of alternating flow channels. Valve 4406 is positioned at the entrance and exit of each pen structure 4404. Peristaltic pump structures 4408 are positioned on each horizontal flow channel and on the vertical flow channels lacking a cell pen structure.

Figure 18A:
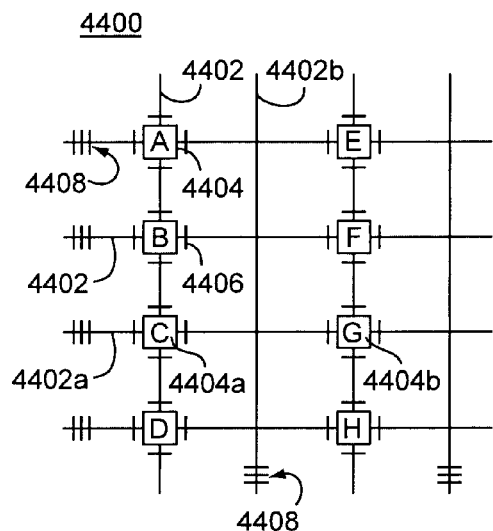
FIGS. 18A-D show plan views of one embodiment of a cell pen array structure.
Figure 18C:
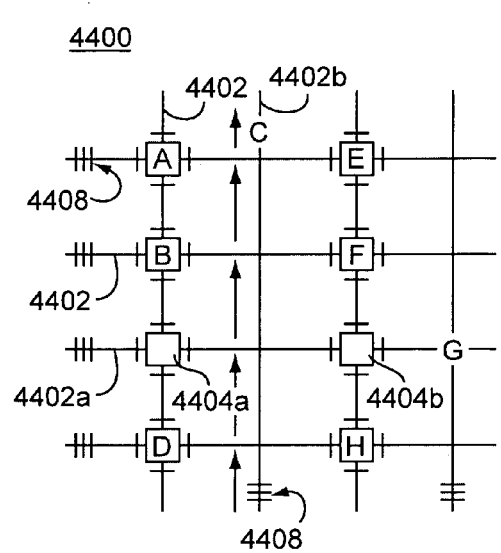
Figure 18B:
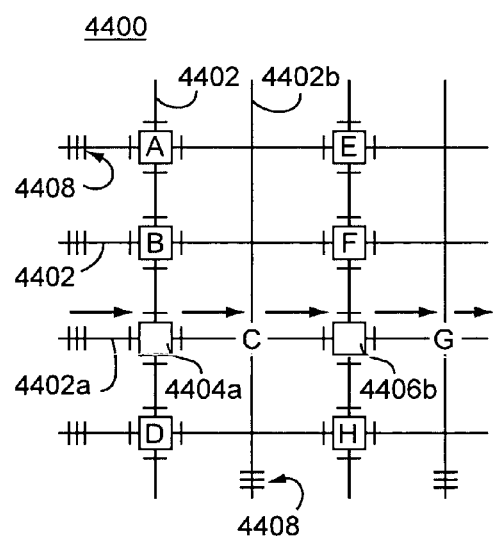
Figure 18D:
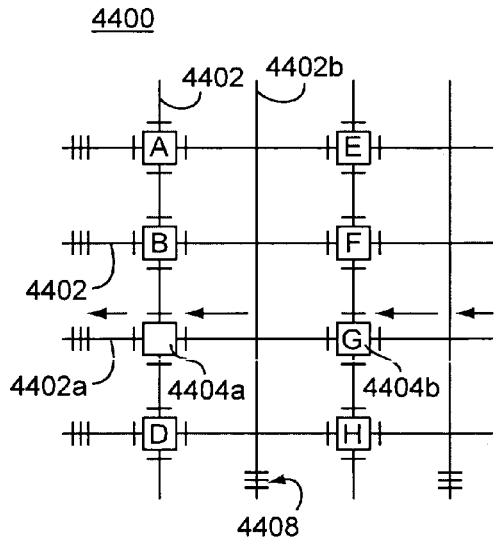

Cell pen array 4400 of FIG. 18A has been loaded with cells A-H that have been previously sorted. FIGS. 18B-18C show the accessing and removal of individually stored cell C by 1) opening valves 4406 on either side of adjacent pens 4404a and 4404b, 2) pumping horizontal flow channel 4402a to displace cells C and G, and then 3) pumping vertical flow channel 4402b to remove cell C. FIG. 18D shows that second cell G is moved back into its prior position in cell pen array 4400 by reversing the direction of liquid flow through horizontal flow channel 4402a. The cell pen array 4404 described above is capable of storing materials within a selected, addressable position for ready access.

While the embodiment shown and described above in connection with FIGS. 18A-18D utilizes linked valve pairs on opposite sides of the flow channel intersections, this is not required by the present invention. Other configurations, including linking of adjacent valves of an intersection, or independent actuation of each valve surrounding an intersection, are possible to provide the desired flow characteristics. With the independent valve actuation approach however, it should be recognized that separate control structures would be utilized for each valve, complicating device layout.

10. Cell Cage

The cell pen array 4404 described above is capable of storing materials within a selected, addressable position for ready access. However, living organisms such as cells may require a continuous intake of foods and expulsion of wastes in order to remain viable. Accordingly, FIGS. 19A and 19B show plan and cross-sectional views (along line 45B-45B') respectively, of one embodiment of a cell cage structure in accordance with the present invention.

Cell cage 4500 is formed as an enlarged portion 4500a of a flow channel 4501 in an elastomeric block 4503 in contact with substrate 4505. Cell cage 4500 is similar to an individual cell pen as described above in FIGS. 18A-18D, except that ends 4500b and 4500c of cell cage 4500 do not completely enclose interior region 4500a. Rather, ends 4500a and 4500b of cage 4500 are formed by a plurality of retractable pillars 4502.

Specifically, control channel 4504 overlies pillars 4502. When the pressure in control channel 4504 is reduced, elastomeric pillars 4502 are drawn upward into control channel 4504, thereby opening end 4500b of cell cage 4500 and permitting a cell to enter. Upon elevation of pressure in control channel 4504, pillars 4502 relax downward against substrate 4505 and prevent a cell from exiting cage 4500.

Elastomeric pillars 4502 are of a sufficient size and number to prevent movement of a cell out of cage 4500, but also include gaps 4508 which allow the flow of nutrients into cage interior 4500a in order to sustain cell(s) stored therein. Pillars 4502 on opposite end 4500c are similarly configured beneath second control channel 4506 to permit opening of the cage and removal of the cell as desired.

11. Cross-Channel Injector

The cross-flow channel architecture illustrated shown in FIGS. 18A-18D can be used to perform functions other than the cell pen just described. For example, the cross-flow channel architecture can be utilized in mixing applications.

This is shown in FIGS. 20A-D, which illustrate a plan view of mixing steps performed by a microfabricated structures in accordance another embodiment of the present invention. Specifically, portion 7400 of a microfabricated mixing structure comprises first flow channel 7402 orthogonal to and intersecting with second flow channel 7404. Control channels 7406 overlie flow channels 7402 and 7404 and form valve pairs 7408a-b and 7408c-d that surround each intersection 7412.

As shown in FIG. 20A, valve pair 7408c-d is initially opened while valve pair 7408a-b is closed, and fluid sample 7410 is flowed to intersection 7412 through flow channel 7404. Valve pair 7408a-b is then actuated, trapping fluid sample 7410 at intersection 7412.

Next, as shown in FIG. 20B, valve pairs 7408c-d are closed and 7408a-b are opened, such that fluid sample 7410 is injected from intersection 7412 into flow channel 7402 bearing a cross-flow of fluid. The process shown in FIGS. 20A-B can be repeated to accurately dispense any number of fluid samples down cross-flow channel 7402.

While the embodiment of a process-channel flow injector structure shown in FIGS. 20A-B feature channels intersecting at a single junction, this is not required by the present invention. Thus FIG. 20C shows a simplified plan view of another embodiment of an injection structure in accordance with the present invention, wherein junction 7450 between intersecting flow channels 7452 is extended to provide additional volume capacity. FIG. 20D shows a simplified plan view of yet another embodiment of an injection structure in accordance with the present invention, wherein elongated junction 7460 between intersecting flow channels 7462 includes branches 7464 to provide still more injection volume capacity.

12. Rotary Mixing Structure

Microfluidic control and flow channels in accordance with embodiments of the present invention may be oriented to rotary pump design which circulates fluid through a closed circuit flow channel. As used herein the term "closed circuit" has the meaning known in the art and refers to configurations that are circular and variations thereof such as ellipsoids and ovals, as well as flow circuit paths having corners or as are created by triangular, rectangular, or more complex shapes.

Figure 21:
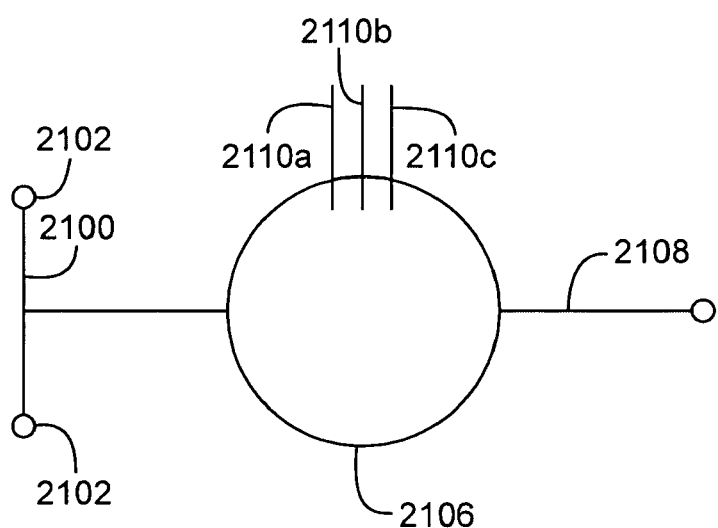
FIG. 21 shows a plan view of one embodiment of a rotary mixing structure in accordance with the present invention.

As illustrated in FIG. 21, a layer with flow channels 2100 has a plurality of sample inputs 2102, a mixing T-junction 2104, a central circulation loop 2106 (i.e., the substantially circular flow channel), and an output channel 2108. The overlay of control channels with a flow channel can form a microvalve. This is so because the control and flow channels are separated by a thin elastomeric membrane that can be deflected into the flow channel or retracted therefrom.

The substantially circular central loop and the control channels that intersect with it form the central part of the rotary pump. The pump(s) which cause solution to be flowed through the substantially circular flow channel consist of a set of at least three control channels 2110a-c that are adjacent to one another and which intersect the substantially circular branch flow channel 2106 (i.e., the central loop).

When a series of on/off actuation sequences, such a 001, 011, 010, 110, 100, 101, are applied to the control channels, the fluid in the central loop can be peristaltically pumped in a chosen direction, either clockwise or counterclockwise. The peristaltic pumping action results from the sequential deflection of the membranes separating the control channels and flow channel into or out of the flow channel.

In general, the higher the actuation frequency, the faster the fluid rotates through the central loop. However, a point of saturation may eventually be reached at which increased frequency does not result in faster fluid flow. This is primarily due to limitations in the rate at which the membrane can return to an unactuated position.

While the system shown in FIG. 21 shows each pump including three control channels, a different number of control channels can be utilized, for example, a single serpentine control channel having multiple cross-over points could be used.

A variety of different auxiliary flow channels which are in fluid communication with the central loop can be utilized to introduce and withdrawn sample and reactant solutions from the central loop. Similarly, one or more exit or outlet flow channels in fluid communication with the central loop can be utilized to remove solution from the central loop. For example, control valves can be utilized at the inlet(s) and the outlet(s) to prevent solution flow into or out from the central loop.

Flow channel sizes and shapes can vary. With certain devices, the diameter of the channel tends to range from about 1 mm to 2 cm, although the diameter can be considerably larger in certain devices (e.g., 4, 6, 8, or 10 cm). Limits on how small the diameter of the circular flow channel can be are primarily a function of the limits imposed by the multilayer soft lithography processes. Channel widths (either flow or control) usually vary between 30 µm and 250 µm. However, channel width in some devices is as narrow as 1 um. Channels of larger widths can also be utilized, but generally require some type of structural support within the flow channel. Channel height generally varies between 5 and 50 µm. In flow channels having a width of 100 µm or less, the channel height may be 1 µm or smaller. The flow channel is typically rounded to allow for complete blockage of the channel once the membrane is deflected into the channel. In some devices, the channels have shapes such as octagons or hexagons. In certain devices, the flow channels are rounded and 100 µm wide and 10 µm high and control channels are 100 µm wide and 10 µm high. One system that has been utilized in certain studies has utilized a central loop having a diameter of 2 cm, a flow channel width of 100 µm and a depth of 10 µm.

While the channels typically have the foregoing sizes and shapes, it should be recognized that the devices provided herein are not limited to these particular sizes and shapes. For example, branches present in a closed circuit flow channel may serve to control the dispersion and hence mixing of materials flowed therein.

13. Microfluidic Large-Scale Integration

The previous section has described monolithic microvalves that are substantially leakproof and scalable, and has also described methods for fabricating these microvalves. For the relatively simple assemblies of microfluidic valves previously described, each fluid flow channel may be controlled by its own individual valve control channel. However, such a non-integrated control strategy cannot be practicably implemented for more complex assemblies comprising thousands or even tens of thousands of individually addressable valves. Accordingly, a variety of techniques may be applied alone or in combination to allow for the fabrication of large scale integrated microfluidic devices having individually addressable valves.

Techniques useful for implementing large scale integrated microfluidic structures in accordance with embodiments of the present invention are discussed in detail in pending U.S. nonprovisional patent application No. 10/670,997. One technique allowing for the fabrication of large scale int microfluidic devices is the use of multiplexor structures.

Figure 22A:
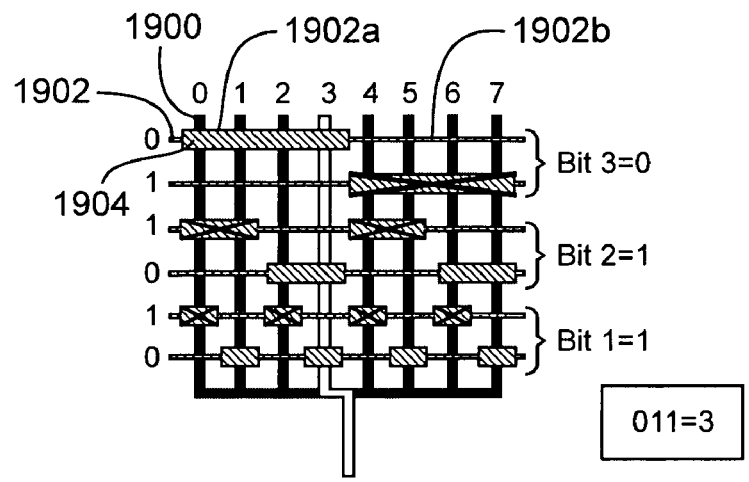
FIG. 22A shows a simplified plan view illustrating a binary tree microfluidic multiplexor operational diagram.

The use of multiplexor structures has previously been described in connection with a single set of control lines overlying a single set of flow channels. FIG. 22A shows a simplified plan view illustrating a microfluidic binary tree multiplexor operational diagram. Flow channels 1900 defined in a lower elastomer layer contain the fluid of interest, while control channels 1902 defined in an overlying elastomer layer represent control lines containing an actuation fluid such as air or water. Valves 1904 are defined by the membranes formed at the intersection of the wider portion 1902a of a control channel 1902 with a flow channel 1900. The actuation pressure is chosen so that only the wide membranes are fully deflected into the flow channel 1900. Specifically, the multiplexor structure is based on the sharp increase in pressure required to actuate a valve as the ratio of control channel width: flow channel width is decreased.

The multiplexor structure shown in FIG. 22A is in the form of a binary tree of valves where each stage selects one out of two total groups of flow channels. In the multiplexor embodiment shown in FIG. 22A, each combination of open/closed valves in the multiplexor selects for a single channel, so that n flow channels can be addressed with only 2 $\log_2$ n control channels.

By using multiplexed valve systems, the power of the binary system becomes evident: only about 20 control channels are required to specifically address 1024 flow channels. This allows a large number of elastomeric microvalves to perform complex fluidic manipulations within these devices, while the interface between the device and the external environment is simple and robust.

Figure 22B:
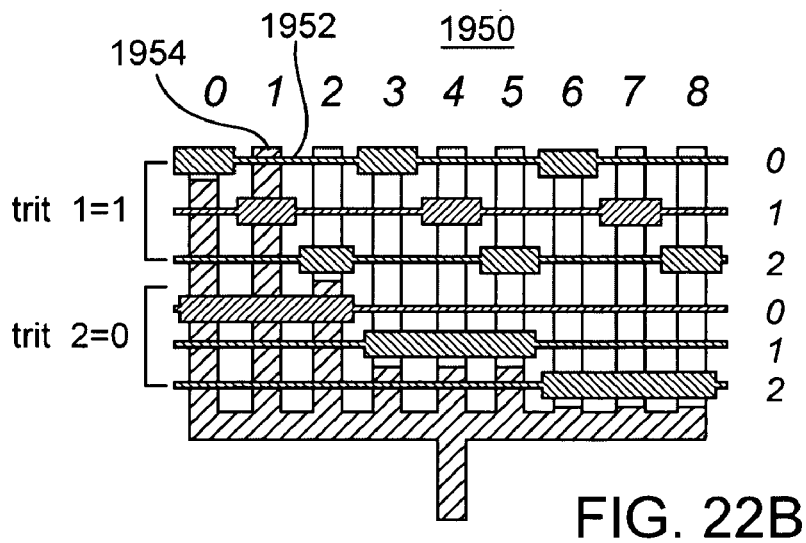
FIG. 22B shows a simplified plan view illustrating a tertiary tree microfluidic multiplexor operational diagram.

FIG. 22B shows a simplified plan view of an alternative embodiment of a multiplexor structure in accordance with the present invention. Multiplexor structure 1950 comprises control channels 1952 formed in an elastomer layer overlying flow channels 1954 of an underlying elastomer layer. Operating under the same physical principles of the multiplexor of FIG. 22A, multiplexor 1950 comprises a tertiary tree of valves, where each stage comprises three bits ("a trit") and selects one out of three total groups of flow channels. Each combination of open/closed valves in the multiplexor 1950 selects for a single channel, so that n flow channels can be addressed with only 3 $\log_3$ n control channels.

Figure 22C:
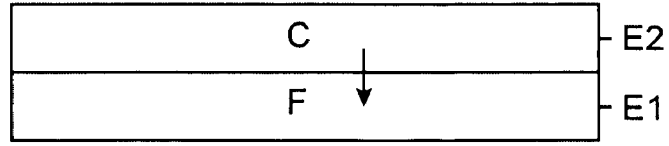
FIG. 22C shows a simplified cross-sectional view of the general microfluidic architecture of the devices of FIGS. 22A-B.

The general microfluidic flow architecture of either of the basic multiplexor devices shown in FIGS. 22A-B may be generically represented in the simplified cross-sectional view of FIG. 22C, wherein second elastomer layer E2 defining control channel network C overlies first elastomer layer E1 defining flow channel network F.

The base 3 multiplexor of FIG. 22B is the most efficient design that may be used to address large numbers of "flow" channels. This is because the x $\log_x$ n valve is minimized where e is used for the base of the log. As fractions are not used for the base of an actual multiplexor, the most efficient multiplexor structure is achieved where the value of x=3, the integer closest to e (~2.71828).

To highlight this point, TABLE 2 compares the efficiency of the base 2 multiplexor with the base 3 multiplexor.

TABLE 2

| Number of Control Lines | Number of Flow Lines Controlled by Control Lines | | Enhanced Efficiency of Base 3 Multiplexor Structure |
| --- | --- | --- | --- |
| | Base 2 Multiplexor | Base 3 Multiplexor | |
| 6 | 8 | 9 | +1 |
| 9 | 23 | 27 | +4 |
| 12 | 64 | 81 | +17 |
| 15 | 181 | 243 | +62 |
| 18 | 512 | 729 | +217 |

While the above description has focused upon various multiplexor structures utilizing stages having the same base number, this is not required by the present invention. Alternative embodiments of multiplexor structures in accordance with the present invention may comprise stages of unlike base numbers. For example, a two-stage multiplexor consisting of a bit stage and a trit stage represents the most efficient way of addressing six flow channels. The order of the stages is arbitrary, and will always result in the same number of flow lines being controlled. The use of multiplexor structures comprising different binary and tertiary stages allows the efficient addressing of any number of "flow" channels that are the product of the numbers 2 and 3.

Figure 23:
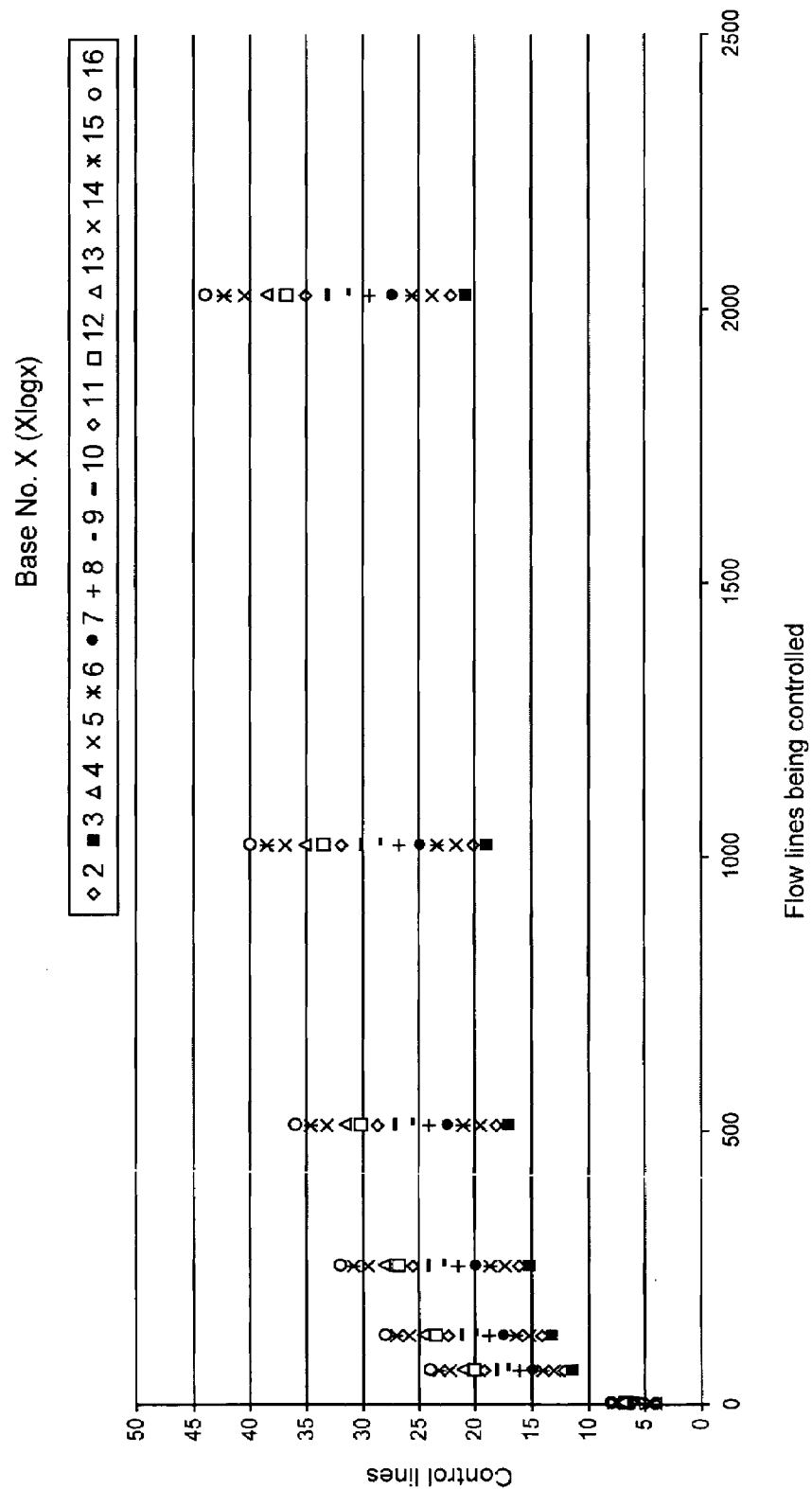
FIG. 23 plots the number of control lines versus the number of flow lines being controlled, for multiplexors of various base numbers.

A multiplexor may conceivably use any base number. For example, five may also be used as the base number, if necessary. However, efficiency in utilization of control lines diminishes as the number of control lines moves away from the value of e. This is shown in FIG. 23, which plots the number of control lines versus the number of flow lines being controlled, for multiplexor structures having different base numbers.

Figure 24:
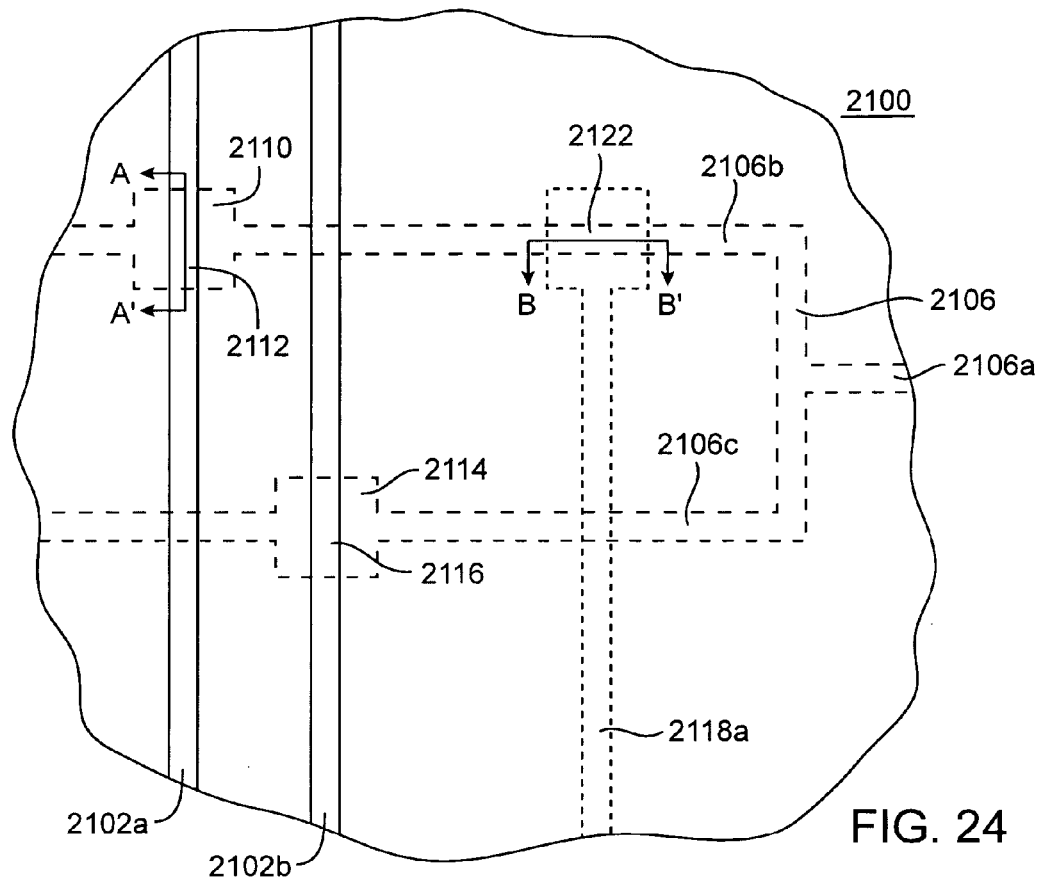
FIG. 24 shows a simplified plan view of an embodiment of a microfluidic structure utilizing control channels to control other control channels.
Figure 24A:
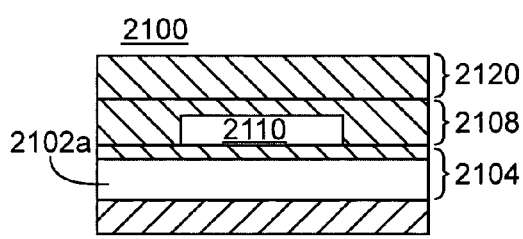
FIG. 24A shows a simplified cross-sectional view of the structure of FIG. 24 taken along the line A-A'
Figure 24B:
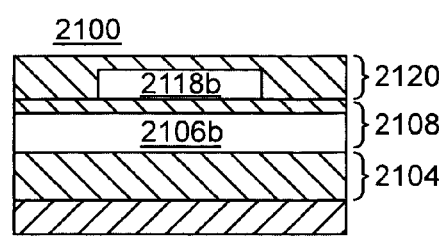
FIG. 24B shows a simplified cross-sectional view of the structure of FIG. 24 taken along the line B-B'.

Another technique allowing for the fabrication of large scale integrated (LSI) microfluidic devices is the use of multiple layers of control lines. FIGS. 24-24B illustrate this approach. FIG. 24 shows a plan view of one embodiment of a microfluidic device having a first control line controlled by a second control line. FIG. 24A shows a cross-sectional view of the microfluidic device of FIG. 24, taken along line A-A'. FIG. 24B shows a cross-sectional view of the microfluidic device of FIG. 24, taken along line B-B'.

Microfluidic structure 2100 comprises two flow channels 2102*a-b* formed in lowermost elastomer layer 2104. First control channel network 2106 including first inlet 2106*a* in fluid communication with first and second branches 2106*b* and 2106*c*, is formed in a second elastomer layer 2108 overlying first elastomer layer 2104. First branch 2106*b* of first control channel network 2106 includes widened portion 2110 overlying first flow channel 2102*a* to define first valve 2112. Second branch 2106*c* of first control channel network 2106 includes widened portion 2114 overlying second flow channel 2102*b* to define second valve 2116.

Second control channel network 2118 comprising third control channel 2118*a* is formed in third elastomer layer 2120 overlying second elastomer layer 2108. Third control channel 2118*a* includes widened portion 2118*b* overlying first branch 2106*b* of first control channel network 2106 to form valve 2122.

The microfluidic device illustrated in FIGS. 24-24B may be operated as follows. A fluid that is to be manipulated is present in flow channels 2102*a* and 2102*b*. Application of a pressure to the first control channel network 2106 causes the membranes of valves 2112 and 2116 to deflect downward into their respective flow channels 2102*a* and 2102*b*, thereby valving flow through the flow channels.

Application of a pressure to second control channel network 2118 causes the membrane of valve 2122 to deflect downward into underlying first branch 2106*c* only of first control channel network 2106. This fixes the valve 2112 in its deflected state, in turn allowing the pressure within the first control channel network 2106 to be varied without affecting the state of valve 2112.

Figure 25:
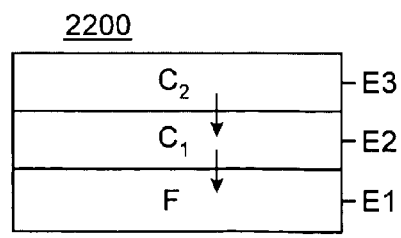
FIG. 25 shows a simplified cross-sectional view of the general microfluidic architecture of the device of FIGS. 24-24B.

The general architecture of the microfluidic device depicted in FIGS. 24-24B is summarized in the simplified cross-sectional view of FIG. 25. Specifically, elastomeric device 2200 comprises lowest elastomer layer E1 defining flow channel network F, underlying second elastomer layer E2 defining first control channel network C1. First control channel network C1 in turn underlies second control channel network C2 that is defined within third elastomer layer E3.

While the embodiment of the microfluidic device of FIGS. 24-24B is described as being fabricated from three separate elastomer layers, this is not required by the present invention. Large scale integrated microfluidic structures in accordance with embodiments of the present invention featuring multiplexed control lines may be fabricated utilizing only two elastomer layers. This approach is shown and illustrated in connection with FIGS. 26-26B.

FIG. 26 shows a simplified plan view of a microfabricated elastomer device including first and second flow channels 2300*a* and 2300*b*, and first branched control channel network 2302 overlying flow channels 2300*a* and 2300*b* to define valves 2304 and 2306 respectively. FIG. 26A shows a cross-sectional view of the microfabricated elastomer device of FIG. 26, taken along line A-A', with flow channel 2300a defined in lower elastomer layer 2308, and first control channel 2302 defined in upper elastomer layer 2310.

Lower elastomer layer 2308 further comprises a second control channel network 2312 running underneath first control channel 2302 to define valve 2314. Accordingly, FIG. 26B shows a cross-sectional view of the microfabricated elastomer device of FIG. 26, taken along line B-B'. While present in the same (lower) elastomer layer 2308, flow channel network 2300 and second control channel network 2312 are separate and do not intersect one another.

As represented in the simplified cross-sectional view of FIG. 27, separate flow channel network F and control channel network C2 may thus be present on a single (lower) elastomer layer E1 that is overlaid by another elastomer layer E2 defining only a control channel network C1.

The microfluidic device illustrated in FIGS. 26-26B may be operated as follows. A fluid that is to be manipulated is present in flow channels 2300a and 2300b. Application of a pressure to the first control channel network 2302 causes the membranes of valves 2304 to deflect downward into their respective flow channels 2300a and 2300b, thereby valving flow through the flow channels.

Application of a pressure to second control channel network 2312 causes the membrane of valve 2314 to deflect upward into the overlying branch of first control channel network 2302. This fixes the valve 2314 in its deflected state, in turn allowing the pressure within the first control network 2302 to be varied without affecting the state of valve 2314. In contrast with the embodiment shown in FIG. 24, the microfluidic device of FIGS. 26-26B features a valve that operates by deflecting upward into an adjacent control channel in response to an elevated pressure.

Figure 27A:
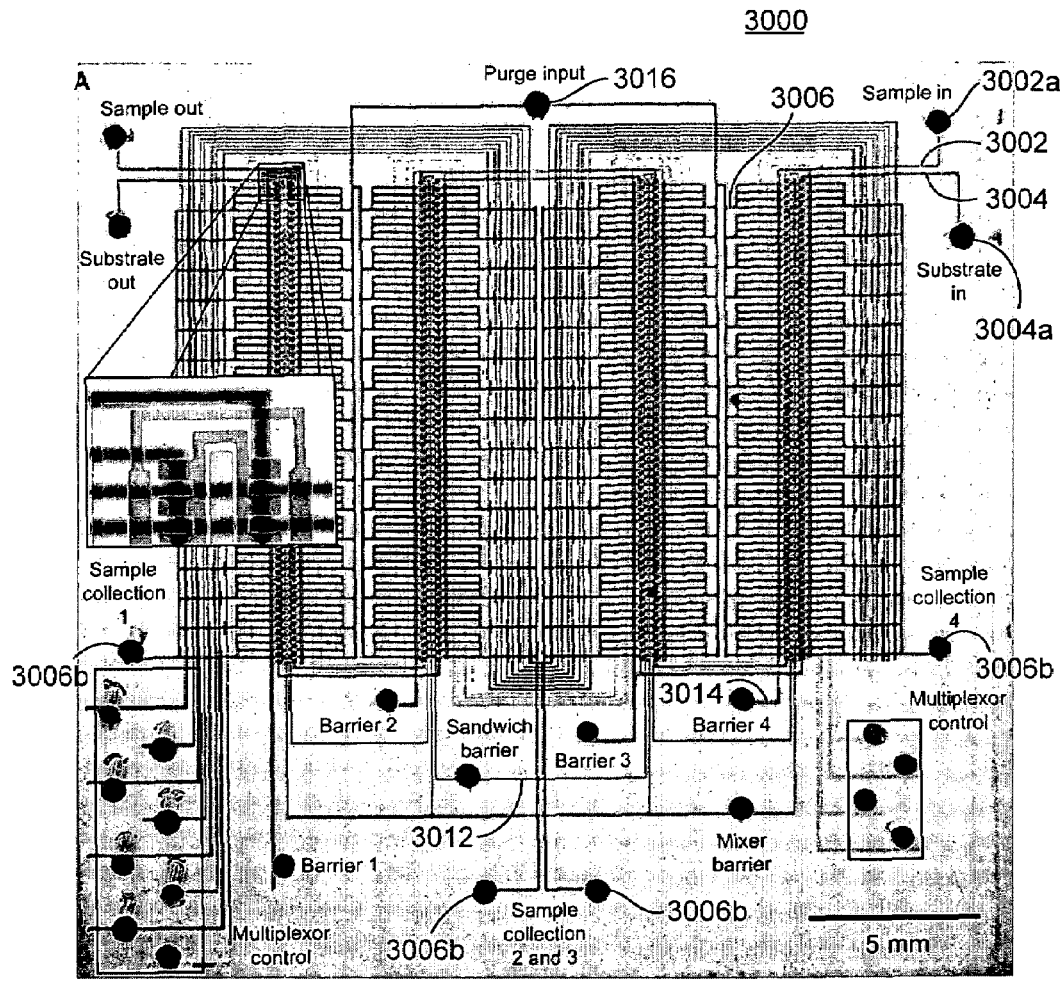
FIG. 27A shows an optical micrograph of a microfluidic comparator chip.
Figure 27B:
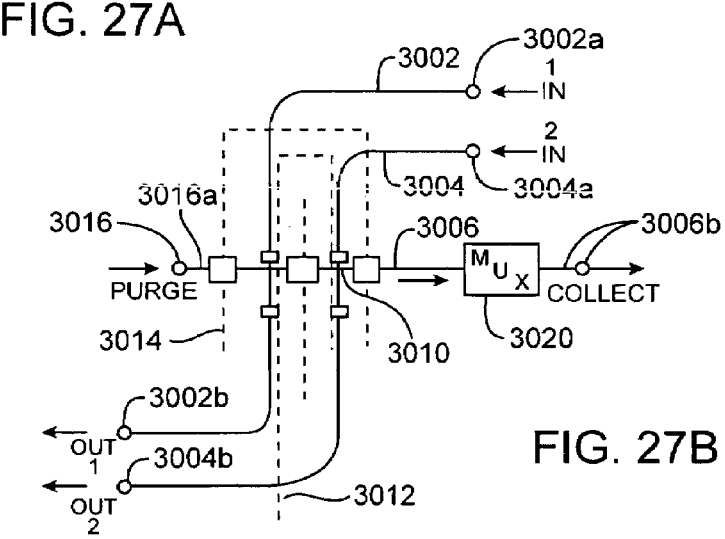
FIG. 27B is a simplified schematic view of the microfluidic comparator chip of FIG. 27A.

FIG. 27A shows an optical micrograph of a microfluidic comparator chip 3000 microfabricated with large scale integration technology which is analogous to an array of 256 comparators. Specifically, a second device containing 2056 microvalves was designed which is capable of performing more complex fluidic manipulations. The various inputs have been loaded with colored food dyes to visualize the channels and sub-elements of the fluidic logic. FIG. 27B shows a simplified schematic plan view of one portion of the chip of FIG. 27A.

Comparator chip 3000 is formed from a pair of parallel, serpentine flow channels 3002 and 3004 having inlets 3002a and 3004a respectively, and having outlets 3002b and 3004b respectively, that are intersected at various points by branched horizontal rows of flow channels 3006. Portions of the horizontal flow channels located between the serpentine flow channels define mixing locations 3010.

A first barrier control line 3012 overlying the center of the connecting channels is actuable to create adjacent chambers, and is deactivable to allow the contents of the adjacent chambers to mix. A second barrier control line 3014 doubles back over either end of the adjacent chambers to isolate them from the rest of the horizontal flow channels.

One end 3006a of the connecting horizontal flow channel 3006 is in fluid communication with pressure source 3016, and the other end 3006b of the connecting horizontal flow channel 3006 is in fluid communication with a sample collection output 3018 through multiplexor 3020.

Figure 27C:
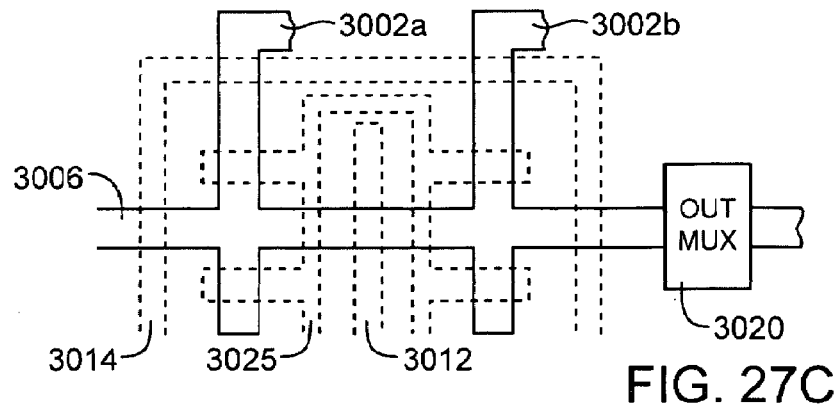
FIGS. 27C-H are enlarged simplified plan views showing loading of the chamber of the microfluidic structure of FIG. 27A.
Figure 27D:
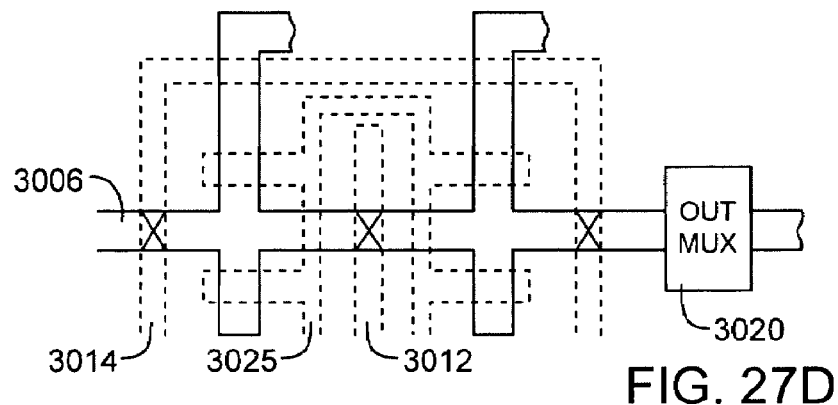
Figure 27E:
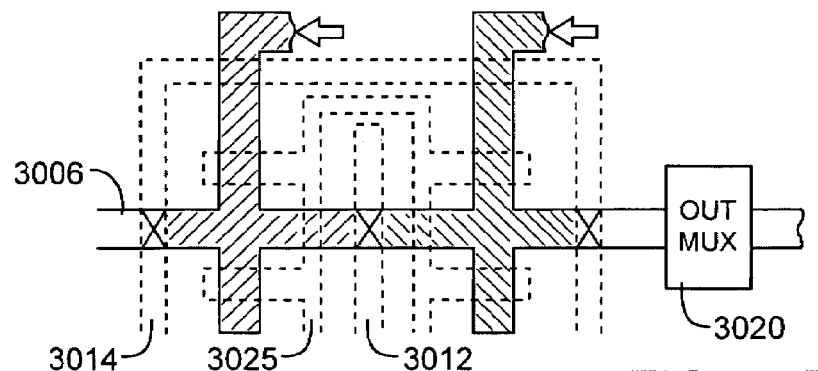
Figure 27F:
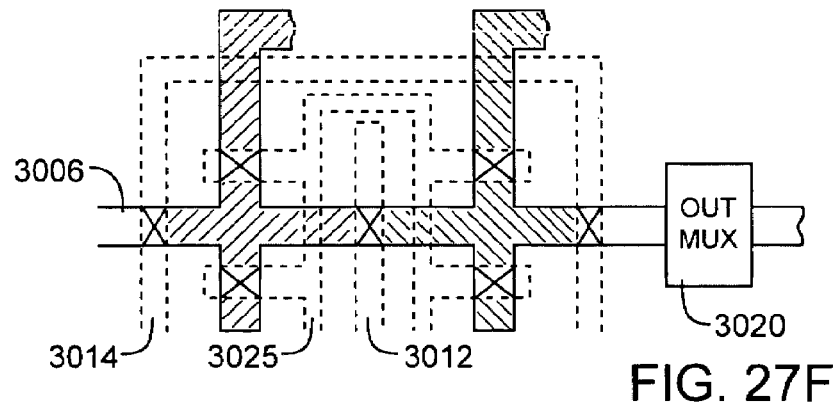

FIGS. 27C-H show simplified enlarged plan views of operation of one mixing element of the structure of FIGS. 27A-B. FIG. 27C shows the mixing element prior to loading, with the mixer barrier control line and wrap-around barrier control line unpressurized. FIG. 27D shows pressurization of the wrap-around barrier control line and barrier mixer line to activate isolation valves and separation valve to define adjacent chambers 3050 and 3052. FIG. 27E shows loading of the chambers with a first component and a second component by flowing these materials down the respective flow channels. FIG. 27F shows pressurization of the vertical compartmentalization control line 3025 and the isolation to define the adjacent chambers.

Figure 27G:
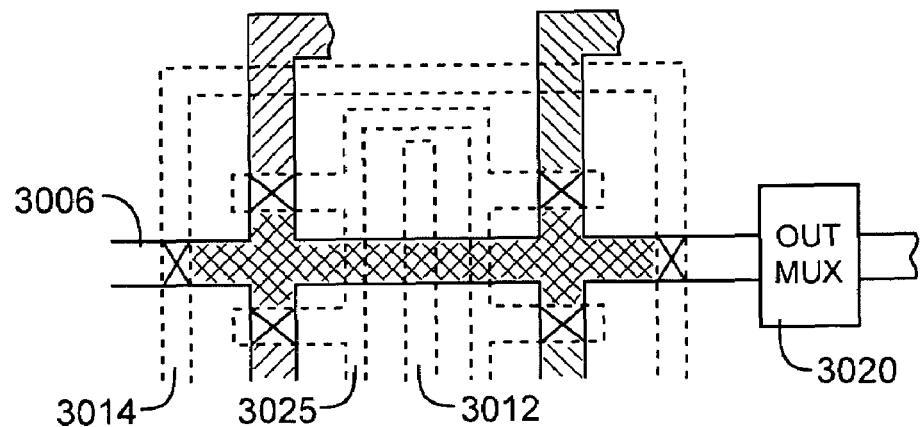

FIG. 27G shows depressurization of the mixing barrier control channel to deactivate the separation barrier valve, thereby allowing the different components present in the adjacent chambers to mix freely.

Figure 27H:
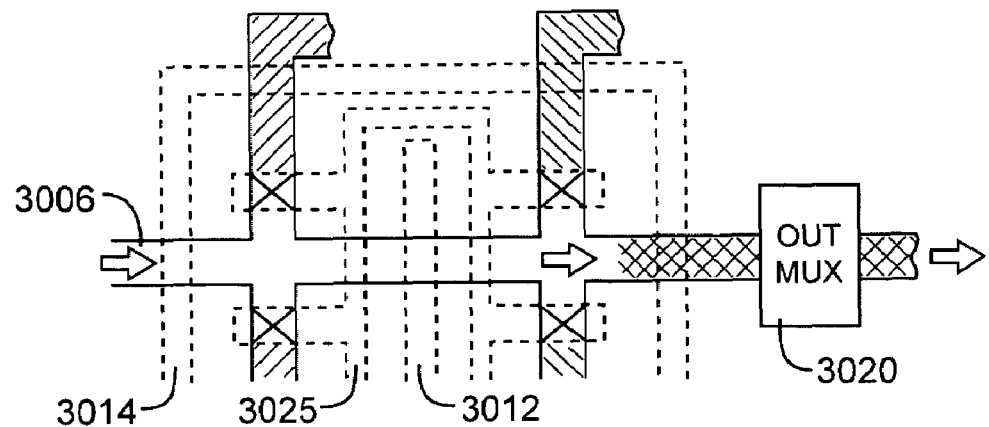

FIG. 27H shows the deactivation of barrier the isolation control line, causing deactivation of the isolation valves, followed by application of pressure to the control line and deactivation of the multiplexor to allow the combined mixture to be recovered.

In the case of the device shown in FIGS. 27A-H, two different reagents can be separately loaded, mixed pair wise, and selectively recovered, making it possible to perform distinct assays in 256 sub-nanoliter reaction chambers and then recover a particularly interesting reagent. The microchannel layout consists of four central columns in the flow layer consisting of 64 chambers per column, with each chamber containing ~750 pL of liquid after compartmentalization and mixing. Liquid is loaded into these columns through two separate inputs under low external pressure (~20 kPa), filling up the array in a serpentine fashion. Barrier valves on the control layer function to isolate the sample fluids from each other and from channel networks on the flow layer used to recover the contents of each individual chamber. These networks function under the control of a multiplexor and several other control valves.

The storage array and comparator microfluidic devices shown in FIGS. 27A-H was fabricated with multilayer soft lithography techniques using two distinct layers. The "control" layer, which harbors all channels required to actuate the valves, is situated on top of the "flow" layer, which contains the network of channels being controlled. A valve is created where a control channel crosses a flow channel. The resulting thin membrane in the junction between the two channels can be deflected by hydraulic or pneumatic actuation. All biological assays and fluid manipulations are performed on the "flow" layer.

Master molds for the microfluidic channels were made by spin-coating positive photoresist (Shipley SJR 5740) on silicon 9 µm high and patterning them with high resolution (3386 dpi) transparency masks. The channels on the photoresist molds were rounded at 120° C. for 20 minutes to create a geometry that allows full valve closure.

The devices were fabricated by bonding together two layers of two-part cure silicone (Dow Corning Sylgard 184) cast from the photoresist molds. The bottom layer of the device, containing the "flow" channels, is spin-coated with 20:1 part A:B Sylgard at 2500 rpm for 1 minute. The resulting silicone layer is ~30 µm thick. The top layer of the device, containing the "control" channels, is cast as a thick layer (~0.5 cm thick) using 5:1 part A:B Sylgard using a separate mold. The two layers are initially cured for 30 minutes at 80° C.

Control channel interconnect holes are then punched through the thick layer (released from the mold), after which it is sealed, channel side down, on the thin layer, aligning the respective channel networks. Bonding between the assembled layers is accomplished by curing the devices for an additional 45-60 minutes at 80° C. The resulting multilayer devices are cut to size and mounted on RCA cleaned No. 1, 25 mm square glass coverslips, or onto coverslips spin coated with 5:1 part A:B Sylgard at 5000 rpm and cured at 80° C. for 30 minutes, followed by incubation at 80° C. overnight.

Simultaneous addressing of multiple non-contiguous flow channels is accomplished by fabricating control channels of varying width while keeping the dimension of the flow channel fixed (100 µm wide and 9 µm high). The pneumatic pressure in the control channels required to close the flow channels scales with the width of the control channel, making it simple to actuate 100 µm×100 µm valves at relatively low pressures (~40 kPa) without closing off the 50 µm×100 µm crossover regions, which have a higher actuation threshold.

Introduction of fluid into these devices is accomplished through steel pins inserted into holes punched through the silicone. Unlike micromachined devices made out of hard materials with a high Young's modulus, silicone is soft and forms a tight seal around the input pins, readily accepting pressures of up to 300 kPa without leakage. Computer-controlled external solenoid valves allow actuation of multiplexors, which in turn allow complex addressing of a large number of microvalves.

II. Microfluidic Matrix Architecture

Figure 28A:
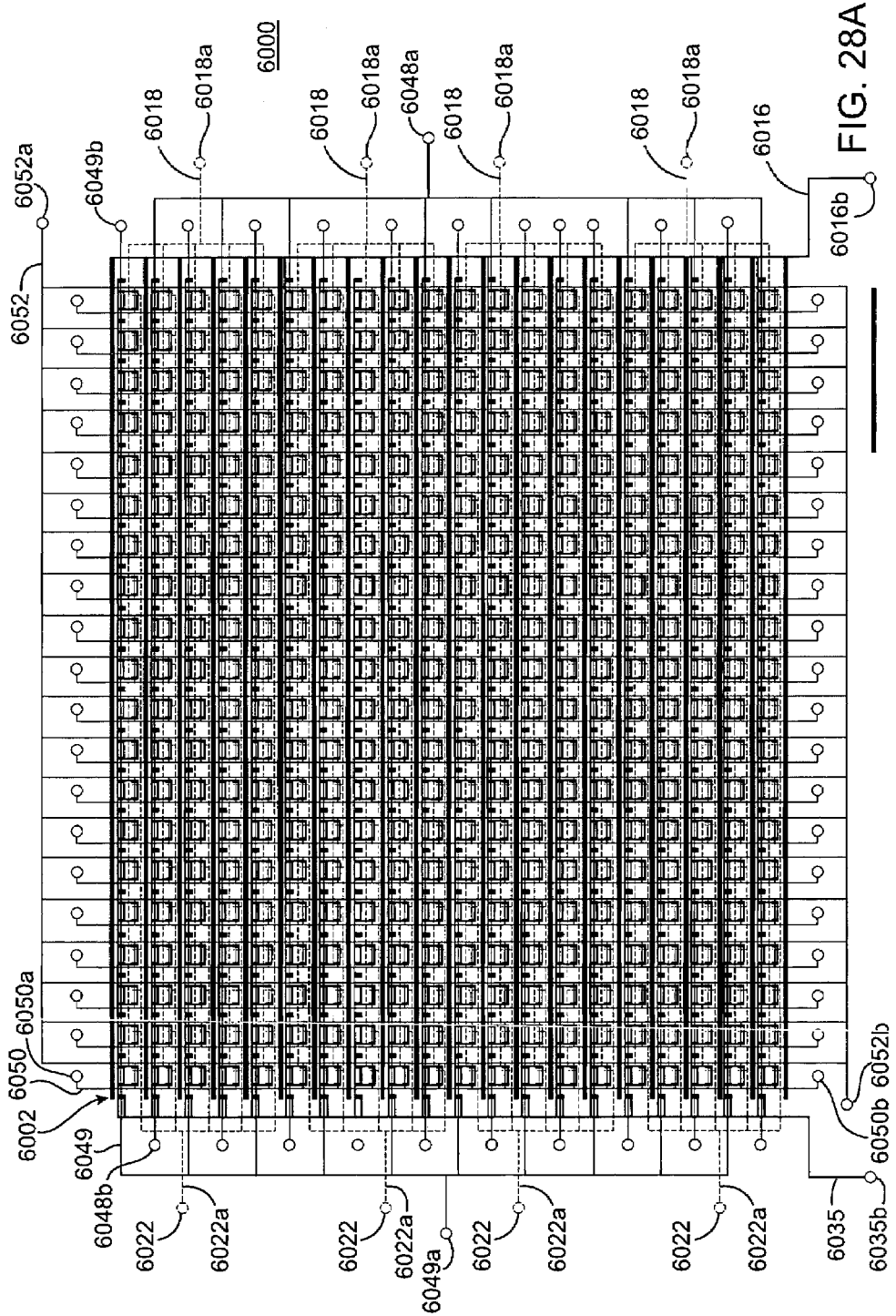
FIG. 28A shows a simplified schematic plan view of one embodiment of a microfluidic matrix architecture in accordance with the present invention.
Figure 28B:
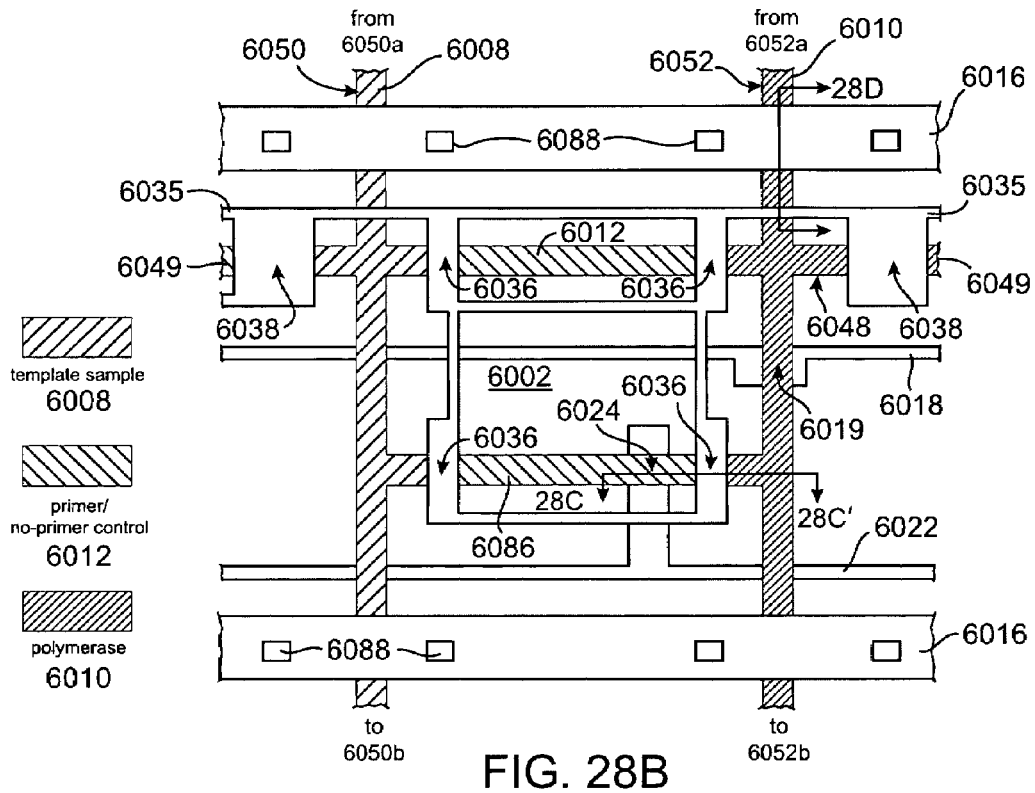
FIG. 28B shows an enlarged plan view of a single reactor x.

FIG. 28A shows a simplified schematic plan view of one embodiment of a microfluidic matrix architecture 6000 in accordance with the present invention, showing the N=20 matrix chip layout, and the various input, output and control ports. The scale bar of FIG. 28A is 6.4 mm. FIG. 28B shows an enlarged plan view of one reactor from the upper left hand corner of the matrix shown in FIG. 28A.

The apparatus of FIG. 28A features alternating row flow channels 6048 and 6049, intersecting with alternating column flow channels 6050 and 6052, with alternative pairs of successive flow channels 6050 and 6052 linked by branch flow channels 6086 to define reactor sites at the flow channel vertices. Each of flow channel row 6048 includes a common inlet port 6048a and an outlet port 6048b. Each of flow channel rows 6049 includes a common inlet port 6049a and an outlet port 6049b. As described below, in certain applications relating to the amplification of nucleic acids, flow channel rows 6048 may contain a primer, while flow channel rows 6049 may contain a no-primer control.

Each of alternate flow channel columns 6050 include an inlet port 6050a and an outlet port 6050b. Alternate flow channel columns 6052 include a common inlet port 6052a and an outlet port 6052b.

Each reactor 6002 of matrix 6000 is in pressure communication with control lines present in underlying and overlying elastomer layers. Specifically, First control lines 6016 overlap column flow channels 6050 and 6052, thereby defining valves 6016a. First control lines 6016 are in fluid communication with common port 6016a. Second control lines 6035 overlap row flow channels 6048 and branch flow channels 6086, thereby defining valves 6036 and 6038 having different widths. Second control lines 6035 are in fluid communication with common port 6035a.

First pump line 6018 underlies column flow channel 6052, thereby defining first push-up pumps 6019. Various separate groupings of first pump line 6018 are in fluid communication with common ports 6018a. Second pump line 6022 underlies branch flow channel 6086, thereby defining second push-up pumps 6024. Various groupings of second pump line 6022 are in fluid communication with common ports 6022a.

FIG. 28B shows an enlarged plan view of a single reactor 6002 featuring relatively large control lines 6016 including stabilizing post structures 6088, column flow line 6050 containing a first template sample 6008, a column flow line 6052 containing DNA polymerase 6010, and a row flow line 6049 containing primer 6012 or a no-primer control. The respective volume ratios are $V_{template}:V_{polymerase}:V_{primers}=3:3:4$. Rotary pumping valves 6019 and 6024 are defined between reactor 6006 and underlying pumping control channels 6018 and 6022.

Figure 28C:
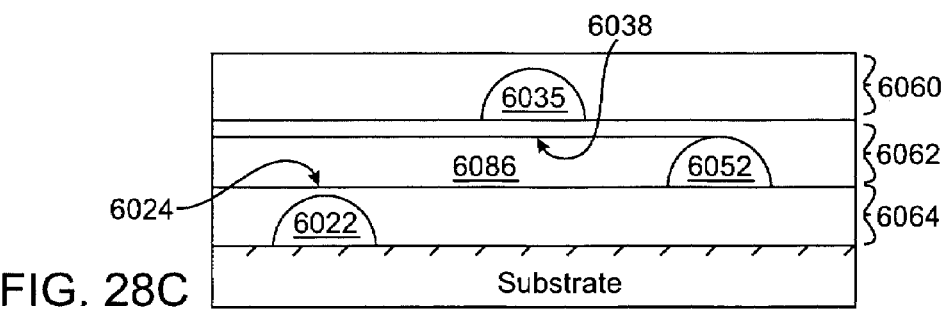
FIG. 28C shows a simplified cross-sectional view of the microfluidic matrix of FIG. 28B taken along line 28C-28C'.
Figure 28D:
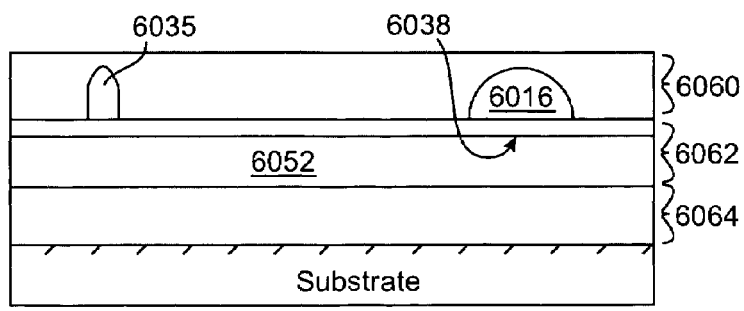
FIG. 28D shows a simplified cross-sectional view of the microfluidic matrix of FIG. 28D taken along line 28D-28D'.

FIG. 28C shows a simplified cross-sectional view of the microfluidic matrix of FIG. 28B taken along line 28C-28C'. FIG. 28D shows a simplified cross-sectional view of the microfluidic matrix of FIG. 28D taken along line 28D-28D'.

As shown in FIGS. 28C-D, the device 6000 comprises three layers 6060, 6062, and 6064 with distinct functions. Layer 6062 containing matrix flow channel structure 6006 is sandwiched between two layers 6060 and 6064 containing integrated hydraulic valves 6016a and pneumatic pumps 6019 and 6024, respectively.

In the middle fluidic layer 6062, flow channels 6006 are 106 pm wide and 12~14 µm high. Each vertex of the matrix 6000 contains a ring shaped channel (reactor) 6002 of approximate 3 nanoliters. Each row of reactors 6002 is connected to a separate input hole 6048a or 6049a (about 625 µm in diameter) through which unique primers or other reagents may be loaded. Each column can similarly load the reactors with different DNA templates or other reagents through second input holes 6050a. A third, single common input 6052a for the addition of polymerase or another reagent is connected to all the reactors in the matrix.

In the top, control layer 6060, the valve system is designed to load each reactor with the three separate reagents while preventing cross contamination. In total, 2860 valves displayed horizontally or vertically are controlled by only two independent pressure supply through-holes 6016b and 6035b. Furthermore, the large valves 6038 (270 µm wide) or the small valves 6036 (96 µm wide) can selectively be actuated because they have a different threshold of the hydraulic pressure. This is described by Unger et al. in *Science*, 288, 113-116 (2000) and Thorsen et al. in *Science*, 298, 580-584 (2002). As described by Unger et al., reagent loading is not blocked by the narrow control channels 6035a (42 µm wide) connecting the valve system, because their tiny membrane does not deflect at the actuation pressure used.

The third, bottom layer 6064 uses a 20×20 array of rotary pumps in order to facilitate mixing the reagents. The use of such devices is described by Chou et al., *Biomedical Microdevices*, 3, 323 (2001), and by Liu et al., *Electrophoresis*, 23, 1531-1536 (2002). In the specific embodiment illustrated in FIGS. 28A-D, each reactor 6002 features only two rotary pump structures 6019 and 6024. This represents a simplification over alternative embodiments of microfluidic matrix structures in accordance with the present invention, such as the alternative embodiment discussed below in conjunction with FIGS. 29A-D, wherein three such pumping structures underlie each rotary flow channel reactor. A minimum of only two such pumping structures are required to achieve peristaltic pumping, owing to the closed-loop nature of the rotary flow channel reactor at the vertices.

FIGS. 28E-H show enlarged and simplified plan views of a group of four adjacent reactors in the matrix of FIGS. 28A-D, illustrating successive steps of operation of the microfluidic matrix device.

Figure 28E:
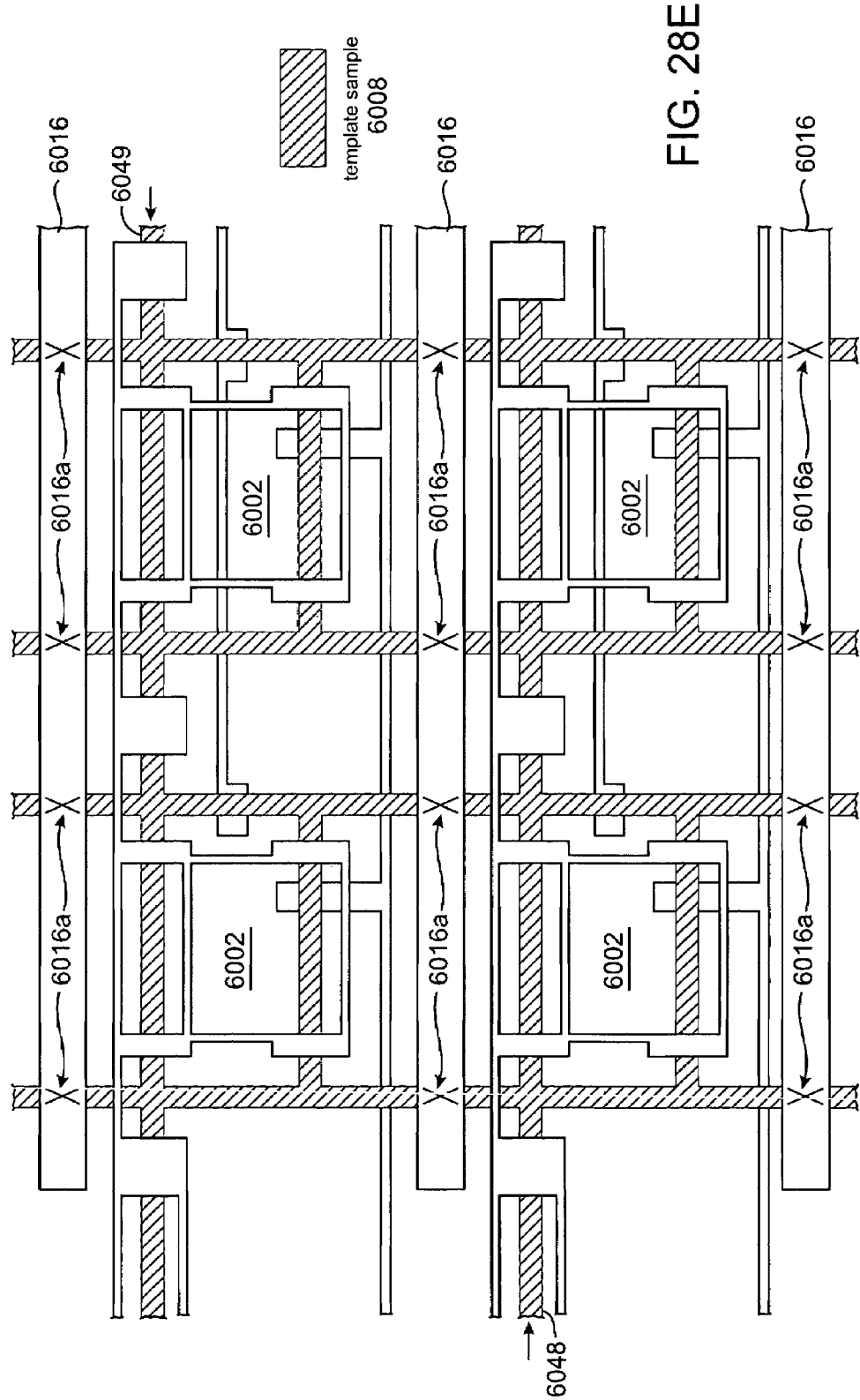
FIGS. 28E-H show enlarged and simplified plan views illustrating successive steps of operation of the microfluidic matrix of FIGS. 28A-D.

As shown in FIGS. 28E-H, active valves in the top control structure 6060 facilitate the loading and isolation of reagents 6008, 6010, and 6012. Specifically, as shown in FIG. 28E, with valves 6016a actuated, primer sets or other reagents 6012 are loaded along rows 6050 and 6052 respectively, of the matrix. Actuation of valves 6036 and 6038 isolates a well-defined volume of primers or other reagents 6012 in each reactor 6002.

Figure 28F:
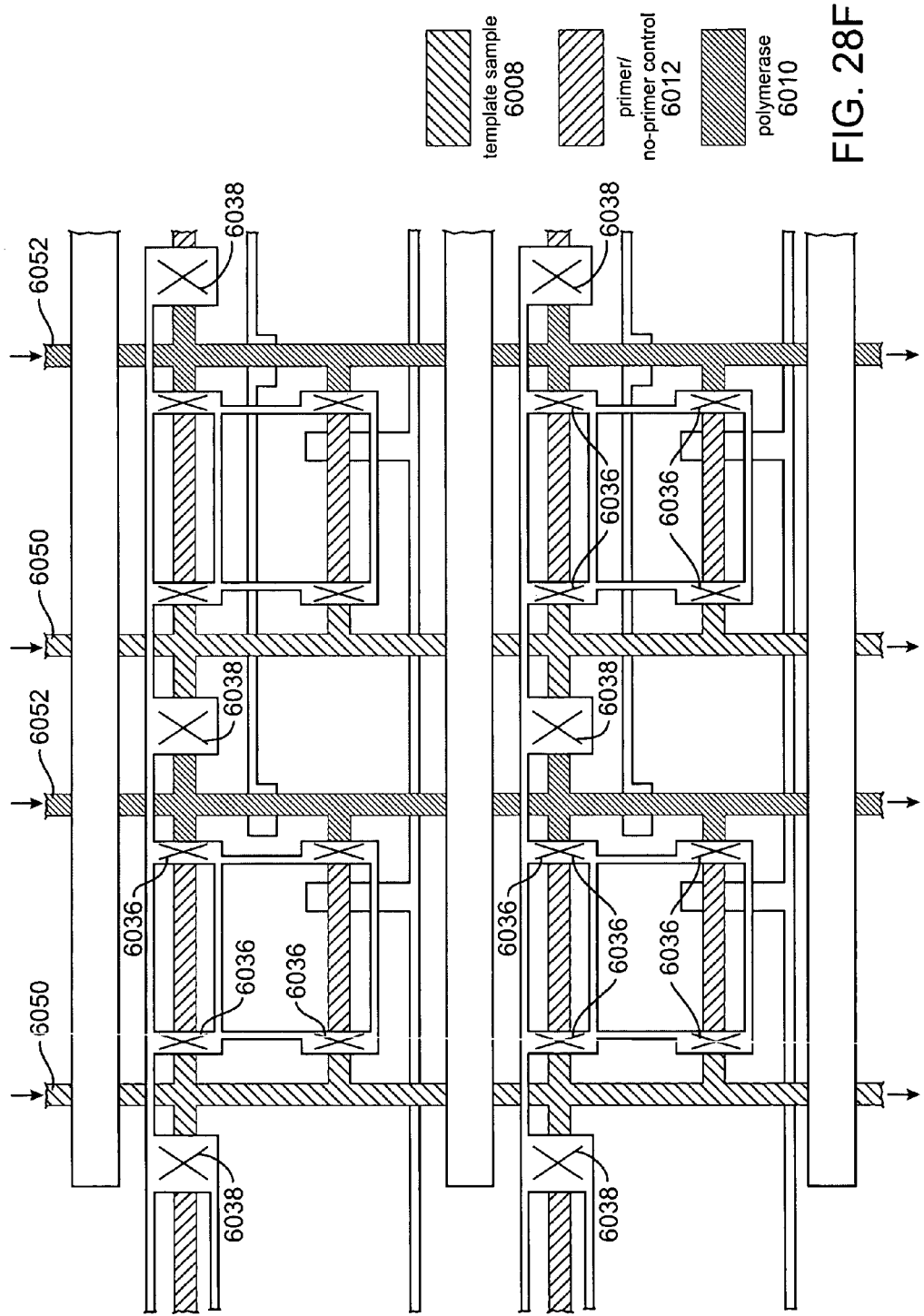

As shown in FIG. 28F, valves 6036 and 6038 are closed and valves 6016a opened, to allow for the loading of DNA templates or other reagents 6008 down alternate columns 6050 while polymerase or another reagent 6010 is simultaneously introduced to all reactors from a single inlet 6052a through alternate columns 6052. Valves 6016a are then once again actuated, defining the desired volumes of the different reagents 6008 and 6010 such as polymerase and templates, and isolating each reactor 6006a.

Figure 28G:
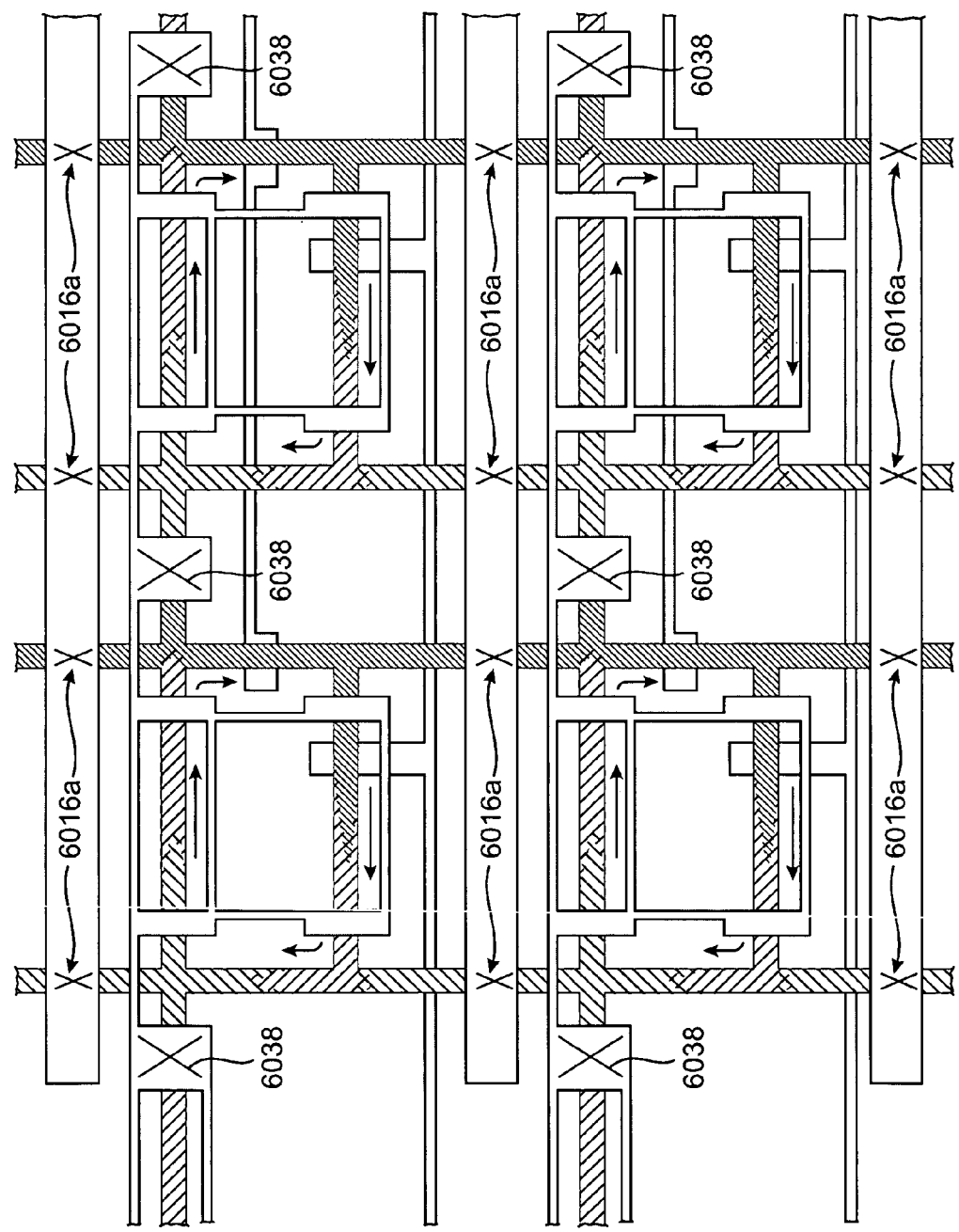
Figure 28H:
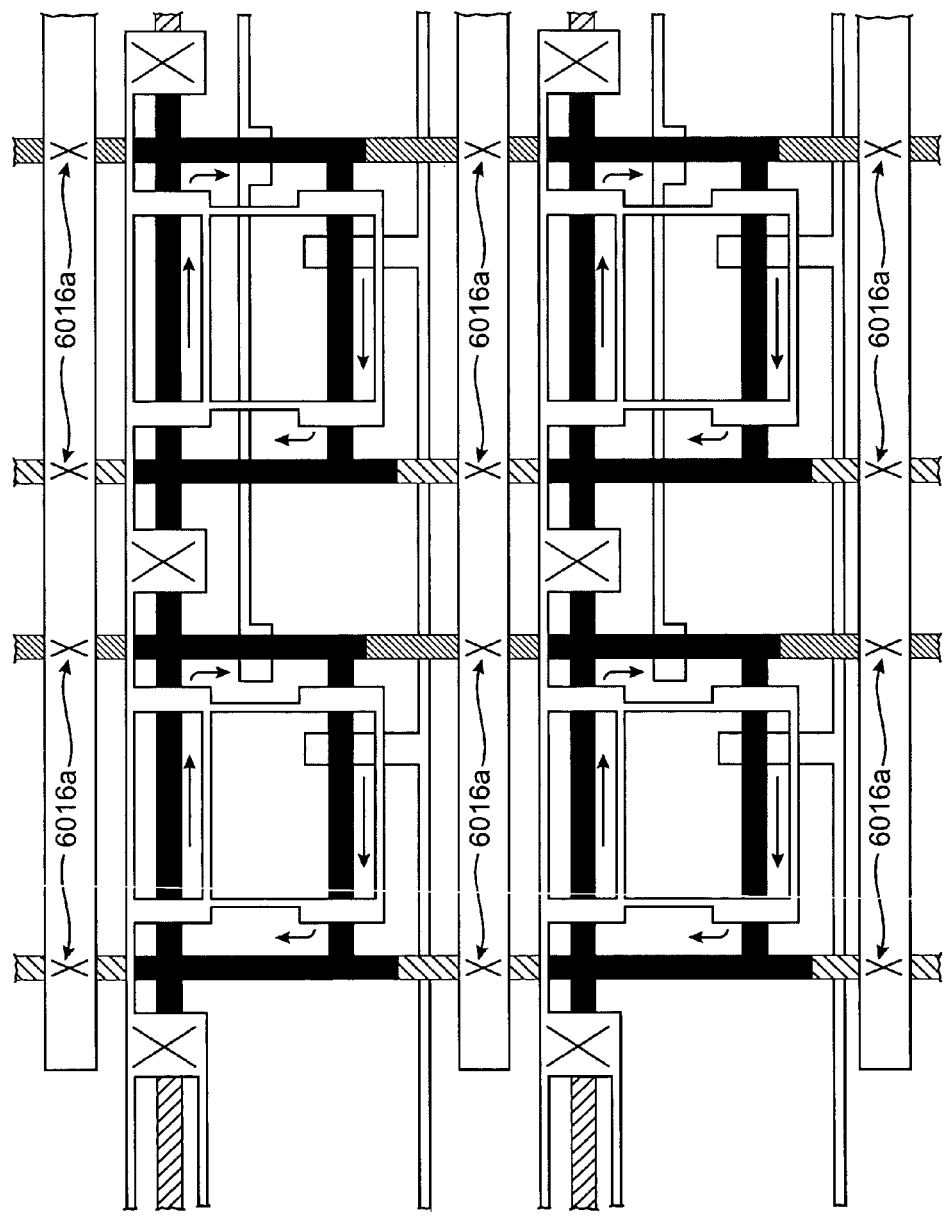

As described by Unger et al., the different membrane areas of valves 6036 and 6038 allow for the selective opening of only valves 6036 by reducing the actuation pressure from 260 kPa to 110 kPa, thus bringing all three components 6008, 6010, and 6012 into fluidic contact within each reactor 6002. As shown in FIG. 28G, peristaltic pumps 6019 and 6024 in the bottom layer allow for the rapid rotary mixing of all reagents within the reactors 6002.

FIGS. 29A-D show a set of optical micrographs illustrating the isolation and mixing of different dye solutions within an alternative embodiment of a microfluidic matrix device in accordance with the present invention. Four reactors are imaged. The scale bar of FIGS. 29A-D is 600 pm.

Figure 29A:
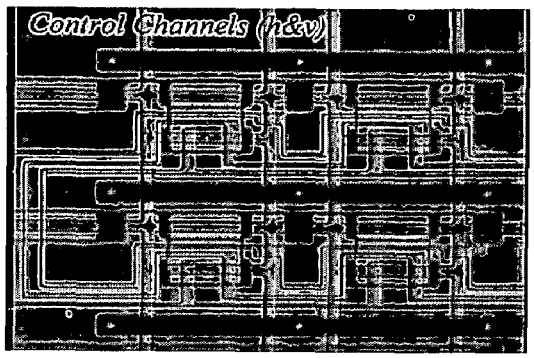
FIGS. 29A-D show a set of optical micrographs illustrating the isolation and mixing of different dye solutions by an alternative embodiment of a microfluidic matrix device in accordance with the present invention.

In FIG. 29A, the "dead-end" control channels are filled in with the green dye solution. This is feasible because PDMS is gas-permeable. See Hansen et al., *Proc. Natl. Acad. Sci. U.S.A.*, 99, 16531-16536 (2002), incorporated by reference herein for all purposes.

Figure 29B:
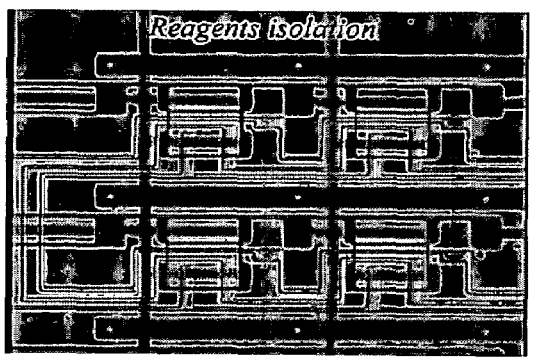
Figure 29C:
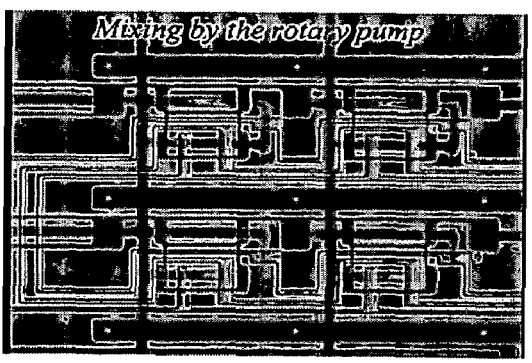

In FIG. 29B, different dye solutions are isolated into volume-defined compartments of the individual reactor. In FIG. 29C, the parabolic profile 6100 of the Poisueille flow stretches the interfaces of the reagents along the loop channel, producing long and thin interlaced steams which quickly mix by diffusion (shown here with food dyes), as described by Chou et al. Because of the valve ordering, the solutions are moving counter-clockwise in the first (top) row of reactors, while clockwise in the second (bottom) row.

Figure 29D:
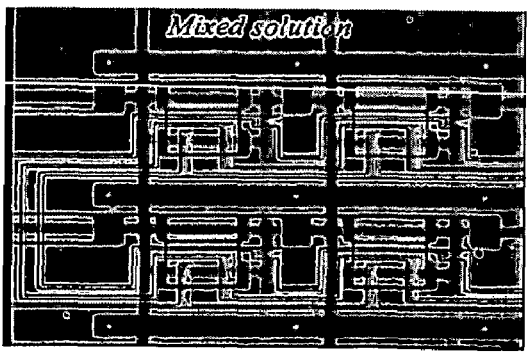

As shown in FIG. 29D, the color-mixed solution results from the rotary pumping for half a minute. A video of the loading and mixing sequence with food dye is available at http://thebigone.caltech.edu/quake/matrix.

The alternative embodiment of the microfluidic matrix device shown in FIGS. 29A-D differs in certain respects from the embodiment shown FIGS. 28A-H. First, as already described, circulation within the reactor is accomplished with three, rather than two, pumping structures. Owing, however, to the closed loop nature of the isolated reactor, it was recognized that peristaltic pumping could be accomplished utilizing only two pumps, thereby simplifying the layout.

In addition, in the embodiment of FIGS. 29A-D, pumps of adjacent reactors are connected by common, serpentine pumping control channels. However, it was observed that the number of reactors which could be pumped by such common pumping lines was limited, owing to accumulated delay in membrane actuation. Accordingly, the embodiment of FIGS. 28A-H features pumping control lines organized in groups sharing different common inlets/outlets, thereby reducing accumulated membrane delay.

The protocols of fabricating two-layer polydimethylsiloxane (PDMS) devices using multilayer soft lithography (MSL) have been previously described, at least by Fu et al., and Hansen et al. For the three-layer microfluidic matrix elastomeric devices in accordance with embodiments of the present invention, three separate molds for the different layers were prepared with UV-lithography. Photoresist of each mold layer may be heated to promote reflow and corresponding formation of rounded features.

The photoresist (Shipley SJR5740) line height was 12-44 μm on the fluidic layer mold or the pump layer mold. A 25 μm thick elastomeric layer with a 20:1 ratio was spin-coated on the fluidic layer mold at 1600 RPM for 65 seconds, then cured at 80° C. for 35 minutes.

The mold for the control layer had higher lines of 25 μm, which prevents collapse of the thin elastomeric membrane of the fluidic layer. To fabricate the control layer, General Electric RTV 615 A and B components were mixed in a 4:1 ratio using a Keyence Hybrid mixer. Then the mixture was poured onto the control layer mold in an foil-coated petri dish and baked in the oven at 80° C. for 30 minutes to obtain a thick PDMS block (~3-4 mm).

After incubation, the control layer was peeled from the mold and punched with through-holes for pressure connection. It was aligned on the thin fluidic layer and then baked at 80° C. for 45 minutes.

A third pump layer was spin-coated with the RTV615 mixture (20:1) at 2200 RPM for 65 seconds, and then incubated at 80° C. for 45 minutes. Next, the bonded device containing the former two control and fluidic layers was peeled and through-holes were punched for loading fluidic samples.

The bonded device was then aligned onto the third pump layer and baked at 80° C. overnight. Then the rest through-holes were punched on the device for air injection in pumping. After that, the three-layer device was sealed with a piece of glass coverslip (#1, Lakeside microscope accessories) and incubated at 80° C. for no less than 3 hours.

III. PCR

Nucleic acid amplification reactions have emerged as powerful tools in a variety of genetic analyses and diagnostic applications. The value of these techniques is their ability to rapidly increase the concentration of target nucleic acids of interest that might be present at very low and otherwise undetectable levels. For instance, by utilizing the polymerase chain reaction (PCR) amplification technique, one can amplify a single molecule of a target nucleic acid by $10^6$ to $10^9$.

PCR is perhaps the most well-known of a number of different amplification techniques. This well established procedure involves the repetition of heating (denaturation) and cooling (annealing) cycles in the presence of a target nucleic acid, primers that hybridize to the target, deoxynucleotides, a polymerase and cofactors such as metal ions. Each cycle produces a doubling of the amount of the target DNA. The cycles are conducted at characteristic temperatures: 95° C. for denaturing double stranded nucleic acid, 50 to 65° C. for hybridization of primer to the target nucleic acid, and 72 to 77° C. for primer extension (see, generally, Sambrook et al., *Molecular Cloning: A Laboratory Manual*, 2nd ed., Cold Spring Harbor Laboratory Press (1989), incorporated by reference herein for all purposes. See also for example, U.S. Pat. Nos. 4,683,202 and 4,683,195, both of which are incorporated by reference herein for all purposes.

Methods for conducting PCR amplifications fall into two general classes. The approach typically utilized is a time domain approach in which the amplification reaction mixture is kept stationary and the temperature is cycled. See, e.g., Cheng, et al., *Nucleic Acids Res*. 24:380-385 (1996); Shoffer, et al., *Nucleic Acids Res*. 24:375-379 (1996); and Hong, et al. *Electrophoresis* 22:328-333 (2001), each of which is incorporated herein by reference for all purposes. While methods utilizing this approach can be conducted with relatively small sample volumes, the methods require complex regulation of heater elements and relatively long reaction times.

Another approach that has been discussed is limited to a space domain approach in which three temperature zones are constantly kept at the different temperatures and the reaction mixture runs in a serpentine flow channel above it. See, e.g., Kopp et al., Science 280:1046-1048 (1998), incorporated by reference herein for all purposes. A method such as this can be conducted at relatively high speed because it is not necessary to heat and cool the heaters, but requires the use of relatively large sample volumes.

Figure 34:
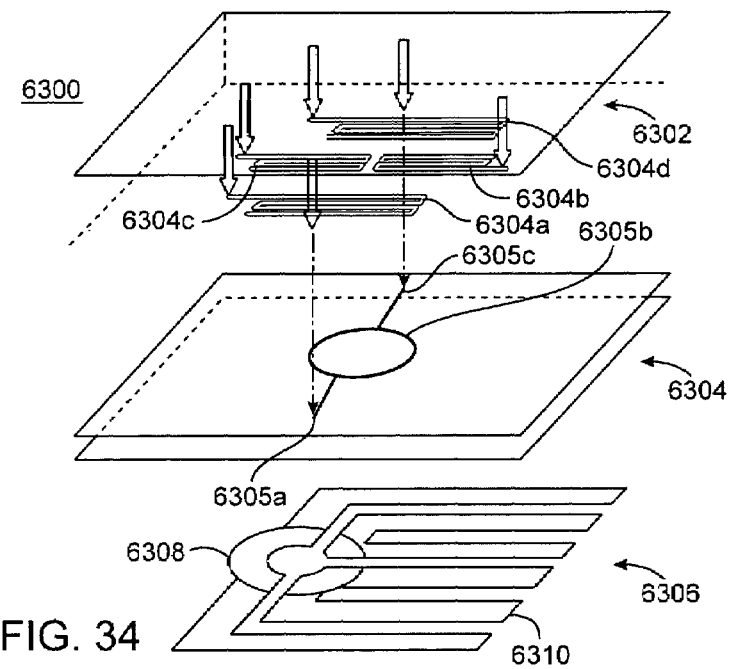
FIG. 34 shows an exploded view of an alternative embodiment of a microfluidic structure for performing PCR.

FIG. 34 shows a schematic diagram of one embodiment of a microfluidic structure 6300 for performing PCR. Top layer 6302 includes control channels 6304a-d for controlling the pumps and valves. Middle layer 6304 defines the inlet 6305a, rotary 6305b, and outlet 6305c fluid flow channels. Bottom layer 6306 includes integrated heater structures 6308 and electrical leads 6310 in electrical communication therewith.

The loop in the fluid layer forms a rotary pump, by which the PCR reagents can be transported over regions of different temperatures. The temperatures are set by tungsten heaters evaporated onto glass, which become the bottom substrate of the nanofluidic chip. The total volume of the PCR reaction was 12 nL.

Figure 35:
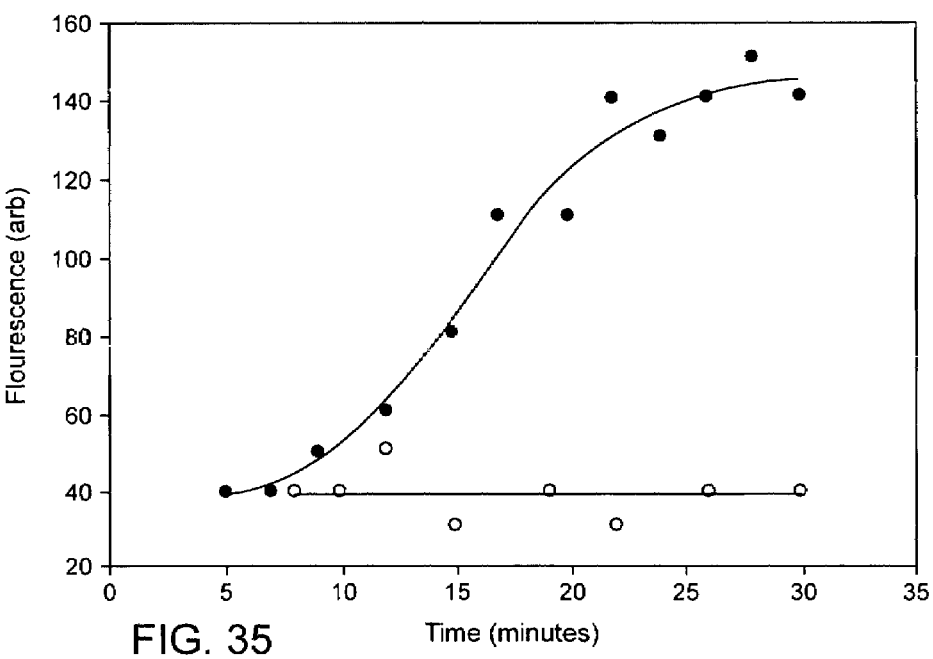
FIG. 35 plots fluorescence versus time for nucleic acids amplified by PCR utilizing the microfluidic structure shown in FIG. 34.

FIG. 35 shows results of Taqman PCR assay performed in the rotary pump chip. Fluorescence was measured in situ at various time points as the PCR reaction mixture was pumped through different temperature regions. A fragment of the β-actin gene was amplified from human male genomic DNA. The closed circles represent data from an experiment which contained the human template DNA. The open circles represent data from a negative control experiment in which template DNA was withheld.

Amplification of purified nucleic acid samples in accordance with embodiments of the present invention is not limited to the specific microfluidic structure shown in FIG. 34. Alternative, more complex microfluidic geometries are possible.

For example, the microfluidic matrix device shown in FIGS. 28A-H could be utilized to perform PCR. In order to test the performance of the microfluidic matrix chips just described, a number of experiments were performed.

Specifically, each row of reactors was alternatively loaded with primers and no-primer controls. Each column of reactors was then loaded with the cDNA template and no-template controls. The DNA template concentration was titrated along the positive control columns in order to test sensitivity.

The polymerase was loaded from the single inlet and amortized over all the independent reactors. The reactors containing all the necessary reagent components for PCR produced the positive signals (yellow, a mixed color of green and dim red); while those reactors that missed one or two reagent components showed a color of dim red, which derived from the passive reference dye in the buffer solution. The expected image is a checkerboard pattern, and any cross-contamination or leakage between compartments will be evident.

In these experiments, a 294-bp segment of the human (3-Actin cDNA fragment (1.8 Kbp, Clontech) was amplified. Forward primer and reverse primer were the following: 5'-TCA CCC ACA CTG TGC CCA TCT ACG A-3' and 5-'CAG CGG AAC CGC TCA TTG CCA ATG G-3'. An amplification protocol supplied by Applied Biosystems (http://www.appliedbiosystems.com) was modified to include the use of DyNAzyme II (0.1 U/reaction, Finnzymes OY) and additives. See Yang et al., Lab on a Chip, 2, 179-187 (2002). The solutions loaded onto the chip were prepared with one component of the template, primers or polymerase, and all other necessary PCR reagents and additives.

To simplify the pipetting steps for the checkerboard experiments, two sets of N/2 inputs/outputs are connected together for primer loading. The volumes loaded were 3 μl primers and no-primer control, 1 μl cDNA or no-template control, and 2 μl Dynazyme. An efficient mixing of the reagents was achieved by actuating the rotary pumps with two pneumatic controllers (Fluidigm Inc., So. San Francisco) at 10 Hz for 5 minutes.

After mixing was complete, the matrix chip was transferred onto a flat-bed thermocycler (DNA Engine, MJ Research). All the individual reactors were still isolated by the hydraulic control channels, which reduced the evaporation of the reagents in the fluidic channels to a negligible level.

The whole chip was thermocycled in the following protocol: 2 minutes at 50° C., and 1 minute at 96° C.; then 30 cycles: 20 seconds at 96° C.; 40 seconds at 60° C. The PCR conditions were verified with conventional methods to show that there are no detectable side products from the non-hot start condition. After thermocycling, the fluorescence emission from the PCR products in the chip (519 nm and 570 nm) was imaged using a modified DNA array scanner (Applied Precision).

Figures 30, 31:
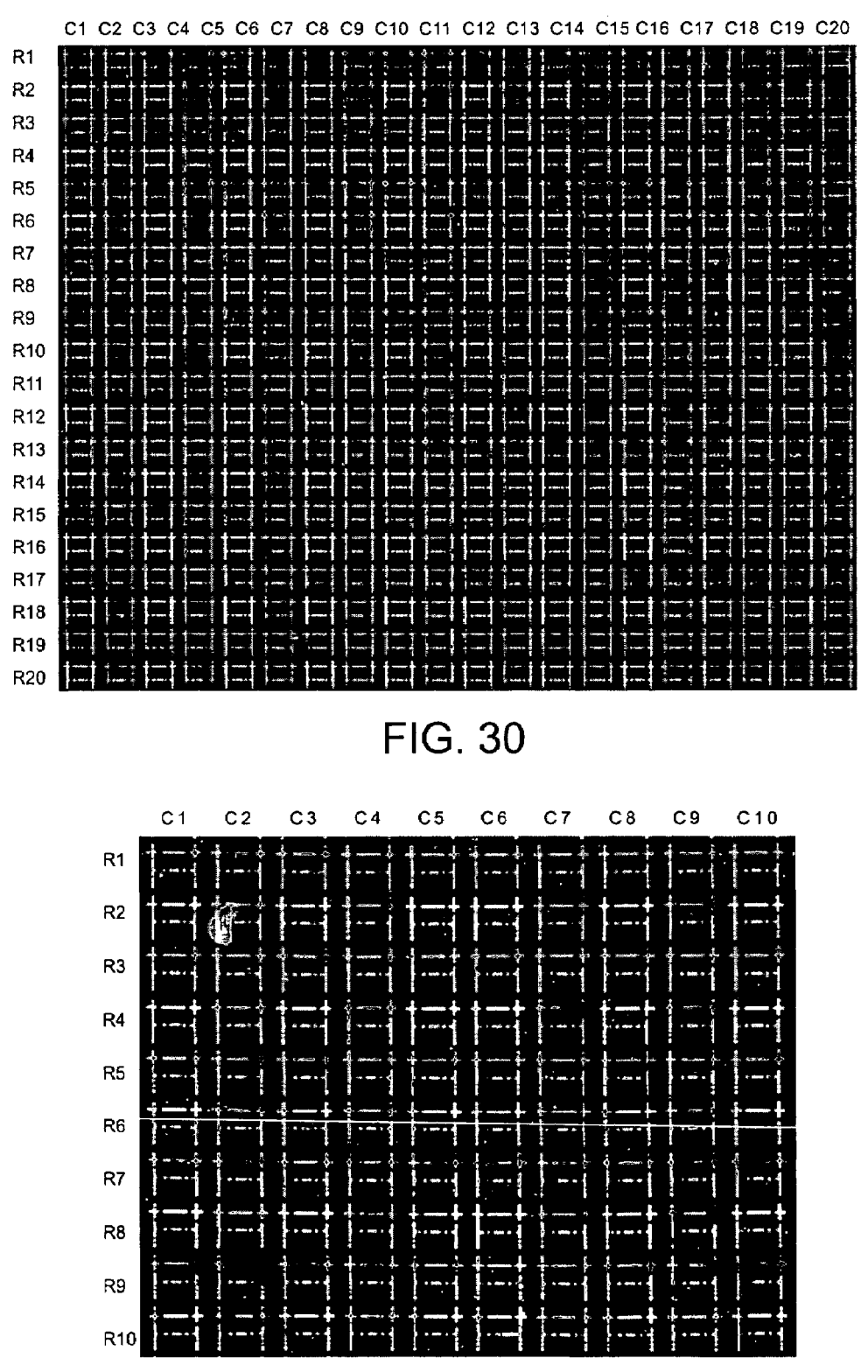

FIG. 30 shows a two-color image of fluorescent emission from a 20×20 matrix chip. Yellow indicates a positive signal from the sample. The no-template or no-primer controls show a dim red produced by the passive reference dye in the buffer. The concentration of the DNA templates is as follows (copies per reactor): C1&C3 (6,100), C5&C7 (3,050), C9&C11 (610), C13&C15 (305), C17&C19 (61). A threshold fluorescent ratio is established to define the false positive/negative signal. Some reactors in columns 17&19 do not show the desired positive signals, establishing the sensitivity of the chip. The scale bar of FIG. 30 is 6.4 mm.

FIG. 31 shows a scanned fluorescent image illustrating use of a 10×10 matrix chip in which an alternative reagent format was used. The scale bar of FIG. 31 is 6.4 mm.

Specifically, the matrix chip of FIG. 31 was used to explore combinations of forward and reverse primers. The three main components with all the other necessary PCR reagents and additives were as follows: component I included both the cDNA template and the polymerase; components II contained forward primers while component III contained reverse primers. Components II and III were loaded in the rows and columns of the matrix, respectively. Then component I, which contained both the cDNA template and the polymerase, was loaded into all the reactors from the single input.

Even-numbered rows are loaded with the correct forward primers, while odd rows are negative controls. Columns 1, 3, 5, 6, 8, and 10 are loaded with the correct reverse primers, while the remainder columns are negative controls. Thus, one should only observe successful PCR reactions in those reactors at the vertices of correct forward and reverse primers, as shown. Reactor C6R9 shows a false positive signal, which possibly resulted from the contamination of the forward primer of the neighboring reactors in the same column (C6).

In this manner, all possible combinations of forward and reverse primers can be tested with each other on a common DNA template. This format is particularly useful for PCR optimization and exon mapping.

The chip layout and sample loading sequence are specifically designed so that DNA template contamination among independent reactors is only possible if the valve system fails. Although there exists in principle a chance of slight primer contamination, the absolute numbers are so low that such an effect should not expected to affect the outcome of the assay. Possible primer contamination can be further reduced by flushing buffer solution into the fluidic channels before loading the DNA templates or polymerase.

In all, six separate 20×20 matrix chips and 8 separate 10×10 matrix chips were tested for a total of 3,200 reactions. Twenty-four out of 1550 positive control reactors produced false negative signals. In eighteen of these cases, the DNA concentrations were close to the detection limit. The other six reactors failed, possibly because of dust blocking the channels or other fabrication defects.

Thirty-five out of 1,650 negative controls showed false positive signals, perhaps due to the reagent leakage. In total, 98% of the 3,200 reactors tested produced the expected results.

Figure 32:
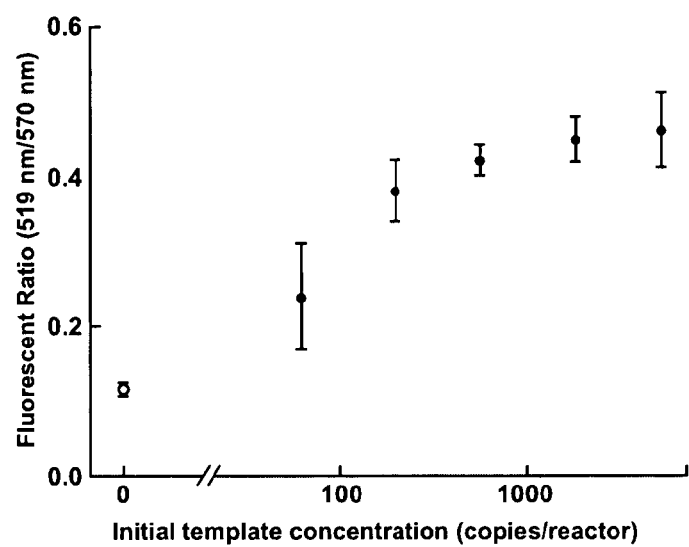
FIG. 32 plots fluorescent ratio vs. the initial concentration of the cDNA templates.

By titrating the template DNA concentration, the detection limit of the chip was established to be around 60 template copies per reactor. FIG. 32 plots fluorescent ratio vs. the initial concentration of the cDNA templates. Each symbol represents the averaged ratio of 20 reactors containing the same template concentration, with an error bar showing the standard deviation. There is no significant difference between the no-template control and the no-primer control. As the concentration decreases to the limit of detection, the standard deviation increases due to a mixture of positive and false negative results.

An immediate application of the microfluidic matrix device exists in medical diagnostics and genetic testing, where the matrix chip allows N patients to be screened for N mutations or pathogens with PCR or other techniques such as fluorescent-labeled mismatch-binding protein. See Behrensdorf et al., *Nucleic Acids Res.*, 30, e64 (2002).

Another application of interest is gene expression analysis, where reverse transcriptase PCR can be used to query N mRNA samples for the expression levels of N different genes.

In another experiment, positive samples were loaded into every reactor in order to collect as much PCR product as possible. The scanned fluorescent image (not shown) demonstrates that all the 400 reactors worked as expected.

For this experiment, the chip pattern was slightly modified to connect together all the inputs/outputs for primer loading/unloading. Thus, the PCR product could be flushed with TE buffer solution (about 40 μl) and collected with a pipette tip plugged into the wired outputs.

Figure 33:
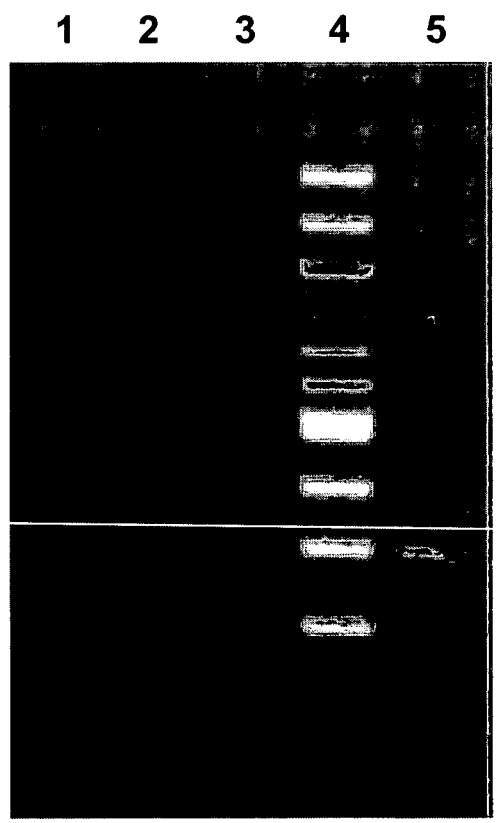
FIG. 33 shows Agarose gel electrophoresis of the PCR amplicon by the chip or by a microtube.

The solution of the extracted PCR amplicon was concentrated into a volume of about 5 μl by evaporation. This pooled amplicon was then verified by gel electrophoresis. FIG. 33 shows Agarose gel electrophoresis of the PCR amplicon by the chip or by a microtube. FIG. 33 is displayed in 2% Agarose gel with easy-cast electrophoresis system (Model BIA, VWR), stained with Sybr Green I, and documented by the Kodak electrophoresis system.

The sample of lane 1 of FIG. 33 is 1 μl PCR amplicon by the microtube. The sample of lane 2 of FIG. 33 is 0.5 μl PCR amplicon by the microtube. The sample of lane 3 is a negative control by the microtube. The sample of lane 4 is 100 bp DNA ladder. The sample of lane 5 is extracted PCR amplicon (400 reactors×3 nl/reactor) by the matrix chip.

Intensity of the pooled amplicon was comparable to the bench-top positive controls (lane 1 and lane 2). In future devices it should be possible to integrate on chip capillary electrophoresis for in situ product analysis beyond the information provided by the Taqman assay.

To summarize, embodiments of microfluidic matrix architectures in accordance with the present invention represent an effective solution to the macroscopic/microfluidic interface issue, and demonstrate how microfluidics can achieve impressive economies of scale in reducing the complexity of pipetting operations. Using an N×N microfluidic matrix with $N=20$, $N^2=400$ distinct PCR reactions were performed with only $2N+1=41$ pipetting steps, compared with the $3N^2=1,200$ steps required with conventional fluid handling. Each vertex of the matrix has a 3 nanoliter reactor, and a single 2 μL aliquot of polymerase is amortized over all 400 independent reactions, thus dramatically reducing sample overhead and minimizing reagent consumption.

While the specific embodiment shown and described above performs PCR by the introduction of primers, nucleic acid samples, and enzymes through separate inlets, this is not required by the present invention. In accordance with one alternative embodiment, the three separate inlet channels can be utilized to flow forward primers, reverse primers, and a mixture of nucleic acid sample and enzyme, respectively, into the three inlets to the flow channels of a microfluidic matrix device.

And while the specific embodiment of a microfluidic device shown and described above is fabricated from three layers of elastomer material, this is also not required by the present invention. In accordance with alternative embodiments, control lines of different widths defining membranes of varying size that are actuable at different applied pressures, could formed in a single elastomer layer adjacent to the fluidic flow layer. These various control lines could be utilized to perform reactor gating, isolation, and circulation functions.

Moreover, the embodiments of microfluidic devices in accordance with the present invention are not limited to the specific matrix architecture shown and described in connection with FIGS. 28A-H and 29A-D. For example, alternative embodiments of microfluidic devices in accordance with the present invention could include features that allow for recovery of the contents of individual reactors following reaction. FIGS. 36A-D show simplified plan views showing operation of one such alternative embodiment.

Figure 36A:
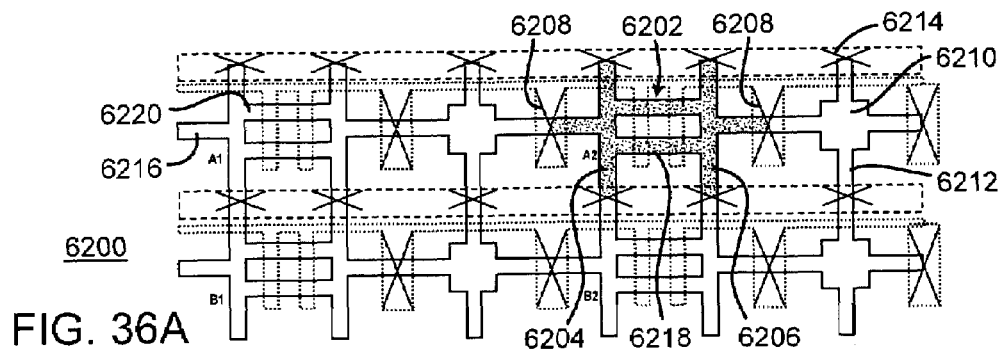

FIG. 36A shows an initial step of operation, wherein reactor 6202 of microfluidic matrix device 6200 has been loaded with reagents through column flow channel pairs 6204 and 6206, followed by reaction by circulation within reactor 6202 isolated by actuation of adjacent valves 6208, to form reaction product 6218. The pumping structures responsible for circulating fluid within the reactor 6202 have been omitted from FIGS. 36A-D for clarity of illustration.

The architecture of the microfluidic matrix device shown in FIG. 36A differs from that of prior Figures in two important respects. First, each rotary reactor 6202 is fabricated adjacent to a holding chamber 6210, that is in turn in fluid communication with an additional column flow channel 6212 gated by valves 6214. As described below in connection with FIGS. 36B-C, holding chamber 6210 and recovery flow channel 6212 play a key role in permitting recovery of the contents of individual reactors from the microfluidic matrix.

Figure 36B:
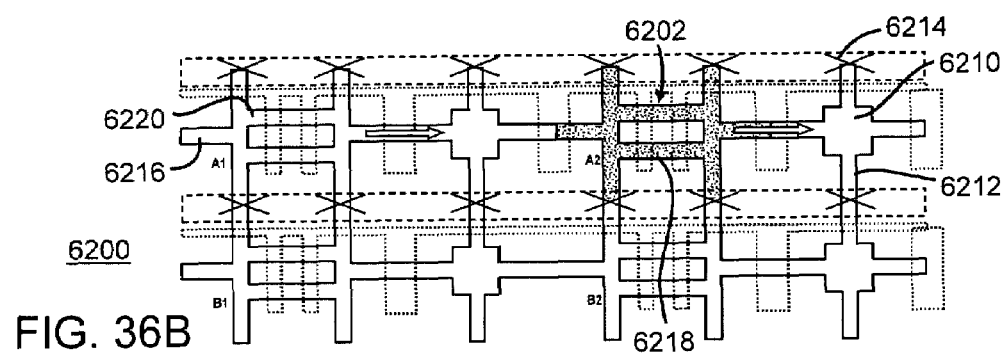

A second key difference between the architecture of the microfluidic matrix device shown in FIG. 36A and those discussed previously, is that the reactors are formed from pairs of horizontal branch channels connecting alternative pairs of column flow channels, rather than from continuous row flow channels. This architectural aspect becomes important in ensuring efficient and complete transfer of the contents of the reactor to the adjacent holding chamber, as shown in FIG. 36B.

Specifically, leaving valves 6208 open, buffer solution is flowed into row flow channel 6216, thereby displacing reaction product 6218 present in reactor 6002 into holding chamber 6210. Offsetting the position of upper branch flow channel 6220 from row flow channel 6216 in this embodiment, ensures that the contents of the reactor are captured and transferred during this process.

Figure 36C:
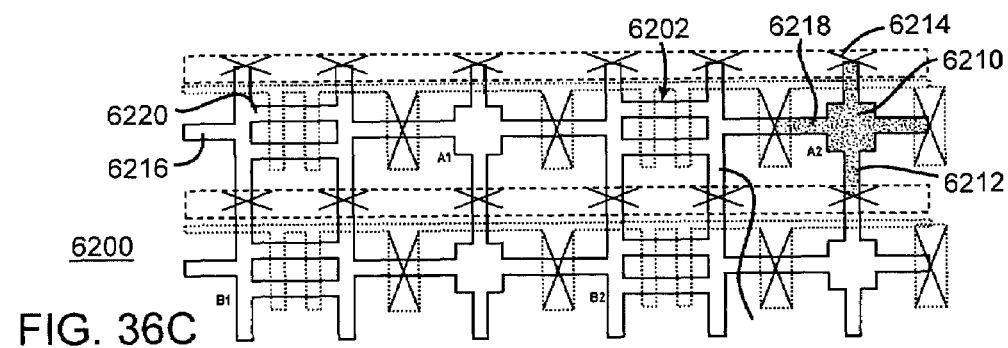
Figure 36C:
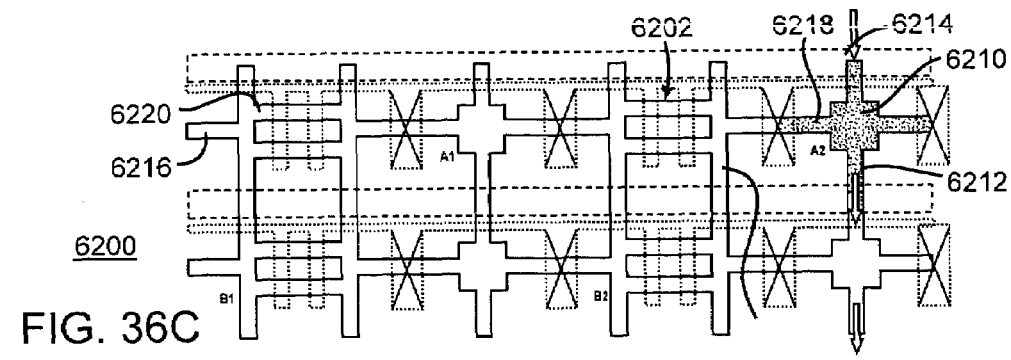

FIG. 36C shows the next step in the process, wherein the reaction product 6218 is isolated in holding chamber 6210, by reactuating valves 6208. FIG. 36D shows the final step in the process, wherein the reaction product 6218 may be flushed from the microfluidic device and recovered at an outlet or other feature, due to the positive pressure within column recovery flow channel 6212.

It should be noted that when valves 6208 or 6214 are opened, some contamination may occur between neighboring reactors. Such contamination may be caused by convective mixing between the contents of adjacent reactors during pumping along the common row flow channel as shown in FIG. 36B. However, the contamination can be reduced to a minimum level by isolating the contents with the neutral buffer solution in the holding chambers.

Contamination may also result from the passive diffusion of materials, for example between adjacent reaction products pumped along a common column flow channel as shown in FIG. 36D. However, the amount of such contamination is slight, and its impact can often be neglected for many applications. For example, a reaction product comprising medium or high molecular weight DNA takes hours to diffuse a distance of hundreds of microns, while the process of recovering the specified product from the chip can be accomplished in only a few seconds.

In some instances, the microfluidic devices described herein can be used as an analytical tool to amplify a target nucleic acid potentially present in a sample and then detect the amplified product to determine whether the target nucleic acid is present or absent in the sample. Thus, amplification serves to enhance the ability to detect target nucleic acids present at low levels. When utilized in this manner, the devices can be used in a wide variety of different applications.

For example, the devices can be used in various diagnostic applications that involve a determination of whether a particular nucleic acid is present in a sample. Hence, samples can be tested for the presence of a particular nucleic acid associated with particular pathogens (e.g., certain viruses, bacteria or fungi), for instance. The devices can also be utilized for identification purposes, such as in paternity and forensic cases.

The methods and devices provided herein can also be utilized to amplify low levels of nucleic acid for further examination to detect or characterize specific nucleic acids that are correlated with infectious diseases, genetic disorders or cellular disorders (e.g., oncogenes associated with cancer). Genetic disorders are those that involve a specific deletion and/or mutation in genomic DNA. Examples of genetic diseases that can be detected include, but are not limited to, α- and β-thalassemia, cystic fibrosis and sickle cell anemia. Because the devices and methods disclosed herein can utilize very small sample volumes, they are useful in amplifying DNA samples obtained in conjunction with the prenatal diagnosis of genetic disease.

However, the amplification reactions can also be utilized as just one step of a more extensive process involving the diagnostic testing for particular target nucleic acids and in preparing sufficient nucleic acid for use in various genetic engineering applications. Hence, amplified sample can be used in a number of post amplification manipulations and analyses. Examples of such post amplification processes and analyses include, but are not limited to, sequencing of amplified products, cell-typing, DNA fingerprinting and mapping of DNA sequences.

Amplified products can also be generated for use in various genetic engineering applications. For instance, amplified product can be utilized to conduct recombination studies. In other applications, the devices are used to produce target DNA for insertion into a variety of vectors. Such vectors can then be used to transform cells for the production of desired products such as proteins, or nucleic acids in various therapeutic or biotechnological processes.

The microfluidic devices in accordance with embodiments of the present invention can also be utilized to conduct sequencing reactions such as chain termination methods using dideoxynucleotides. Sequencing reactions utilizing the devices disclosed herein can be conducted in different formats. One approach is to conduct four separate sequencing reactions, a separate reaction being conducted in four different thermal cycling devices as provided herein. Each of the four reactions contains target nucleic acid, a primer complementary to the target, a mixture of one dideoxynucleotide (ddNTP) (optionally labeled) with its counterpart deoxynucleotide (dNTP), and the other three dNTPs. Thus, each one of the reactions is conducted with a different ddNTP/dNTP mix. Following completion of the primer extension reactions, the different sized extension products can be separated by capillary gel electrophoresis. This separation can be performed in a separation module as described supra that is integrated with the present devices or in a stand alone capillary gel electrophoresis apparatus.

In addition, embodiments of microfluidic matrix devices can also be utilized in more streamlined formats in which reactions are conducted simultaneously in a single thermal cycling device using differentially labeled dideoxynucleotides. The resulting mixture of chain-terminated reaction products are then separated on a single capillary gel electrophoresis column. The identity of the dideoxynucleotide incorporated into the primer can be determined on the basis of the label.

Restriction digests of nucleic acids can also be conducted utilizing the microfluidic matrix devices in accordance with embodiments of the present invention. Temperature control in such reactions initially involves controlling the temperature within the device at a temperature that promotes the activity of the restriction enzyme (e.g., 1-3 hours at 30-50° C. depending upon the particular enzyme. The other temperature is selected to promote enzyme deactivation (e.g., 60° C. for 20 minutes).

Analyses to determine the identity of a nucleotide present at a polymorphic site, i.e. the site of variation between allelic sequences such as a single nucleotide polymorphism (SNP), can also be conducted with certain of the present devices. Often these analyses are conducted using single base pair extension (SBPE) reaction. A number of SPBE assays have been developed, but the general approach is quite similar. Typically, these assays involve hybridizing a primer that is complementary to a target nucleic acid such that the 3' end of the primer is immediately 5' of the variant site or is adjacent thereto. Extension is conducted in the presence of one or more labeled non-extendible nucleotides that are complementary to the nucleotide(s) that occupy the variant site and a polymerase. The non-extendible nucleotide is a nucleotide analog that prevents further extension by the polymerase once incorporated into the primer. If the added non-extendible nucleotide(s) is(are) complementary to the nucleotide at the variant site, then a labeled non-extendible nucleotide is incorporated onto the 3' end of the primer to generate a labeled extension product. Hence, extended primers provide an indication of which nucleotide is present at the variant site of a target nucleic acid. Such methods and related methods are discussed, for example, in U.S. Pat. Nos. 5,846,710; 6,004,744;

5,888,819; 5,856,092; and 5,710,028; and in WO 92/16657, each of which is incorporated herein by reference for all purposes.

Using devices as described herein, the temperature within a temperature control region can be selected to promote the primer annealing, primer extension and denaturation steps involved in these particular analyses, and thus allows these extension reactions to be conducted in a thermal cycling format.

IV. Other Applications

Beyond PCR, the matrix chip provides a general method to perform chemical and biological experiments with precious reagents in a highly automated fashion. For example, while the foregoing discussion of the microfluidic matrix devices has focused on their utility in conducting a large number of nucleic acid amplification reactions, it will be appreciated by those with ordinary skill in the art that such microfluidic devices can be utilized to conduct a wide variety of types of reactions and screening methods. Thus, by way of illustration but not limitation, the devices can be utilized to conduct synthetic reactions between a plurality of reactants. Using the device shown in FIGS. 28A-H, for instance, a first set of reagents can be introduced into the horizontal flow channels, a second set of reagents can be introduced into the vertical flow channels that have an independent inlet; and a third reagent can be introduced into the vertical flow channels that are connected to the shared inlet. Using the metering and mixing techniques discussed above, these various reagents can be combined within reactors formed at the vertices of the matrix in order to accomplish reaction.

Embodiments of microfluidic matrix devices according to the present invention can also be utilized to screen compounds for a desired activity. With the devices described in FIGS. 28A-H and 29A-D for example, typical screening methods involve introducing a set of test compounds into the horizontal flow channels, with another set of compounds, cells, vesicles or the like being introduced via the vertical flow channels. Mixing occurs at the junctions and the presence or absence of the desired activity can then be monitored at vertices of the matrix.

For instance, a wide variety of binding assays can be conducted utilizing the microfluidic devices disclosed herein. Interactions between essentially any ligand and antiligand can be detected. Examples of ligand/antiligand binding interactions that can be investigated include, but are not limited to, enzyme/ligand interactions (e.g., substrates, cofactors, inhibitors); receptor/ligand; antigen/antibody; protein/protein (homophilic/heterophilic interactions); protein/nucleic acid; DNA/DNA; and DNA/RNA. Thus, the assays can be used to identify agonists and antagonists to receptors of interest, to identify ligands able to bind receptors and trigger an intracellular signal cascade, and to identify complementary nucleic acids, for example. Assays can be conducted in direct binding formats in which a ligand and putative antiligand are contacted with one another or in competitive binding formats well known to those of ordinary skill in the art. Binding assays can be conducted in heterogenous formats, as well as homogenous formats. In the homogeneous formats, ligands and antiligands are contacted with one another in solution and binding complexes detected without having to remove uncomplexed ligands and antiligands. Two approaches frequently utilized to conduct homogenous assays are fluorescence polarization (FP) and FRET assays.

Immunological assays are one general category of assays that can be performed with certain of the microfluidic devices disclosed herein. Some assays are conducted to screen a population of antibodies for those that can specifically bind to a particular antigen of interest. In such assays, a test antibody or population of antibodies is contacted with the antigen. Typically, the antigen is attached to a solid support. Examples of immunological assays include enzyme linked immunosorbent assays (ELISA) and competitive assays as are known in the art.

A variety of enzymatic assays can be performed using some of the devices disclosed herein. Such enzymatic assays generally involve introducing an assay mixture containing the necessary components to conduct an assay into a flow channel or junction for reaction with an enzyme that is subsequently introduced. The assay mixtures typically contain the substrate(s) for the enzyme, necessary cofactors (e.g., metal ions, NADH, NAPDH), and buffer, for example. If a coupled assay is to be performed, the assay solution will also generally contain the enzyme, substrate(s) and cofactors necessary for the enzymatic couple.

A number of different cell reporter assays can be conducted with the provided microfluidic devices. One common type of reporter assay that can be conducted include those designed to identify agents that can bind to a cellular receptor and trigger the activation of an intracellular signal or signal cascade that activates transcription of a reporter construct. Such assays are useful for identifying compounds that can activate expression of a gene of interest. Two-hybrid assays, discussed below, are another major group of cell reporter assays that can be performed with the devices. The two-hybrid assays are useful for investigating binding interactions between proteins.

Cells utilized in screening compounds to identify those able to trigger gene expression typically express a receptor of interest and harbor a heterologous reporter construct. The receptor is one which activates transcription of a gene upon binding of a ligand to the receptor. The reporter construct is usually a vector that includes a transcriptional control element and a reporter gene operably linked thereto. The transcriptional control element is a genetic element that is responsive to an intracellular signal (e.g., a transcription factor) generated upon binding of a ligand to the receptor under investigation. The reporter gene encodes a detectable transcriptional or translational product. Often the reporter (e.g., an enzyme) can generate an optical signal that can be detected by a detector associated with a microfluidic device.

In addition to the assays just described, a variety of methods to assay for cell membrane potential can be conducted with the microfluidic devices disclosed herein. In general, methods for monitoring membrane potential and ion channel activity can be measured using two alternate methods. One general approach is to use fluorescent ion shelters to measure bulk changes in ion concentrations inside cells. The second general approach is to use of FRET dyes sensitive to membrane potential.

Assays of cell proliferation can also be monitored with certain of the microfluidic devices disclosed herein. Such assays can be utilized in a variety of different studies. For example, the cell proliferation assays can be utilized in toxicological analyses, for example. Cell proliferation assays also have value in screening compounds for the treatment of various cell proliferation disorders including tumors.

The microfluidic devices disclosed herein can be utilized to perform a variety of different assays designed to identify toxic conditions, screen agents for potential toxicity, investigate cellular responses to toxic insults and assay for cell death. A variety of different parameters can be monitored to assess toxicity. Examples of such parameters include, but are not limited to, cell proliferation, monitoring activation of cellular pathways for toxicological responses by gene or protein expression analysis, DNA fragmentation; changes in the composition of cellular membranes, membrane permeability, activation of components of death-receptors or downstream signaling pathways (e.g., caspases), generic stress responses, NF-kappaB activation and responses to mitogens. Related assays are used to assay for apoptosis (a programmed process of cell death) and necrosis.

By contacting various microbial cells with different test compounds, some of the devices provided herein can be used to conduct antimicrobial assays, thereby identifying potential antibacterial compounds. The term "microbe" as used herein refers to any microscopic and/or unicellular fungus, any bacteria or any protozoan. Some antimicrobial assays involve retaining a cell in a cell cage and contacting it with at least one potential antimicrobial compound. The effect of the compound can be detected as any detectable change in the health and/or metabolism of the cell. Examples of such changes, include but are not limited to, alteration in growth, cell proliferation, cell differentiation, gene expression, cell division and the like.

Additional discussion of biological assays that can be conducted with certain of the microfluidic devices disclosed herein is provided in commonly owned PCT application PCT/US01/44869, filed Nov. 16, 2001.

Beyond uses in performing multiple independent assays, embodiments of microfluidic matrix devices in accordance with the present invention could also be used for multi-step assays. For example, after the reactions of the first-step are completed in the formats demonstrated above, the products may be isolated into the central compartments of each of the individual reactors. The other compartments may then be filled with the reagents for the downstream assays by operating the valve systems exactly in the same way as before. Therefore, the intermediate products need not be extracted off the chip, facilitating the automation of the multi-step assays and simplifying chip design and operation. Furthermore, this approach can save the unavoidable loss or dilution of product in the dead volume of the chip and the outlet port.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the claims.

What is claimed is:

1. A microfluidic device comprising:
a plurality of flow channels defined within a first layer to form a matrix of rotary flow reactors;
a first set of control lines proximate to and separated from the flow channels by first membranes, the first membranes actuable to introduce fluids into the rotary flow reactors and to isolate the rotary flow reactors, and wherein the first set of control lines are defined in a second layer adjacent to the first layer; and
a second set of control lines proximate to and separated from the flow channels by second membranes, the second membranes actuable to cause peristaltic pumping of the fluids within the isolated rotary flow reactors, and wherein the second set of control lines are defined in a third layer adjacent to the first layer on a side opposite to the second layer.

2. The microfluidic device of claim 1 wherein the second layer overlies the first layer, and the third layer underlies the first layer.

3. The microfluidic device of claim 1 wherein the second layer underlies the first layer, and the third layer overlies the first layer.

4. The micro fluidic device of claim 1 wherein the flow channels are oriented in rows and columns, and the reactors are formed by intersection of a selection from a group consisting of:
a row flow channel and a column flow channel;
alternate successive pairs of a row flow channel or a column flow channel; and
a branch channel connecting the alternate successive pairs of the row or the column flow channels.

5. The microfluidic device of claim 1 wherein the flow channels are oriented in rows and columns, and the reactors are formed by branch flow channels connecting alternate successive pairs of one of row and column flow channels.

6. The microfluidic device of claim 1 wherein the first set of control lines exhibit a first width and a second width greater than the first width, a first membrane portion defined by the first width and actuable by a greater applied pressure to isolate the reactor, and a second membrane portion defined by the second width and actuable by a lesser applied pressure to permit circulation of fluid within the reactor.

7. The microfluidic device of claim 1 wherein the first set of control lines contain water and the second set of control lines contain air.

8. The microfluidic device of claim 1 wherein the second set of control lines are organized in groups sharing different common inlets and outlets.

9. The microfluidic device of claim 1 wherein the second set of control lines share common inlets and outlets.

10. The microfluidic device of claim 1 further comprising:
a holding chamber in fluidic communication with a reactor; and
a recovery flow channel in fluidic communication with the holding chamber and configured to receive contents of the reactor.

11. The microfluidic device of claim 10 wherein:
the flow channels are oriented in rows and columns;
the reactor is formed by a branch flow channel connecting an alternate successive pair of one of row and column flow channels;
the holding chamber is in fluidic communication with the reactor along the other of the row and column flow channels; and
the recovery flow channel is parallel to the other of the row and column flow channels.

12. A method of conducting a chemical reaction, the method comprising:
providing a microfluidic device comprising;
a plurality of flow channels defined within a first layer to intersect and form a matrix of rotary flow reactors;
a first set of control lines proximate to and separated from the flow channels by first membranes, wherein the first set of control lines are defined in a second layer adjacent to the first layer;
a second set of control lines proximate to and separated from the flow channels by second membranes, wherein the second set of control lines are defined in a third layer adjacent to the first layer on a side opposite to the second layer;

introducing first and second chemicals to the rotary flow reactors;

applying pressure to the first set of control lines to actuate the first membranes to isolate the rotary flow reactors; and applying pressure to the second set of control lines to actuate the second membranes to cause peristaltic pumping of the fluids within the isolated rotary flow reactors.

13. The method of claim 12 wherein the flow channels are oriented in rows and columns, and the reactors are formed by branch flow channels connecting alternate successive pairs of one of rows and columns, the method comprising:

flowing the first chemical to the reactor through a row flow channel; and flowing the second chemical to the reactor through a column flow channel.

14. The method of claim 13 wherein the alternate successive pairs of one of the rows and columns have separate inlets, the method further comprising flowing a third chemical to the reactor through the one of the alternate row and column flow channels.

15. The method of claim 14 wherein flowing the first chemical comprises flowing a primer, flowing the second chemical comprises flowing a nucleic acid sample, and flowing the third chemical comprises flowing an enzyme.

16. The method of claim 15 further comprising heating the microfluidic device to amplify the nucleic acid sample.

17. The method of claim 14 wherein flowing the first chemical comprises flowing a nucleic acid sample, flowing the second chemical comprises flowing a primer, and flowing the third chemical comprises flowing an enzyme.

18. The method of claim 17 further comprising heating the microfluidic device to amplify the nucleic acid sample.

19. The method of claim 14 wherein flowing the first chemical comprises flowing a forward primer, flowing the second chemical comprises flowing a reverse primer, and flowing the third chemical comprises flowing a mixture of an enzyme and a nucleic acid sample.

20. The method of claim 19 further comprising heating the microfluidic device to amplify the nucleic acid sample.

21. The method of claim 12 wherein:

applying pressure to the first set of control lines comprises applying pressure to a water-filled control line; and applying pressure to the second set of control lines comprises applying pressure to an air-filled control line.

22. The method of claim 12 wherein applying pressure to the second set of control lines comprises applying pressure to a plurality of inputs.

23. The method of claim 12 further comprising recovering a contents of the rotary flow reactors after the peristaltic pumping.

24. The method of claim 23 wherein recovering the contents comprises:

flowing the contents from the reactor into an adjacent holding chamber; and flowing the contents from the holding chamber along a recovery flow channel to an outlet.

25. The method of claim 24 wherein the contents are flowed to the outlet orthogonal to a direction of flow of the contents to the holding chamber.

* * * * *